(12) United States Patent
Mitsudera

(10) Patent No.: US 7,541,374 B2
(45) Date of Patent: Jun. 2, 2009

(54) MALONONITRILE COMPOUNDS AND USE THEREOF

(75) Inventor: Hiromasa Mitsudera, Toyonaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 539 days.

(21) Appl. No.: 10/582,001

(22) PCT Filed: Jan. 12, 2005

(86) PCT No.: PCT/JP2005/000555

§ 371 (c)(1),
(2), (4) Date: Jun. 7, 2006

(87) PCT Pub. No.: WO2005/068423

PCT Pub. Date: Jul. 28, 2005

(65) Prior Publication Data

US 2007/0117854 A1 May 24, 2007

(30) Foreign Application Priority Data

Jan. 16, 2004 (JP) ............................. 2004-009150

(51) Int. Cl.
*A01N 43/64* (2006.01)
*C07D 249/08* (2006.01)
(52) U.S. Cl. ................... 514/383; 548/267.4
(58) Field of Classification Search ............ None
See application file for complete search history.

(56) References Cited

U.S. PATENT DOCUMENTS

| 7,402,691 B2 * | 7/2008 | Otaka et al. ............ 558/461 |
| 2004/0142821 A1 | 7/2004 | Otaka et al. |

FOREIGN PATENT DOCUMENTS

| JP | 2004-99597 A | 4/2004 |
| WO | WO-02/089579 A1 | 11/2002 |
| WO | WO-02/090320 A2 | 11/2002 |
| WO | WO-02/090321 A1 | 11/2002 |
| WO | WO-2004/006677 A1 | 1/2004 |
| WO | WO-2004/020399 A1 | 3/2004 |

OTHER PUBLICATIONS

Patent Abstracts of Japan JP-10-029966 (Mar. 2, 1998).

\* cited by examiner

*Primary Examiner*—Kamal A Saeed
(74) *Attorney, Agent, or Firm*—Birch, Stewart, Kolasch & Birch, LLP

(57) ABSTRACT

A nitrile compound shown by the formula (1) has an excellent pesticidal activity and it is useful as an active ingredient of pesticide.

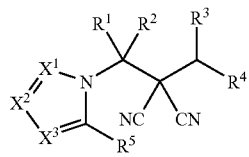

(I)

10 Claims, No Drawings

MALONONITRILE COMPOUNDS AND USE THEREOF

This Non-provisional application is the national phase of PCT International Application No. PCT/JP2005/000555 filed on Jan. 12, 2005, under 35 U.S.C. § 371; and claims priority under 35 U.S.C. § 119(a) on patent application Ser. No(s). Japanese Application No. 2004-009150 filed in Japan on Jan. 16, 2004, the entire contents of each of which are hereby incorporated by reference.

FIELD OF THE INVENTION

The present invention relates to a malononitrile compound having a five-membered ring containing a nitrogen atom and use thereof.

BACKGROUND ART

Compounds having pesticidal activity have been developed and practically used.

DISCLOSE OF THE INVENTION

The object of the present invention is to provide a compound having excellent activity against pests, a pesticidal composition comprising said compound as an active ingredient and a method for controlling pests applying said compound.

The present invention is a malononitrile compound represented by the formula (I):

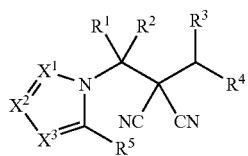

wherein, in the formula, $R^1$ represents a C1-C5 alkyl group optionally substituted by at least one halogen atom, a C2-C5 alkenyl group optionally substituted by at least one halogen atom, a C2-C5 alkynyl group optionally substituted by at least one halogen atom or a hydrogen atom;

$R^2$ represents a C1-C5 alkyl group optionally substituted by at least one halogen atom, a C1-C5 alkoxy group optionally substituted by at least one halogen atom, a C2-C5 alkenyl group optionally substituted by at least one halogen atom, a C2-C5 alkynyl group optionally substituted by at least one halogen atom, a cyano group or a hydrogen atom;

each of $R^3$ and $R^4$ represents a C1-C5 alkyl group optionally substituted by at least one halogen atom, a C2-C5 alkenyl group optionally substituted by at least one halogen atom, a C2-C5 alkynyl group optionally substituted by at least one halogen atom, a C3-C5 cycloalkyl group optionally substituted by at least one halogen atom or at least one C1-C3 alkyl group, a C4-C5 cycloalkenyl group optionally substituted by at least one halogen atom or a hydrogen atom, or represents a C2-C6 alkanediyl group optionally substituted by at least one halogen atom or C4-C6 alkenediyl group optionally substituted by at least one halogen atom in which $R^3$ and $R^4$ are coupled one another at the end thereof;

each of $X^1$, $X^2$ and $X^3$ represents a nitrogen atom or a $CR^6$;

each of $R^5$ and $R^6$ represents a halogen atom, a cyano group, a nitro group, a hydroxyl group, a mercapto group, a formyl group, a $SF_5$ group, a carboxyl group, a C1-C5 alkyl group optionally substituted by at least one halogen atom, a C2-C5 alkenyl group optionally substituted by at least one halogen atom, a C2-C5 alkynyl group optionally substituted by at least one halogen atom, a C3-C6 cycloalkyl group optionally substituted by at least one halogen atom or at least one C1-C3 alkyl group, a C1-C5 alkoxy group optionally substituted by at least one halogen atom, a C3-C6 alkenyloxy group optionally substituted by at least one halogen atom, a C3-C6 alkynyloxy group optionally substituted by at least one halogen atom, a C1-C5 alkylthio group optionally substituted by at least one halogen atom, a C3-C5 alkenylthio group optionally substituted by at least one halogen atom, a C3-C5 alkynylthio group optionally substituted by at least one halogen atom, a C1-C5 alkylsulfinyl group optionally substituted by at least one halogen atom, a C1-C5 alkylsulfonyl group optionally substituted by at least one halogen atom, a C2-C6 alkylcarbonyl group optionally substituted by at least one halogen atom, a C2-C5 alkoxycarbonyl group optionally substituted by at least one halogen atom, a group designated by $NR^{10}R^{11}$, a group designated by $C(=X^5)NR^{12}NR^{13}$, a group designated by $(CH_2)_mQ$, a group designated by $C(=NOR^{17})R^{18}$ or a hydrogen atom;

in case of two atoms are adjoined and each of the adjoined two atoms is bonded with one of $R^5$ and $R^6$ or two $R^6$s; the $R^5$ and $R^6$, which are bonded with the adjoined two atoms or the two $R^6$s, which are bonded with the adjoined two atoms, maybe coupled one another at the end thereof and represent a C2-C6 alkanediyl group optionally substituted by at least one halogen atom or C4-C6 alkenediyl group. And in this case, at least one methylene group structuring said alkanediyl group or said alkenediyl group may be replaced by an oxygen atom a sulfur atom or $NR^7$ group;

$R^7$ represents a C1-C5 alkyl group optionally substituted by at least one halogen atom, a C3-C5 alkenyl group optionally substituted by at least one halogen atom, a C3-C5 alkynyl group optionally substituted by at least one halogen atom, a C3-C6 cycloalkyl group optionally substituted by at least one halogen atom or at least one C1-C3 alkyl group, a C2-C6 alkylcarbonyl group optionally substituted by at least one halogen atom, a C2-C5 alkoxycarbonyl group optionally substituted by at least one halogen atom or a hydrogen atom;

each of $R^{10}$ and $R^{11}$ represents a C1-C5 alkyl group optionally substituted by at least one halogen atom, a C3-C5 alkenyl group optionally substituted by at least one halogen atom, a C3-C5 alkynyl group optionally substituted by at least one halogen atom, a C3-C6 cycloalkyl group optionally substituted by at least one halogen atom or at least one C1-C3 alkyl group, a (C1-C5 alkoxy group optionally substituted by at least one halogen atom) C1-C3 alkyl group, a C1-C5 alkylsulfinyl group optionally substituted by at least one halogen atom, a C1-C5 alkylsulfonyl group optionally substituted by at least one halogen atom, a C2-C6 alkylcarbonyl group optionally substituted by at least one halogen atom, a C2-C5 alkoxycarbonyl group optionally substituted by at least one halogen atom or a hydrogen atom;

each of $R^{12}$ and $R^{13}$ represents a C1-C5 alkyl group optionally substituted by at least one halogen atom, a C3-C5 alkenyl group optionally substituted by at least one halogen atom, a C3-C5 alkynyl group optionally substituted by at least one halogen atom, a C3-C6 cycloalkyl group optionally substituted by at least one halogen atom or at least one C1-C3 alkyl group, a group designated by $(CH_2)_mQ$ or a hydrogen atom;

or represents a C2-C6 alkanediyl group optionally substituted by at least one halogen atom or C4-C6 alkenediyl group optionally substituted by at least one halogen atom in which $R^{12}$ and $R^{13}$ are coupled one another at the end thereof;

each of $R^{17}$ and $R^{18}$ represents a C1-C5 alkyl group optionally substituted by at least one halogen atom, a C3-C5 alkenyl group optionally substituted by at least one halogen atom, a C3-C5 alkynyl group optionally substituted by at least one halogen atom, a C3-C6 cycloalkyl group optionally substituted by at least one halogen atom or at least one C1-C3 alkyl group, a group designated by $(CH_2)_mQ$ or a hydrogen atom;

Q represents an aryl group optionally substituted by at least one $R^{14}$;

each of $R^{14}$s represents a C1-C5 alkyl group optionally substituted by at least one halogen atom, a C3-C6 cycloalkyl group optionally substituted by at least one halogen atom or at least one C1-C3 alkyl group, a C1-C5 alkoxy group optionally substituted by at least one halogen atom, C1-C5 alkylthio group optionally substituted by at least one halogen atom, C3-C5 alkenylthio group optionally substituted by at least one halogen atom, a C3-C5 alkynylthio group optionally substituted by at least one halogen atom, a C1-C5 alkylsulfinyl group optionally substituted by at least one halogen atom, a C1-C5 alkylsulfonyl group optionally substituted by at least one halogen atom, C2-C6 alkylcarbonyl group optionally substituted by at least one halogen atom, C2-C5 alkoxycarbonyl group optionally substituted by at least one halogen atom or a halogen atom;

m represents an integer of from 0 to 5;

$X^5$ represents an oxygen atom or a sulfur atom.

Said malononitrile compound is referred to as "the compound of the present invention" hereinafter. The present invention further provides a pesticide composition comprising the effective amount of the compound of the present invention and a carrier, a method for controlling pests comprising applying an effective amount of the compound of the present invention to pests or at a habitat of pests and use of the compound of the present invention for pest control.

In the present invention, "alkanediyl group" represents a group having a free valency on two different carbon atoms contained in a saturated hydrocarbon chain, and "alkenediyl group" represents a group having a free valency on two different carbon atoms contained in a hydrocarbon chain having one or two double bonds.

In the present invention, "fluoroalkyl group" represents an alkyl group which is substituted by one or more fluorine atoms, the term such as C1-C6 indicates the total number of carbon atoms which is composed by each substituents.

In the compound of the present invention:

a C1-C5 alkyl group optionally substituted by at least one halogen atom represented by $R^1$ and $R^2$ includes, for example, C1-C3 alkyl group optionally substituted by at least one halogen atom such as a methyl group, an ethyl group, a propyl group, a 1-methylethyl group(may be referred to as an i-propyl group, hereinafter), a chloromethyl group, a fluoromethyl group, a difluoromethyl group, a trifluoromethyl group, a 2,2,2-trifluoroethyl group and a 1,1,2,2-tetrafluoroethyl group; and 1,1-dimethylethyl group(may be referred as t-butyl group, hereinafter);

a C2-C5 alkenyl group optionally substituted by at least one halogen atom includes, for example, a vinyl group, a 2,2-difluorovinyl group, a 1,2,2-trifluorovinyl group, 1-propenyl group and 2-propenyl group;

a C2-C5 alkynyl group optionally substituted by at least one halogen atom includes, for example, an ethynyl group, a 1-propynyl group, a 2-propynyl group and 3,3,3-trifluoro-1-propynyl group.

A C1-C5 alkoxy group optionally substituted by at least one halogen atom represented by $R^2$ includes, for example, a C1-C3 alkoxy group optionally substituted by at least one halogen atom such as a methoxy group, an ethoxy group, a 1-ethylethoxy group, a trifluoromethoxy group, a difluoromethoxy group, a 2,2,2-trifluoroethoxy group and a 1,1,2,2-tetrafluoromethoxy group; and a butoxy group.

A C1-C5 alkyl group optionally substituted by at least one halogen atom represented by $R^3$ and $R^4$ includes, for example, a methyl group, an ethyl group, a 1-methylethyl group, 2-methylpropyl group, a propyl group, a butyl group, a 3-methylbutyl group, a 2,2-dimethylpropyl group, a fluoromethyl group, a chloromethyl group, a 2,2-difluoroethyl group, a 2,2-dichloroethyl group, a 3,3-difluoropropyl group, a 3,3-dichloropropyl group, a trifluoromethyl group, a trichloromethyl group, a 2,2,2-trifluoroethyl group, a 2,2,2-trichloroethyl group, a 3,3,3-trifluoropropyl group, a 3,3,3-trichloropropyl group, a 2,2-difluoropropyl group, a 3,3-difluorobutyl group, a 1-bromo-2,2,2-trifluoroethyl group, a 1-chloro-2,2,2-trifluoroethyl group, a 1,2,2,2-tetrafluoroethyl group, a pentafluoroethyl group, 2,2,3,3,3-pentafluoropropyl group, a 1,1,2,2-tetrafluoroethyl group and 2,2,3,3-tetrafluoropropyl group;

a C2-C5 alkenyl group optionally substituted by at least one halogen atom includes, for example, a vinyl group, an allyl group, a 1-propenyl group, a 3-butenyl group, a 2-methyl-1-propenyl group, a 3-methyl-2-butenyl group, a 3-pentenyl group, a 4-pentenyl group, a 3-methyl-3-butenyl group, a 4-methyl-3-pentenyl group, a 1-chlorovinyl group, a 2-chlorovinyl group, a 1-fluorovinyl group, a 2-fluorovinyl group, a 2,2-dichlorovinyl group, a 2,2-dibromovinyl group, a 2,2-difluorovinyl group, a 1,2,2-trifluorovinyl group, a 1-(trifluoromethyl)vinyl group, a 2-chloro-2-propenyl, a 3-chloro-2-propenyl, a 2-fluoro-2-propenyl, a 3-fluoro-2-propenyl, a 3,3-dichloro-2-propenyl, a 3,3-dibromo-2-propenyl, a 3,3-difluoro-2-propenyl, a 2,3,3-trifluoro-2-propenyl group, a 2-(trifluoromethyl)-2-propenyl group, a 2,3,3,3-tetrafluoro-1-propenyl group, a 1,2,3,3,3-pentafluoro-1-propenyl group, a 3,4,4-trifluoro-3-butenyl group, a 3,4,4,4-tetrafluoro-2-butenyl group, a 2,3,4,4,4-pentafluoro-2-butenyl group and 4,5,5-trifluoro-4-pentenyl group;

a C2-C5 alkynyl group optionally substituted by at least one halogen atom includes, for example, an ethynyl group, a 1-propynyl group, a 2-propynyl group, a 1-butynyl group, a 3-methyl-1-butynyl group, a 2-chloro-1-propynyl group, a 3-chloro-2-propynyl group, a 3,3,3-trifluoro-1-propynyl group and a 4,4,4-trifluoro-2-butynyl group;

a C3-C5 cycloalkyl group optionally substituted by at least one halogen atom or at least one C1-C3 alkyl group includes, for example, a cyclopropyl group, a 2,2-dichlorocyclopropyl group, a 2,2-difluorocyclopropyl group, a 2,2,3,3-tetrafluorocyclopropyl group, a 2,2-dichlorocyclobutyl group, a 2,2-difluorocyclobutyl group, a 2,2,3,3-tetrafluorocyclobutyl group, a cyclobutyl group, a cyclopentyl group and a cyclohexyl group;

a C4-C5 cycloalkenyl group optionally substituted by at least one halogen atom includes, for example, 2-fluoro-2-cyclopentenyl group.

A C2-C6 alkanediyl group optionally substituted by at least one halogen atom represented by bonding of $R^3$ and $R^4$ includes, for example, an ethylene group, a propylene group, a trimethylene group and a tetramethylene group;

a C4-C6 alkenediyl group optionally substituted by at least one halogen atom represented includes, for example, a 2-butenylene group and 2-pentenylene group.

A halogen atom represented by $R^5$, $R^6$ and $R^{14}$ includes a fluorine atom, a chlorine atom, a bromine atom and an iodine atom.

A C1-C5 alkyl group optionally substituted by at least one halogen atom represented by $R^5$, $R^6$, $R^7$, $R^{10}$, $R^{11}$, $R^{12}$, $R^{13}$, $R^{14}$, $R^{17}$ and $R^{18}$ includes, for example, a methyl group, an ethyl group, a 1-methylethyl group, a 1-ethylethyl group, a 1,1-dimethylethyl group, a n-propyl group, a 1-methylpropyl group, a 1-ethylpropyl group, a 1,1-dimethylpropyl group, a 2,2-dimethylpropyl group, a 1,2-dimethylpropyl group, a 1,1,2-trimethylpropyl group, a n-butyl group, a 1-methylbutyl group, a 2-methylbutyl group, a 3-methylbutyl group, a n-pentyl group, a fluoromethyl group, a chloromethyl group, a bromomethyl group, a iodomethyl group, a difluoromethyl group, a chlorodifluoromethyl group, a bromodifluoromethyl group, a trifluoromethyl group, a dichloromethyl group, a trichloromethyl group, a 1-chloroethyl group, a 1-bromoethyl group, a 1-iodoethyl group, a 1-fluoroethyl group, a 2-chloroethyl group, a 2-bromoethyl group, a 2-iodoethyl group, a 2-fluoroethyl group, a 2,2-difluoroethyl group, a 2,2,2-trifluoroethyl group, a 2,2,2-trichloroethyl group, a pentafluoroethyl group, a 2,2,2-trifluoro-1-chloroethyl group, a 3-fluoropropyl group, a 3-chloropropyl group, a 1-fluoro-1-methylethyl group, a 1-chloro-1-methylethyl group, a 2-chloro-1,1-dimethylethyl group, a 2-fluoro-1,1-dimethylethyl group, a heptafluoropropyl group, a 1, 1,2,2,3,3-hexafluoro-n-propyl group, a 4-chlorobutyl group, a 4-fluorobutyl group, a 5-chloropentyl group and 5-fluoropentyl group.

A C2-C5 alkenyl group optionally substituted by at least one halogen atom represented by $R^5$ or $R^6$ includes, for example, a vinyl group, a 1-methylvinyl group, a 1-propenyl group, a 1-methyl-1-propenyl group, a 2-methyl-1-propenyl group, a 1,2-dimethyl-1-propenyl group, a 2-propenyl group, a 1-methyl-2-propenyl group, a 2-methyl-2-propenyl group, a 1,1-dimethyl-2-propenyl group, a 1,2-dimethyl-2-propenyl group and a 2,2-difluorovinyl group, a 2-chloro-2-propenyl group, a 2,2-dichloro-2-propenyl group, a 2-bromo-2-propenyl group, a 2,2-dibromo-2-propenyl group, a 2-fluoro-2-propenyl group and a 2,2-difluoro-2-propenyl group.

A C3-C5 alkenyl group optionally substituted by at least one halogen atom represented by $R^7$, $R^{10}$, $R^{11}$, $R^{12}$, $R^{13}$, $R^{17}$ and $R^{18}$ includes, for example, a 1-methylvinyl group, a 1-propenyl group, a 1-methyl-1-propenyl group, a 2-methyl-1-propenyl group, a 1,2-dimethyl-1-propenyl group, a 2-propenyl group, a 1-methyl-2-propenyl group, a 2-methyl-2-propenyl group, a 1, 1-dimethyl-2-propenyl group, a 1,2-dimethyl-2-propenyl group, a 2-chloro-2-propenyl group, a 2,2-dichloro-2-propenyl group, a 2-bromo-2-propenyl group, a 2,2-dibromo-2-propenyl group, a 2-fluoro-2-propenyl group and a 2,2-difluoro-2-propenyl group.

A C2-C5 alkynyl group optionally substituted by at least one halogen atom represented by $R^5$ and $R^6$ includes, for example, an ethynyl group, a 1-propynyl group, a 2-propynyl group and a 3,3,3-trifluoro-1-propynyl group.

A C3-C5 alkynyl group optionally substituted by at least one halogen atom represented by $R^7$, $R^{10}$, $R^{11}$, $R^{11}$, $R^{12}$, $R^{13}$, $R^{17}$, $R^{18}$ includes, for example, a 1-propynyl group, a 2-propynyl group and a 3,3,3-trifluoro-1-propynyl group.

A C3-C6 cycloalkyl group optionally substituted by at least one halogen atom or at least one C1-C3 alkyl group represented by $R^5$, $R^6$, $R^7$, $R^{10}$, $R^{11}$, $R^{12}$, $R^{13}$, $R^{14}$, $R^{17}$ and $R^{18}$ includes, for example, a cyclopropyl group, a 1-methylcyclopropyl group, a 2,2-dichlorocyclopropyl group, a 2,2-dichloro-1-methylcyclopropyl group, a 2,2-difluorocyclopropyl group, a 2,2-difluoro-1-methylcyclopropyl group, a cyclobutyl group, a cyclopentyl group and a cyclohexyl group.

A C1-C5 alkoxy group optionally substituted by at least one halogen atom represented by $R^5$, $R^6$ and $R^{14}$ includes, for example, a methoxy group, an ethoxy group, a propoxy group, a trifluoromethoxy group, a bromodifluoromethoxy group, a difluoromethoxy group, a chlorodifluoromethoxy group, a pentafluoroethoxy group, a 2,2,2-trifluoroethoxy group and a 1,1,2,2-tetrafluoroethoxy group.

A C3-C6 alkenyloxy group optionally substituted by at least one halogen atom represented by $R^5$ and $R^6$ includes, for example, a 1-propenyloxy group, a 2-propenyloxy group and 2,2-difluoro-2-propenyloxy group.

A C3-C6 alkynyloxy group optionally substituted by at least one halogen atom represented by $R^5$ and $R^6$ includes, for example, a 2-propynyloxy group, a 2-butynyloxy group and 3,3,3-trifluoro-1-propynyloxy group.

A (C1-C5 alkoxy group optionally substituted by at least one halogen atom) C1-C3alkyl group represented by $R^{10}$ and $R^{11}$ includes, for example, a methoxymethyl group, an ethoxymethyl group, a 1-methoxyethyl group, a 1-ethoxyethyl group and a trifluoromethoxymethyl group.

A C1-C5 alkylthio group optionally substituted by at least one halogen atom represented by $R^5$, $R^6$ and $R^{14}$ includes, for example, a methylthio group, an ethylthio group, a trifluoromethylthio group, a chlorodifluoromethylthio group, a bromodifluoromethylthio group, a dibromofluoromethylthio group, a 2,2,2-trifluoroethylthio group, a 1,1,2,2-tetrafluoroethylthio group and pentafluoroethylthio group.

A C3-C5 alkenylthio group optionally substituted by at least one halogen atom represented by $R^5$, $R^6$ and $R^{14}$ includes, for example, a 1-propenylthio group, a 2-propenylthio group and 2,2-difluoro-2-propenylthio group.

A C3-C5 alkynylthio group optionally substituted by at least one halogen atom represented by $R^5$, $R^6$ and $R^{14}$ includes, for example, a 2-propynylthio group, a 2-butynylthio group and 3,3,3-trifluoro-1-propynylthio group.

A C1-C5 alkylsulfinyl group optionally substituted by at least one halogen atom represented by $R^5$, $R^6$, $R^{10}$, $R^{11}$ and $R^{14}$ includes, for example, a methylsulfinyl group and a trifluoromethylsulfinyl group.

A C1-C5 alkylsulfonyl group optionally substituted by at least one halogen atom represented by $R^5$, $R^6$, $R^{10}$, $R^{11}$ and $R^{14}$ includes, for example, a methylsulfonyl group and a trifluoromethylsulfonyl group.

A C2-C6 alkylcarbonyl group optionally substituted by at least one halogen atom represented by $R^5$, $R^6$, $R^7$, $R^{10}$, $R^{11}$ and $R^{14}$ includes, for example, an acetyl group, a propionyl group, a 2,2-dimethylpropionyl group and a trifluoroacetyl group.

A C2-C5 alkoxycarbonyl group represented by $R^5$, $R^6$, $R^7$, $R^{10}$, $R^{11}$ and $R^{14}$ includes, for example, a methoxycarbonyl group, an ethoxycarbonyl group, a 1-methylethoxycarbonyl group and t-butoxycarbonyl group.

In case of the $R^5$ and $R^6$, which are bonded with the adjoined two atoms or the two $R^6$s, which are bonded with the adjoined two atoms, are coupled one another at the end thereof, a C2-C6 alkanediyl group optionally substituted by at least one halogen atom represented by $R^5$ and $R^6$ includes, for example, a propylene group, a trimethylene group and a tetramethylene group; a C4-C6 alkenediyl group optionally substituted by at least one halogen atom includes, for example, a 2-butenylene group and a 2-pentenylene group.

A C2-C6 alkanediyl group optionally substituted by at least one halogen atom represented by combination of $R^{12}$ and $R^{13}$ includes, for example, an ethylene group, a propylene group, a trimethylene group and a tetramethylene group; a C4-C6 alkenediyl group optionally substituted by at least one halogen atom includes, for example, a 2-butenylene group and a 2-pentenylene group.

Aspects of the compound of the present invention include, for example, the following compounds:

a malononitrile compound of the formula (I) in which $R^1$ is a hydrogen atom;

a malononitrile compound of the formula (I) in which $R^2$ is a methyl group;

a malononitrile compound of the formula (I) in which $R^1$ and $R^2$ are hydrogen atoms;

a malononitrile compound of the formula (I) in which $R^1$ is a hydrogen atom and $R^2$ is a methyl group;

a malononitrile compound of the formula (I) in which $R^3$ is a hydrogen atom;

a malononitrile compound of the formula (I) in which $R^4$ is a C2-C5 alkenyl group optionally substituted by at least one halogen atom;

a malononitrile compound of the formula (I) in which $R^4$ is a vinyl group;

a malononitrile compound of the formula (I) in which $R^4$ is a 2-propenyl group;

a malononitrile compound of the formula (I) in which $R^4$ is a 2,2-difluorovinyl group;

a malononitrile compound of the formula (I) in which $R^4$ is a 1-(trifluoromethyl)vinyl group;

a malononitrile compound of the formula (I) in which $R^4$ is a 3,3-difluoro-2-propenyl group;

a malononitrile compound of the formula (I) in which $R^4$ is a 2,3,3-trifluoro-2-propenyl group;

a malononitrile compound of the formula (I) in which $R^4$ is a 3,3,3-trifluoro-1-propenyl group;

a malononitrile compound of the formula (I) in which $R^4$ is a C2-C5 haloalkynyl group optionally substituted by at least one halogen atom;

a malononitrile compound of the formula (I) in which $R^4$ is a C1-C5 fluoroalkyl group;

a malononitrile compound of the formula (I) in which $R^4$ is a fluoromethyl group;

a malononitrile compound of the formula (I) in which $R^4$ is a 2,2-difluoroethyl group;

a malononitrile compound of the formula (I) in which $R^4$ is a 2,2,2-trifluoroethyl group;

a malononitrile compound of the formula (I) in which $R^4$ is a pentafluoroethyl group;

a malononitrile compound of the formula (I) in which $R^4$ is a 3,3,3-trifluoropropyl group;

a malononitrile compound of the formula (I) in which $R^4$ is a 2,2,3,3,3-pentafluoropropyl group;

a malononitrile compound of the formula (I) in which $R^4$ is a C3-C6 cycloalkyl group;

a malononitrile compound of the formula (I) in which $R^4$ is a 2,2-dichlorocyclopropyl group;

a malononitrile compound of the formula (I) in which $R^4$ is a cyclopropyl group;

a malononitrile compound of the formula (I) in which $R^4$ is a cyclobutyl group;

a malononitrile compound of the formula (I) in which $R^3$ is a hydrogen atom and $R^4$ is a vinyl group or a 2-propenyl group;

a malononitrile compound of the formula (I) in which $R^3$ is a hydrogen atom and $R^4$ is a 2,2-difluorovinyl group, 1-(trifluoromethyl)vinyl group, a 3,3-difluoro-2-propenyl group, 2,3,3-trifluoro-2-propenyl group or a 3,3,3-trifluoro-1-propenyl group;

a malononitrile compound of the formula (I) in which $R^3$ is a hydrogen atom and $R^4$ is a fluoromethyl group, a 2,2-difluoroethyl group, a 2,2,2-trifluoroethyl group, a 1,1,2,2,2-pentafluoroethyl group, a 3,3,3-trifluoropropyl group or a 2,2,3,3,3-pentafluoropropyl group;

a malononitrile compound of the formula (I) in which $R^3$ is a hydrogen atom and $R^4$ is a cyclopropyl group, a cyclobutyl group or a 2,2-dichlorocyclopropyl group;

a malononitrile compound of the formula (I) in which $R^1$, $R^2$ and $R^3$ are hydrogen atoms and $R^4$ is a vinyl group or a 2-propenyl group;

a malononitrile compound of the formula (I) in which $R^1$, $R^2$ and $R^3$ are hydrogen atoms and $R^4$ is a 2,2-difluorovinyl group, a 1-(trifluoromethyl)vinyl group, a 3,3-difluoro-2-propenyl group, a 2,3,3-trifluoro-2-propenyl group or a 3,3,3-trifluoro-1-propenyl group;

a malononitrile compound of the formula (I) in which $R^1$ and $R^3$ are hydrogen atoms, $R^2$ is a methyl group, and $R^4$ is a 2,2-difluorovinyl group or 1-(trifluoromethyl)vinyl group, 3,3-difluoro-2-propenyl group, 2,3,3-trifluoro-2-propenyl group or a 3,3,3-trifluoro-1-propenyl group;

a malononitrile compound of the formula (I) in which $R^1$, $R^2$ and $R^3$ are hydrogen atoms and $R^4$ is a fluoromethyl group, a 2,2-difluoroethyl group, a 2,2,2-trifluoroethyl group, a pentafluoroethyl group, a 3,3,3-trifluoropropyl group or a 2,2,3,3,3-pentafluoropropyl group;

a malononitrile compound of the formula (I) in which $R^1$ and $R^3$ are hydrogen atoms, $R^2$ is a methyl group, and $R^4$ is a fluoromethyl group, a 2,2-difluoroethyl group, a 2,2,2-trifluoroethyl group, a pentafluoroethyl group, a 3,3,3-trifluoropropyl group or a 2,2,3,3,3-pentafluoropropyl group;

a malononitrile compound of the formula (I) in which $R^1$, $R^2$ and $R^3$ are hydrogen atoms and $R^4$ is a cyclopropyl group, a cyclobutyl group or a 2,2-dichlorocyclopropyl group;

a malononitrile compound of the formula (I) in which $X^1$, $X^2$ and $X^3$ are each $CR^6$;

a malononitrile compound of the formula (I) in which $X^1$ is a nitrogen atom, and $X^2$ and $X^3$ are each $CR^6$;

a malononitrile compound of the formula (I) in which $X^2$ is a nitrogen atom, and $X^1$ and $X^3$ are each $CR^6$;

a malononitrile compound of the formula (I) in which $X^3$ is a nitrogen atom, and $X^1$ and $X^2$ are each $CR^6$;

a malononitrile compound of the formula (I) in which $X^1$ and $X^2$ are nitrogen atoms, and $X^3$ is $CR^6$;

a malononitrile compound of the formula (I) in which $X^1$ and $X^3$ are nitrogen atoms, and $X^2$ is $CR^6$;

a malononitrile compound of the formula (I) in which $X^1$, $X^2$ and $X^3$ are nitrogen atoms;

a malononitrile compound of the formula (I) in which $X^3$ is $CR^6$, and the $R^6$ is a C1-C5 alkyl group optionally substituted by at least one halogen atom, a C2-C5 alkenyl group optionally substituted by a halogen atom(s), or a C2-C5 alkynyl group optionally substituted by at least one halogen atom;

a malononitrile compound of the formula (I) in which $X^3$ is $CR^6$, and the $R^6$ is an ethyl group;

a malononitrile compound of the formula (I) in which $X^3$ is $CR^6$, and the $R^6$ is a 1-methylethyl group;

a malononitrile compound of the formula (I) in which $X^3$ is $CR^6$, and the $R^6$ is a 1,1-dimethylethyl group;

a malononitrile compound of the formula (I) in which $X^3$ is $CR^6$, and the $R^6$ is a 2,2-dimethylpropyl group;

a malononitrile compound of the formula (I) in which $X^3$ is $CR^6$, and the $R^6$ is a trifluoromethyl group;

a malononitrile compound of the formula (I) in which $X^3$ is $CR^6$, and the $R^6$ is a pentafluoroethyl group;

a malononitrile compound of the formula (I) in which $X^3$ is $CR^6$, and the $R^6$ is a 1-methylvinyl group;

a malononitrile compound of the formula (I) in which $X^3$ is $CR^6$, and the $R^6$ is an ethynyl group;

a malononitrile compound of the formula (I) in which $X^3$ is $CR^6$, and the $R^6$ is a C3-C6 cycloalkyl group optionally substituted by at least one halogen atom;

a malononitrile compound of the formula (I) in which $X^3$ is CR 6, and the $R^6$ is a cyclopropyl group;

a malononitrile compound of the formula (I) in which $X^3$ is $CR^6$, and the $R^6$ is a 1-methylcyclopropyl group;

a malononitrile compound of the formula (I) in which $X^3$ is $CR^6$, and the $R^6$ is a C1-C5 alkoxy group optionally substituted by at least one halogen atom, a C3-C6 alkenyloxy group optionally substituted by at least one halogen atom, or a C3-C6 alkynyloxy group optionally substituted by at least one halogen atom;

a malononitrile compound of the formula (I) in which $X^3$ is $CR^6$, and the $R^6$ is a propargyloxy group;

a malononitrile compound of the formula (I) in which $X^3$ is $CR^6$, and the $R^6$ is a 2-butynyloxy group;

a malononitrile compound of the formula (I) in which $X^3$ is $CR^6$, and the $R^6$ is a 3-butynyloxy group;

a malononitrile compound of the formula (I) in which $X^3$ is $CR^6$, and the $R^6$ is a C1-C5 alkylthio group optionally substituted by at least one halogen atom, a C1-C5 alkylsulfinyl group optionally substituted by a halogen atom(s), or a C1-5 alkylsulfonyl group optionally substituted by at least one halogen atom;

a malononitrile compound of the formula (I) in which $X^3$ is $CR^6$, and the $R^6$ is a methylthio group;

a malononitrile compound of the formula (I) in which $X^3$ is $CR^6$, and the $R^6$ is a trifluoromethylthio group;

a malononitrile compound of the formula (I) in which $X^3$ is $CR^6$, and the $R^6$ is a propargylthio group;

a malononitrile compound of the formula (I) in which $X^3$ is $CR^6$, and the $R^6$ is a methylsulfinyl group;

a malononitrile compound of the formula (I) in which $X^3$ is $CR^6$, and the $R^6$ is a trifluoromethylslfinyl group;

a malononitrile compound of the formula (I) in which $X^3$ is $CR^6$, and the $R^6$ is a methylsulfonyl group;

a malononitrile compound of the formula (I) in which $X^3$ is $CR^6$, and the $R^6$ is a cyano group;

a malononitrile compound of the formula (I) in which $X^3$ is $CR^6$, and the $R^6$ is a halogen atom;

a malononitrile compound of the formula (I) in which $X^3$ is $CR^6$, and the $R^6$ is a bromine atom;

a malononitrile compound of the formula (I) in which $X^3$ is $CR^6$, and the $R^5$ is a chlorine atom;

a malononitrile compound of the formula (I) in which $X^3$ is $CR^6$, and the $R^6$ is a fluorine atom;

a malononitrile compound of the formula (I) in which $X^3$ is $CR^6$, and the $R^6$ is a nitro group;

a malononitrile compound of the formula (I) in which $R^1$ is a hydrogen atom, and $R^2$ is a C1-C3 alkyl group optionally substituted by at least one halogen atom or a hydrogen atom;

a malononitrile compound of the formula (I) in which $R^1$ is a C1-C3 alkyl group optionally substituted by at least one halogen atom or a hydrogen atom or a hydrogen atom, and $R^2$ is a C1-C3 alkyl group optionally substituted by at least one halogen atom, a C1-C3 alkoxy group optionally substituted by at least one halogen atom, a C2-C5 alkenyl group optionally substituted by at least one halogen atom, a C2-C5 alkynyl group optionally substituted by at least one halogen atom, a cyano group or a hydrogen atom;

a malononitrile compound of the formula (I) in which each of $R^3$ and $R^4$ is a C1-C5 alkyl group optionally substituted by at least one halogen atom, a C2-C5 alkenyl group optionally substituted by at least one halogen atom, a C2-C5 alkynyl group optionally substituted by at least one halogen atom, a C3-C5 cycloalkyl group optionally substituted by at least one halogen atom or at least one C1-C3 alkyl group, or a C2-C6 alkanediyl group optionally substituted by at least one halogen atom in which $R^3$ and $R^4$ are coupled one another at the end thereof;

a malononitrile compound of the formula (I) in which $R^1$ is a hydrogen atom, $R^2$ is a C1-C3 alkyl group optionally substituted by at least one halogen atom or a hydrogen atom, each of $R^3$ and $R^4$ is a C1-C5 alkyl group optionally substituted by at least one halogen atom, a C2-C5 alkenyl group optionally substituted by at least one halogen atom, a C2-C5 alkynyl group optionally substituted by at least one halogen atom, a C3-C5 cycloalkyl group optionally substituted by at least one halogen atom or at least one C1-C3 alkyl group, or a C2-C6 alkanediyl group optionally substituted by at least one halogen atom in which $R^3$ and $R^4$ are coupled one another at the end thereof;

a malononitrile compound of the formula (I) in which $R^1$ is a C1-C3 alkyl group optionally substituted by at least one halogen atom or a hydrogen atom, $R^2$ is a C1-C3 alkyl group optionally substituted by at least one halogen atom, a C1-C3 alkoxy group optionally substituted by at least one halogen atom, a C2-C5 alkenyl group optionally substituted by at least one halogen atom, a C2-C5 alkynyl group optionally substituted by at least one halogen atom, a cyano group, or a hydrogen atom, each of $R^3$ and $R^4$ is a C1-C5 alkyl group optionally substituted by at least one halogen atom, a C2-C5 alkenyl group optionally substituted by at least one halogen atom, a C2-C5 alkynyl group optionally substituted by at least one halogen atom, a C3-C5 cycloalkyl group optionally substituted by at least one halogen atom or at least one C1-C3 alkyl group, or a C2-C6 alkanediyl group optionally substituted by at least one halogen atom in which $R^3$ and $R^4$ are coupled one another at the end thereof;

a malononitrile compound of the formula (I) in which $R^3$ is a hydrogen atom, $R^4$ is a C1-C5 alkyl group optionally substituted by at least one halogen atom, a C2-C5 alkenyl group optionally substituted by at least one halogen atom, a C2-C5 alkynyl group optionally substituted by at least one halogen atom, or a C2-C6 alkanediyl group in which $R^3$ and $R^4$ are coupled one another at the end thereof;

a malononitrile compound of the formula (I) in which $R^1$ is a hydrogen atom, $R^2$ is a C1-C5 alkyl group optionally substituted by at least one halogen atom or a hydrogen atom, $R^3$ is a hydrogen atom, $R^4$ is a C1-C3 alkyl group optionally substituted by at least one halogen atom, a C2-C5 alkenyl group optionally substituted by at least one halogen atom, a C2-C5 alkynyl group optionally substituted by at least one halogen atom, or a C2-C6 alkanediyl group in which $R^3$ and $R^4$ are coupled one another at the end thereof;

a malononitrile compound of the formula (I) in which $R^1$ is a C1-C3 alkyl group optionally substituted by at least one halogen atom or a hydrogen atom, $R^2$ is a C1-C3 alkyl group optionally substituted by at least one halogen atom, a C1-C3 alkoxy group optionally substituted by at least one halogen atom, a C2-C5 alkenyl group optionally substituted by at least one halogen atom, a C2-C5 alkynyl group optionally substituted by at least one halogen atom, a cyano group, or a hydrogen atom, $R^3$ is a hydrogen atom, $R^4$ is a C1-C5 alkyl group optionally substituted by at least one halogen atom, a C2-C5 alkenyl group optionally substituted by at least one halogen atom, a C2-C5 alkynyl group optionally substituted by at least one halogen atom, or a C2-C6 alkanediyl group in which $R^3$ and $R^4$ are coupled one another at the end thereof;

a malononitrile compound represented by the formula (I-1):

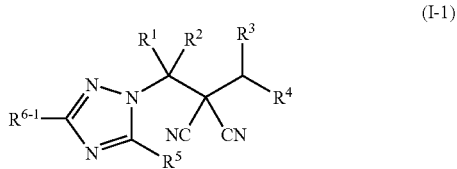

(I-1)

,wherein, in the formula, $R^1$ represents a C1-C5 alkyl group optionally substituted by at least one halogen atom, a C2-C5 alkenyl group optionally substituted by at least one halogen atom, a C2-C5 alkynyl group optionally substituted by at least one halogen atom or a hydrogen atom;

$R^2$ represents a C1-C5 alkyl group optionally substituted by at least one halogen atom, a C1-C5 alkoxy group optionally substituted by at least one halogen atom, a C2-C5 alkenyl group optionally substituted by at least one halogen atom, a C2-C5 alkynyl group optionally substituted by at least one halogen atom, a cyano group or a hydrogen atom;

each of $R^3$ and $R^4$ represents a C1-C5 alkyl group optionally substituted by at least one halogen atom, a C2-C5 alkenyl group optionally substituted by at least one halogen atom, a C2-C5 alkynyl group optionally substituted by at least one halogen atom, a C3-C5 cycloalkyl group optionally substituted by at least one halogen atom or at least one C1-C3 alkyl group, a C4-C5 cycloalkenyl group optionally substituted by at least one halogen atom or a hydrogen atom, or represents a C2-C6 alkanediyl group optionally substituted by at least one halogen atom or C4-C6 alkenediyl group optionally substituted by at least one halogen atom in which $R^3$ and $R^4$ are coupled one another at the end thereof;

each of $R^5$ and $R^{6-1}$ represents a halogen atom, a cyano group, a nitro group, a hydroxyl group, a mercapto group, a formyl group, a $SF_5$ group, a carboxyl group, a C1-C5 alkyl group optionally substituted by at least one halogen atom, a C2-C5 alkenyl group optionally substituted by at least one halogen atom, a C2-C5 alkynyl group optionally substituted by at least one halogen atom, a C3-C6 cycloalkyl group optionally substituted by at least one halogen atom or at least one C1-C3 alkyl group, a C1-C5 alkoxy group optionally substituted by at least one halogen atom, a C3-C6 alkenyloxy group optionally substituted by at least one halogen atom, a C3-C6 alkynyloxy group optionally substituted by at least one halogen atom, a C1-C5 alkylthio group optionally substituted by at least one halogen atom, a C3-C5 alkenylthio group optionally substituted by at least one halogen atom, a C3-C5 alkynylthio group optionally substituted by at least one halogen atom, a C1-C5 alkylsulfinyl group optionally substituted by at least one halogen atom, a C1-C5 alkylsulfonyl group optionally substituted by at least one halogen atom, a C2-C6 alkylcarbonyl group optionally substituted by at least one halogen atom, a C2-C5 alkoxy carbonyl group optionally substituted by at least one halogen atom, a phenyl group or a hydrogen atom;

a malononitrile compound of the formula (I-1) in which $R^1$ is a C1-C5 alkyl group optionally substituted by at least one halogen atom, a C2-C5 alkenyl group optionally substituted by at least one halogen atom, a C2-C5 alkynyl group optionally substituted by at least one halogen atom or a hydrogen atom;

$R^2$ is a C1-C5 alkyl group optionally substituted by at least one halogen atom, a C1-C5 alkoxy group optionally substituted by at least one halogen atom, a C2-C5 alkenyl group optionally substituted by at least one halogen atom, a C2-C5 alkynyl group optionally substituted by at least one halogen atom, a cyano group or a hydrogen atom;

each of $R^3$ and $R^4$ is a C1-C5 alkyl group optionally substituted by at least one halogen atom, a C2-C5 alkenyl group optionally substituted by at least one halogen atom, a C2-C5 alkynyl group optionally substituted by at least one halogen atom, a C3-C5 cycloalkyl group optionally substituted by at least one halogen atom or at least one C1-C3 alkyl group, a C4-C5 cycloalkenyl group optionally substituted by at least one halogen atom or a hydrogen atom, or represents a C2-C6 alkanediyl group optionally substituted by at least one halogen atom or C4-C6 alkenediyl group optionally substituted by at least one halogen atom in which $R^3$ and $R^4$ are coupled one another at the end thereof;

$R^5$ is a hydrogen atom;

and $R^{6-1}$ is a halogen atom, a C1-C5 alkyl group optionally substituted by at least one halogen atom, a C1-C5 alkoxy group optionally substituted by at least one halogen atom, a C1-C5 alkylthio group optionally substituted by at least one halogen atom or a hydrogen atom;

a malononitrile compound of the formula (I-1) in which $R^1$ is a C1-C5 alkyl group optionally substituted by at least one halogen atom, a C2-C5 alkenyl group optionally substituted by at least one halogen atom, a C2-C5 alkynyl group optionally substituted by at least one halogen atom or a hydrogen atom;

$R^2$ is a C1-C5 alkyl group optionally substituted by at least one halogen atom, a C1-C5 alkoxy group optionally substituted by at least one halogen atom, a C2-C5 alkenyl group optionally substituted by at least one halogen atom, a C2-C5 alkynyl group optionally substituted by at least one halogen atom, a cyano group or a hydrogen atom;

each of $R^3$ and $R^4$ is a C1-C5 alkyl group optionally substituted by at least one halogen atom, a C2-C5 alkenyl group optionally substituted by at least one halogen atom, a C2-C5 alkynyl group optionally substituted by at least one halogen atom, a C3-C5 cycloalkyl group optionally substituted by at least one halogen atom or at least one C1-C3 alkyl group, a C4-C5 cycloalkenyl group optionally substituted by at least one halogen atom or a hydrogen atom;

$R^5$ is a hydrogen atom;

and $R^{6-1}$ is a halogen atom, a C1-C5 alkyl group optionally substituted by at least one halogen atom, a C1-C5 alkoxy group optionally substituted by at least one halogen atom, a C1-C5 alkylthio group optionally substituted by at least one halogen atom or a hydrogen atom;

a malononitrile compound of the formula (I-1) in which $R^1$, $R^2$, $R^3$ and $R^5$ are hydrogen atoms;

$R^4$ is a C1-C5 alkyl group optionally substituted by at least one halogen atom or a C2-C5 alkenyl group optionally substituted by at least one halogen atom;

and $R^{6-1}$ is a halogen atom, a C1-C5 alkyl group optionally substituted by at least one halogen atom, a C1-C5 alkoxy group optionally substituted by at least one halogen atom, a C1-C5 alkylthio group optionally substituted by at least one halogen atom or a hydrogen atom;

a malononitrile compound of the formula (I-1) in which $R^1$, $R^2$, $R^3$ and $R^5$ are hydrogen atoms;

$R^4$ is a 2,2,2-trifluoromethyl group or a vinyl group;

and $R^{6-1}$ is a halogen atom, a C1-C5 alkyl group optionally substituted by at least one halogen atom, a C1-C5 alkoxy group optionally substituted by at least one halogen atom, a C1-C5 alkylthio group optionally substituted by at least one halogen atom or a hydrogen atom;

a malononitrile compound represented by the formula (I-2):

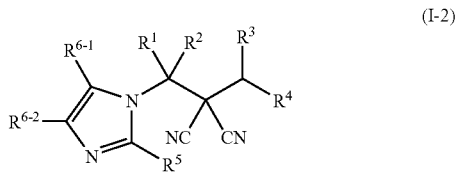

(I-2)

wherein, in the formula, $R^1$ represents a C1-C5 alkyl group optionally substituted by at least one halogen atom, a C2-C5 alkenyl group optionally substituted by at least one halogen atom, a C2-C5 alkynyl group optionally substituted by at least one halogen atom or a hydrogen atom;

$R^2$ represents a C1-C5 alkyl group optionally substituted by at least one halogen atom, a C1-C5 alkoxy group optionally substituted by at least one halogen atom, a C2-C5 alkenyl group optionally substituted by at least one halogen atom, a C2-C5 alkynyl group optionally substituted by at least one halogen atom, a cyano group or a hydrogen atom;

each of $R^3$ and $R^4$ represents a C1-C5 alkyl group optionally substituted by at least one halogen atom, a C2-C5 alkenyl group optionally substituted by at least one halogen atom, a C2-C5 alkynyl group optionally substituted by at least one halogen atom, a C3-C5 cycloalkyl group optionally substituted by at least one halogen atom or at least one C1-C3 alkyl group, a C4-C5 cycloalkenyl group optionally substituted by at least one halogen atom or a hydrogen atom, or represents a C2-C6 alkanediyl group optionally substituted by at least one halogen atom or C4-C6 alkenediyl group optionally substituted by at least one halogen atom in which $R^3$ and $R^4$ are coupled one another at the end thereof;

each of $R^5$, $R^{6-1}$ and $R^{6-2}$ represents a halogen atom, a cyano group, a nitro group, a hydroxyl group, a mercapto group, a formyl group, a $SF_5$ group, a carboxyl group, a C1-C5 alkyl group optionally substituted by at least one halogen atom, a C2-C5 alkenyl group optionally substituted by at least one halogen atom, a C2-C5 alkynyl group optionally substituted by at least one halogen atom, a C3-C6 cycloalkyl group optionally substituted by at least one halogen atom or at least one C1-C3 alkyl group, a C1-C5 alkoxy group optionally substituted by at least one halogen atom, a C3-C6 alkenyloxy group optionally substituted by at least one halogen atom, a C3-C6 alkynyloxy group optionally substituted by at least one halogen atom, a C1-C5 alkylthio group optionally substituted by at least one halogen atom, a C3-C5 alkenylthio group optionally substituted by at least one halogen atom, a C3-C5 alkynylthio group optionally substituted by at least one halogen atom, a C1-C5 alkylsulfinyl group optionally substituted by at least one halogen atom, a C1-C5 alkylsulfonyl group optionally substituted by at least one halogen atom, a C2-C6 alkylcarbonyl group optionally substituted by at least one halogen atom, a C2-C5 alkoxycarbonyl group optionally substituted by at least one halogen atom, a phenyl group or a hydrogen atom;

a malononitrile compound of the formula (I-2) in which $R^1$ is a C1-C5 alkyl group optionally substituted by at least one halogen atom, a C2-C5 alkenyl group optionally substituted by at least one halogen atom, a C2-C5 alkynyl group optionally substituted by at least one halogen atom or a hydrogen atom; $R^2$ is a C1-C5 alkyl group optionally substituted by at least one halogen atom, a C1-C5 alkoxy group optionally substituted by at least one halogen atom, a C2-C5 alkenyl group optionally substituted by at least one halogen atom, a C2-C5 alkynyl group optionally substituted by at least one halogen atom, a cyano group or a hydrogen atom;

each of $R^3$ and $R^4$ is a C1-C5 alkyl group optionally substituted by at least one halogen atom, a C2-C5 alkenyl group optionally substituted by at least one halogen atom, a C2-C5 alkynyl group optionally substituted by at least one halogen atom, a C3-C5 cycloalkyl group optionally substituted by at least one halogen atom or at least one C1-C3 alkyl group, a C4-C5 cycloalkenyl group optionally substituted by at least one halogen atom or a hydrogen atom, or represents a C2-C6 alkanediyl group optionally substituted by at least one halogen atom or C4-C6 alkenediyl group optionally substituted by at least one halogen atom in which $R^3$ and $R^4$ are coupled one another at the end thereof;

$R^5$ is a hydrogen atom;

and each of $R^{6-1}$ and $R^{6-2}$ is a halogen atom, a C1-C5 alkyl group optionally substituted by at least one halogen atom, a C1-C5 alkoxy group optionally substituted by at least one halogen atom, a C1-C5 alkylthio group optionally substituted by at least one halogen atom or a hydrogen atom;

a malononitrile compound of the formula (I-2) in which $R^1$ is a C1-C5 alkyl group optionally substituted by at least one halogen atom, a C2-C5 alkenyl group optionally substituted by at least one halogen atom, a C2-C5 alkynyl group optionally substituted by at least one halogen atom or a hydrogen atom;

$R^2$ is a C1-C5 alkyl group optionally substituted by at least one halogen atom, a C1-C5 alkoxy group optionally substituted by at least one halogen atom, a C2-C5 alkenyl group optionally substituted by at least one halogen atom, a C2-C5 alkynyl group optionally substituted by at least one halogen atom, a cyano group or a hydrogen atom;

each of $R^3$ and $R^4$ is a C1-C5 alkyl group optionally substituted by at least one halogen atom, a C2-C5 alkenyl group optionally substituted by at least one halogen atom, a C2-C5 alkynyl group optionally substituted by at least one halogen atom, a C3-C5 cycloalkyl group optionally substituted by at least one halogen atom or at least one C1-C3 alkyl group, a C4-C5 cycloalkenyl group optionally substituted by at least one halogen atom or a hydrogen atom;

$R^5$ is a hydrogen atom;

and each of $R^{6-1}$ and $R^{6-2}$ a halogen atom, a C1-C5 alkyl group optionally substituted by at least one halogen atom, a C1-C5 alkoxy group optionally substituted by at least one halogen atom, a C1-C5 alkylthio group optionally substituted by at least one halogen atom or a hydrogen atom;

a malononitrile compound of the formula (I-2) in which $R^1$, $R^2$, $R^3$ and $R^5$ are hydrogen atoms;

$R^4$ is a C1-C5 alkyl group optionally substituted by at least one halogen atom or a C2-C5 alkenyl group optionally substituted by at least one halogen atom;

and each of $R^{6-1}$ and $R^{6-2}$ is a halogen atom, a C1-C5 alkyl group optionally substituted by at least one halogen atom, a C1-C5 alkoxy group optionally substituted by at least one halogen atom, a C1-C5 alkylthio group optionally substituted by at least one halogen atom or a hydrogen atom;

a malononitrile compound of the formula (I-2) in which $R^1$, $R^2$, $R^3$ and $R^5$ are hydrogen atoms;

$R^4$ is a 2,2,2-trifluoromethyl group or a vinyl group;

and each of $R^{6-1}$ and $R^{6-2}$ a halogen atom, a C1-C5 alkyl group optionally substituted by at least one halogen atom, a C1-C5 alkoxy group optionally substituted by at least one halogen atom, a C1-C5 alkylthio group optionally substituted by at least one halogen atom or a hydrogen atom;

a malononitrile compound represented by the formula (I-3):

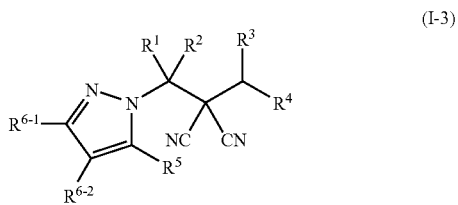

(I-3)

wherein, in the formula, $R^1$ represents a C1-C5 alkyl group optionally substituted by at least one halogen atom, a C2-C5 alkenyl group optionally substituted by at least one halogen atom, a C2-C5 alkynyl group optionally substituted by at least one halogen atom or a hydrogen atom;

$R^2$ represents a C1-C5 alkyl group optionally substituted by at least one halogen atom, a C1-C5 alkoxy group optionally substituted by at least one halogen atom, a C2-C5 alkenyl group optionally substituted by at least one halogen atom, a C2-C5 alkynyl group optionally substituted by at least one halogen atom, a cyano group or a hydrogen atom;

each of $R^3$ and $R^4$ represents a C1-C5 alkyl group optionally substituted by at least one halogen atom, a C2-C5 alkenyl group optionally substituted by at least one halogen atom, a C2-C5 alkynyl group optionally substituted by at least one halogen atom, a C3-C5 cycloalkyl group optionally substituted by at least one halogen atom or at least one C1-C3 alkyl group, a C4-C5 cycloalkenyl group optionally substituted by at least one halogen atom or a hydrogen atom, or represents a C2-C6 alkanediyl group optionally substituted by at least one halogen atom or C4-C6 alkenediyl group optionally substituted by at least one halogen atom in which $R^3$ and $R^4$ are coupled one another at the end thereof;

each of $R^5$, $R^{6-1}$ and $R^{6-2}$ represents a halogen atom, a cyano group, a nitro group, a hydroxyl group, a mercapto group, a formyl group, a $SF_5$ group, a carboxyl group, a C1-C5 alkyl group optionally substituted by at least one halogen atom, a C2-C5 alkenyl group optionally substituted by at least one halogen atom, a C2-C5 alkynyl group optionally substituted by at least one halogen atom, a C3-C6 cycloalkyl group optionally substituted by at least one halogen atom or at least one C1-C3 alkyl group, a C1-C5 alkoxy group optionally substituted by at least one halogen atom, a C3-C6 alkenyloxy group optionally substituted by at least one halogen atom, a C3-C6 alkynyloxy group optionally substituted by at least one halogen atom, a C1-C5 alkylthio group optionally substituted by at least one halogen atom, a C3-C5 alkenylthio group optionally substituted by at least one halogen atom, a C3-C5 alkynylthio group optionally substituted by at least one halogen atom, a C1-C5 alkylsulfinyl group optionally substituted by at least one halogen atom, a C1-C5 alkylsulfonyl group optionally substituted by at least one halogen atom, a C2-C6 alkylcarbonyl group optionally substituted by at least one halogen atom, a C2-C5 alkoxycarbonyl group optionally substituted by at least one halogen atom, a phenyl group or a hydrogen atom;

a malononitrile compound of the formula (I-3) in which $R^1$ is a C1-C5 alkyl group optionally substituted by at least one halogen atom, a C2-C5 alkenyl group optionally substituted by at least one halogen atom, a C2-C5 alkynyl group optionally substituted by at least one halogen atom or a hydrogen atom;

$R^2$ is a C1-C5 alkyl group optionally substituted by at least one halogen atom, a C1-C5 alkoxy group optionally substituted by at least one halogen atom, a C2-C5 alkenyl group optionally substituted by at least one halogen atom, a C2-C5 alkynyl group optionally substituted by at least one halogen atom, a cyano group or a hydrogen atom;

each of $R^3$ and $R^4$ is a C1-C5 alkyl group optionally substituted by at least one halogen atom, a C2-C5 alkenyl group optionally substituted by at least one halogen atom, a C2-C5 alkynyl group optionally substituted by at least one halogen atom, a C3-C5 cycloalkyl group optionally substituted by at least one halogen atom or at least one C1-C3 alkyl group, a C4-C5 cycloalkenyl group optionally substituted by at least one halogen atom or a hydrogen atom, or represents a C2-C6 alkanediyl group optionally substituted by at least one halogen atom or C4-C6 alkenediyl group optionally substituted by at least one halogen atom in which $R^3$ and $R^4$ are coupled one another at the end thereof;

$R^5$ is a hydrogen atom;

and each of $R^{6-1}$ and $R^{6-2}$ is a halogen atom, a C1-C5 alkyl group optionally substituted by at least one halogen atom, a C1-C5 alkoxy group optionally substituted by at least one halogen atom, a C1-C5 alkylthio group optionally substituted by at least one halogen atom or a hydrogen atom;

a malononitrile compound of the formula (I-3) in which $R^1$ is a C1-C5 alkyl group optionally substituted by at least one halogen atom, a C2-C5 alkenyl group optionally substituted by at least one halogen atom, a C2-C5 alkynyl group optionally substituted by at least one halogen atom or a hydrogen atom;

$R^2$ is a C1-C5 alkyl group optionally substituted by at least one halogen atom, a C1-C5 alkoxy group optionally substituted by at least one halogen atom, a C2-C5 alkenyl group optionally substituted by at least one halogen atom, a C2-C5 alkynyl group optionally substituted by at least one halogen atom, a cyano group or a hydrogen atom;

$R^5$ is a hydrogen atom;

each of $R^3$ and $R^4$ is a C1-C5 alkyl group optionally substituted by at least one halogen atom, a C2-C5 alkenyl group optionally substituted by at least one halogen atom, a C2-C5 alkynyl group optionally substituted by at least one halogen atom, a C3-C5 cycloalkyl group optionally substituted by at least one halogen atom or at least one C1-C3 alkyl group, a C4-C5 cycloalkenyl group optionally substituted by at least one halogen atom or a hydrogen atom;

and each of $R^{6-1}$ and $R^{6-2}$ a halogen atom, a C1-C5 alkyl group optionally substituted by at least one halogen atom, a C1-C5 alkoxy group optionally substituted by at least one halogen atom, a C1-C5 alkylthio group optionally substituted by at least one halogen atom or a hydrogen atom;

a malononitrile compound of the formula (I-3) in which $R^1$, $R^2$, $R^3$ and $R^5$ are hydrogen atoms;

$R^4$ is a C1-C5 alkyl group optionally substituted by at least one halogen atom or a C2-C5 alkenyl group optionally substituted by at least one halogen atom;

and each of $R^{6-1}$ and $R^{6-2}$ is a halogen atom, a C1-C5 alkyl group optionally substituted by at least one halogen atom, a C1-C5 alkoxy group optionally substituted by at least one halogen atom, a C1-C5 alkylthio group optionally substituted by at least one halogen atom or a hydrogen atom;

a malononitrile compound of the formula (I-3) in which $R^1$, $R^2$, $R^3$ and $R^5$ are hydrogen atoms;

$R^4$ is a C1-C5 alkyl group optionally substituted by at least one halogen atom or a C2-C5 alkenyl group optionally substituted by at least one halogen atom;

$R^{6-1}$ is a halogen atom, a C1-C5 alkyl group optionally substituted by at least one halogen atom, a C1-C5 alkoxy group optionally substituted by at least one halogen atom, a C1-C5 alkylthio group optionally substituted by at least one halogen atom or a hydrogen atom;

and $R^{6-2}$ is a halogen atom or a hydrogen atom;

a malononitrile compound of the formula (I-3) in which $R^1$, $R^2$, $R^3$ and $R^5$ are hydrogen atoms;

$R^4$ is a 2,2,2-trifluoromethyl group or a vinyl group;

and each of $R^{6-1}$ and $R^{6-2}$ a halogen atom, a C1-C5 alkyl group optionally substituted by at least one halogen atom, a C1-C5 alkoxy group optionally substituted by at least one halogen atom, a C1-C5 alkylthio group optionally substituted by at least one halogen atom or a hydrogen atom;

a malononitrile compound of the formula (I-3) in which $R^1$, $R^2$, $R^3$ and $R^5$ are hydrogen atoms;

$R^4$ is a 2,2,2-trifluoromethyl group or a vinyl group;

$R^{6-1}$ is a halogen atom, a C1-C5 alkyl group optionally substituted by at least one halogen atom, a C1-C5 alkoxy group optionally substituted by at least one halogen atom, a C1-C5 alkylthio group optionally substituted by at least one halogen atom or a hydrogen atom;

and $R^{6-2}$ is a halogen atom or a hydrogen atom;

a malononitrile compound represented by the formula (I-4):

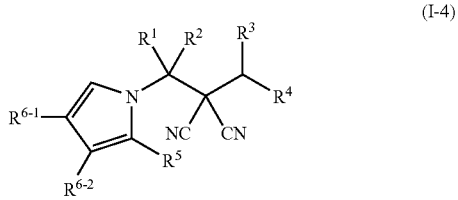

wherein, in the formula, $R^1$ represents a C1-C5 alkyl group optionally substituted by at least one halogen atom, a C2-C5 alkenyl group optionally substituted by at least one halogen atom, a C2-C5 alkynyl group optionally substituted by at least one halogen atom or a hydrogen atom;

$R^2$ represents a C1-C5 alkyl group optionally substituted by at least one halogen atom, a C1-C5 alkoxy group optionally substituted by at least one halogen atom, a C2-C5 alkenyl group optionally substituted by at least one halogen atom, a C2-C5 alkynyl group optionally substituted by at least one halogen atom, a cyano group or a hydrogen atom;

each of $R^3$ and $R^4$ represents a C1-C5 alkyl group optionally substituted by at least one halogen atom, a C2-C5 alkenyl group optionally substituted by at least one halogen atom, a C2-C5 alkynyl group optionally substituted by at least one halogen atom, a C3-C5 cycloalkyl group optionally substituted by at least one halogen atom or at least one C1-C3 alkyl group, a C4-C5 cycloalkenyl group optionally substituted by at least one halogen atom or a hydrogen atom, or represents a C2-C6 alkanediyl group optionally substituted by at least one halogen atom or C4-C6 alkenediyl group optionally substituted by at least one halogen atom in which $R^3$ and $R^4$ are coupled one another at the end thereof;

each of $R^5$, $R^{6-1}$ and $R^{6-2}$ represents a halogen atom, a cyano group, a nitro group, a hydroxyl group, a mercapto group, a formyl group, a $SF_5$ group, a carboxyl group, a C1-C5 alkyl group optionally substituted by at least one halogen atom, a C2-C5 alkenyl group optionally substituted by at least one halogen atom, a C2-C5 alkynyl group optionally substituted by at least one halogen atom, a C3-C6 cycloalkyl group optionally substituted by at least one halogen atom or at least one C1-C3 alkyl group, a C1-C5 alkoxy group optionally substituted by at least one halogen atom, a C3-C6 alkenyloxy group optionally substituted by at least one halogen atom, a C3-C6 alkynyloxy group optionally substituted by at least one halogen atom, a C1-C5 alkylthio group optionally substituted by at least one halogen atom, a C3-C5 alkenylthio group optionally substituted by at least one halogen atom, a C3-C5 alkynylthio group optionally substituted by at least one halogen atom, a C1-C5 alkylsulfinyl group optionally substituted by at least one halogen atom, a C1-C5 alkylsulfonyl group optionally substituted by at least one halogen atom, a C2-C6 alkylcarbonyl group optionally substituted by at least one halogen atom, a C2-C5 alkoxycarbonyl group optionally substituted by at least one halogen atom, a phenyl group or a hydrogen atom;

a malononitrile compound of the formula (I-4) in which $R^1$ is a C1-C5 alkyl group optionally substituted by at least one halogen atom, a C2-C5 alkenyl group optionally substituted by at least one halogen atom, a C2-C5 alkynyl group optionally substituted by at least one halogen atom or a hydrogen atom; $R^2$ is a C1-C5 alkyl group optionally substituted by at least one halogen atom, a C1-C5 alkoxy group optionally substituted by at least one halogen atom, a C2-C5 alkenyl group optionally substituted by at least one halogen atom, a C2-C5 alkynyl group optionally substituted by at least one halogen atom, a cyano group or a hydrogen atom;

each of $R^3$ and $R^4$ is a C1-C5 alkyl group optionally substituted by at least one halogen atom, a C2-C5 alkenyl group optionally substituted by at least one halogen atom, a C2-C5 alkynyl group optionally substituted by at least one halogen atom, a C3-C5 cycloalkyl group optionally substituted by at least one halogen atom or at least one C1-C3 alkyl group, a C4-C5 cycloalkenyl group optionally substituted by at least one halogen atom or a hydrogen atom, or represents a C2-C6 alkanediyl group optionally substituted by at least one halogen atom or C4-C6 alkenediyl group optionally substituted by at least one halogen atom in which $R^3$ and $R^4$ are coupled one another at the end thereof;

$R^5$ is a hydrogen atom;

and each of $R^{6-1}$ and $R^{6-2}$ is a halogen atom, a C1-C5 alkyl group optionally substituted by at least one halogen atom, a C1-C5 alkoxy group optionally substituted by at least one halogen atom, a C1-C5 alkylthio group optionally substituted by at least one halogen atom or a hydrogen atom;

a malononitrile compound of the formula (I-4) in which $R^1$ is a C1-C5 alkyl group optionally substituted by at least one halogen atom, a C2-C5 alkenyl group optionally substituted by at least one halogen atom, a C2-C5 alkynyl group optionally substituted by at least one halogen atom or a hydrogen atom;

$R^2$ is a C1-C5 alkyl group optionally substituted by at least one halogen atom, a C1-C5 alkoxy group optionally substituted by at least one halogen atom, a C2-C5 alkenyl group optionally substituted by at least one halogen atom, a C2-C5 alkynyl group optionally substituted by at least one halogen atom, a cyano group or a hydrogen atom;

each of $R^3$ and $R^4$ is a C1-C5 alkyl group optionally substituted by at least one halogen atom, a C2-C5 alkenyl group optionally substituted by at least one halogen atom, a C2-C5 alkynyl group optionally substituted by at least one halogen atom, a C3-C5 cycloalkyl group optionally substituted by at least one halogen atom or at least one C1-C3 alkyl group, a C4-C5 cycloalkenyl group optionally substituted by at least one halogen atom or a hydrogen atom;

$R^5$ is a hydrogen atom;

and each of $R^{6-1}$ and $R^{6-2}$ a halogen atom, a C1-C5 alkyl group optionally substituted by at least one halogen atom, a C1-C5 alkoxy group optionally substituted by at least one halogen atom, a C1-C5 alkylthio group optionally substituted by at least one halogen atom or a hydrogen atom;

a malononitrile compound of the formula (I-4) in which $R^1$, $R^2$, $R^3$ and $R^5$ are hydrogen atoms;

$R^4$ is a C1-C5 alkyl group optionally substituted by at least one halogen atom or a C2-C5 alkenyl group optionally substituted by at least one halogen atom;

and each of $R^{6-1}$ and $R^{6-2}$ is a halogen atom, a C1-C5 alkyl group optionally substituted by at least one halogen atom, a C1-C5 alkoxy group optionally substituted by at least one halogen atom, a C1-C5 alkylthio group optionally substituted by at least one halogen atom or a hydrogen atom;

a malononitrile compound of the formula (I-4) in which $R^1$, $R^2$, $R^3$ and $R^5$ are hydrogen atoms;

$R^4$ is a 2,2,2-trifluoromethyl group or a vinyl group;

and each of $R^{6-1}$ and $R^{6-2}$ a halogen atom, a C1-C5 alkyl group optionally substituted by at least one halogen atom, a C1-C5 alkoxy group optionally substituted by at least one halogen atom, a C1-C5 alkylthio group optionally substituted by at least one halogen atom or a hydrogen atom;

In the representation of the compounds of from the formula (I-1) to the formula (I-4) being represented by $R^{6-1}$ or $R^{6-2}$, a halogen atom includes, for example, a fluorine atom, a chlorine atom, and a bromine atom;

a C1-C5 alkyl group optionally substituted by at least one halogen atom includes, for example, a C1-C5 fluoroalkyl group such as a trifluoromethyl group, 2,2,2-trifluoroethyl group and the like and an alkyl group which is branched at 1-position such as an i-propyl group, a t-butyl group, a 1,1-dimethylpropyl group and the like;

a C1-C5 alkoxy group optionally substituted by at least one halogen atom includes, for example, a methoxy group, an ethoxy group, a 1-methylethoxy group and the like;

a C1-C5 alkylthio group optionally substituted by at least one halogen atom includes, for example, a methylthio group, an ethylthio group, a 1-methylethylthio group and the like.

Next, a method for producing the compound of the present invention is described.

The compound of the present invention can be produced, for example, according to the following (Production Method 1), (Production Method 2).

(Production Method 1)

A method to make react the compound (a) and the compound (b)

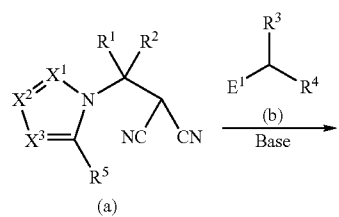

(a)

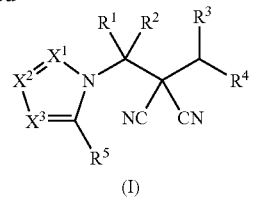

(I)

wherein, in the formula, $R^1$ represents a C1-C5 alkyl group optionally substituted by at least one halogen atom, a C2-C5 alkenyl group optionally substituted by at least one halogen atom, a C2-C5 alkynyl group optionally substituted by at least one halogen atom or a hydrogen atom;

$R^2$ represents a C1-C5 alkyl group optionally substituted by at least one halogen atom, a C1-C5 alkoxy group optionally substituted by at least one halogen atom, a C2-C5 alkenyl group optionally substituted by at least one halogen atom, a C2-C5 alkynyl group optionally substituted by at least one halogen atom, a cyano group or a hydrogen atom;

each of $R^3$ and $R^4$ represents a C1-C5 alkyl group optionally substituted by at least one halogen atom, a C2-C5 alkenyl group optionally substituted by at least one halogen atom, a C2-C5 alkynyl group optionally substituted by at least one halogen atom, a C3-C5 cycloalkyl group optionally substituted by at least one halogen atom or at least one C1-C3 alkyl group, a C4-C5 cycloalkenyl group optionally substituted by at least one halogen atom or a hydrogen atom, or represents a C2-C6 alkanediyl group optionally substituted by at least one halogen atom or C4-C6 alkenediyl group optionally substituted by at least one halogen atom in which $R^3$ and $R^4$ are coupled one another at the end thereof;

each of $X^1$, $X^2$ and $X^3$ represents a nitrogen atom or a $CR^6$;

each of $R^5$ and $R^6$ represents a halogen atom, a cyano group, a nitro group, a hydroxyl group, a mercapto group, a formyl group, a $SF_5$ group, a carboxyl group, a C1-C5 alkyl group optionally substituted by at least one halogen atom, a C2-C5 alkenyl group optionally substituted by at least one halogen atom, a C2-C5 alkynyl group optionally substituted by at least one halogen atom, a C3-C6 cycloalkyl group optionally substituted by at least one halogen atom or at least one C1-C3 alkyl group, a C1-C5 alkoxy group optionally substituted by at least one halogen atom, a C3-C6 alkenyloxy group optionally substituted by at least one halogen atom, a C3-C6 alkynyloxy group optionally substituted by at least one halogen atom, a C1-C5 alkylthio group optionally substituted by at least one halogen atom, a C3-C5 alkenylthio group optionally substituted by at least one halogen atom, a C3-C5 alkynylthio group optionally substituted by at least one halogen atom, a C1-C5 alkylsulfinyl group optionally substituted by at least one halogen atom, a C1-C5 alkylsulfonyl group optionally substituted by at least one halogen atom, a C2-C6 alkylcarbonyl group optionally substituted by at least one halogen atom, a C2-C5 alkoxycarbonyl group optionally substituted by at least one halogen atom, a group designated by $NR^{10}R^{11}$, a group designated by $C(=X^5)NR^{12}NR^{13}$, a group designated by $(CH_2)_mQ$, a group designated by $C(=NOR^{17})R^{18}$ or a hydrogen atom;

in case of two atoms are adjoined and each of the adjoined two atoms is bonded with one of $R^5$ and $R^6$ or two $R^6$s; the $R^5$ and $R^6$, which are bonded with the adjoined two atoms or the two R⁶s, which are bonded with the adjoined two atoms, maybe coupled one another at the end thereof and represent a C2-C6 alkanediyl group optionally substituted by at least one halogen atom or C4-C6 alkenediyl group. And in this case, at least one methylene group structuring said alkanediyl group or said alkenediyl group may be replaced by an oxygen atom a sulfur atom or NR⁷ group;

R⁷ represents a C1-C5 alkyl group optionally substituted by at least one halogen atom, a C3-C5 alkenyl group optionally substituted by at least one halogen atom, a C3-C5 alkynyl group optionally substituted by at least one halogen atom, a C3-C6 cycloalkyl group optionally substituted by at least one halogen atom or at least one C1-C3 alkyl group, a C2-C6 alkylcarbonyl group optionally substituted by at least one halogen atom, a C2-C5 alkoxycarbonyl group optionally substituted by at least one halogen atom or a hydrogen atom;

each of R¹⁰ and R¹¹ represents a C1-C5 alkyl group optionally substituted by at least one halogen atom, a C3-C5 alkenyl group optionally substituted by at least one halogen atom, a C3-C5 alkynyl group optionally substituted by at least one halogen atom, a C3-C6 cycloalkyl group optionally substituted by at least one halogen atom or at least one C1-C3 alkyl group, a (C1-C5 alkoxy group optionally substituted by at least one halogen atom) C1-C3 alkyl group, a C1-C5 alkylsulfinyl group optionally substituted by at least one halogen atom, a C1-C5 alkylsulfonyl group optionally substituted by at least one halogen atom, a C2-C6 alkylcarbonyl group optionally substituted by at least one halogen atom, a C2-C5 alkoxycarbonyl group optionally substituted by at least one halogen atom or a hydrogen atom;

each of R¹² and R¹³ represents a C1-C5 alkyl group optionally substituted by at least one halogen atom, a C3-C5 alkenyl group optionally substituted by at least one halogen atom, a C3-C5 alkynyl group optionally substituted by at least one halogen atom, a C3-C6 cycloalkyl group optionally substituted by at least one halogen atom or at least one C1-C3 alkyl group, a group designated by (CH₂)ₘQ or a hydrogen atom;

or represents a C2-C6 alkanediyl group optionally substituted by at least one halogen atom or C4-C6 alkenediyl group optionally substituted by at least one halogen atom in which R¹² and R¹³ are coupled one another at the end thereof;

each of R¹⁷ and R¹⁸ represents a C1-C5 alkyl group optionally substituted by at least one halogen atom, a C3-C5 alkenyl group optionally substituted by at least one halogen atom, a C3-C5 alkynyl group optionally substituted by at least one halogen atom, a C3-C6 cycloalkyl group optionally substituted by at least one halogen atom or at least one C1-C3 alkyl group, a group designated by (CH₂)ₘQ or a hydrogen atom;

Q represents an aryl group optionally substituted by at least one R¹⁴;

each of R¹⁴s represents a C1-C5 alkyl group optionally substituted by at least one halogen atom, a C3-C6 cycloalkyl group optionally substituted by at least one halogen atom or at least one C1-C3 alkyl group, a C1-C5 alkoxy group optionally substituted by at least one halogen atom, C1-C5 alkylthio group optionally substituted by at least one halogen atom, a C3-C5 alkenylthio group optionally substituted by at least one halogen atom, a C3-C5 alkynylthio group optionally substituted by at least one halogen atom, a C1-C5 alkylsulfinyl group optionally substituted by at least one halogen atom, a C1-C5 alkylsulfonyl group optionally substituted by at least halogen atom, C2-C6 alkylcarbonyl group optionally substituted by at least one halogen atom, C2-C5 alkoxycarbonyl group optionally substituted by at least one halogen atom or a halogen atom;

m represents an integer of from 0 to 5;

X⁵ represents an oxygen atom or a sulfur atom;

E¹ represents a leaving group such as a chlorine atom, a bromine atom, an iodine atom, a methanesulfonyl group, a trifluoromethanesulfonyl group, a toluenesulfonyl group, a methanesulfonyloxy group, a trifluoromethanesulfonyloxy group, and a toluenesulfonyloxy group and the like.

The reaction is usually carried out in a solvent and under the presence of a base.

The solvent used for the reaction includes, for example, acid amides such as N,N-dimethylformamide and the like, ethers such as diethylether, tetrahydrofuran and the like, organic sulfurs such as dimethylsulfoxide, sulfolane and the like, halogenated hydrocarbons such as 1,2-dichloroethane, chlorobenzene and the like, aromatic hydrocarbons such as toluene, xylene and the like, and mixtures thereof.

The base used for the reaction includes, for example, inorganic bases such as sodium hydride, sodium carbonate, potassium carbonate and the like, alkali metal alkoxides such as potassium-t-butoxide and the like, alkali metal amides such as lithium diisopropylamide and the like, and organic bases such as 4-(dimethylamino)pyridine, 1,4-diazabicyclo[2.2.2]octane, 1,8-diazabicyclo[5.4.0]-7-undecene and the like.

The amount of the base used for the reaction is usually 1 to 10 moles per 1 mole of the compound (a).

The amount of the compound (b) used for the reaction is usually 1 to 10 moles per 1 mole of the compound (a).

The reaction temperature of the reaction is usually in the range of −20 to 100° C., and the reaction time is usually in the range of 1 to 24 hours.

After the reaction has finished, the compound of the present invention represented by the formula (I) can be isolated by subjecting the reaction mixture to pose-treatment such as pouring the reaction mixture into water, extracting with an organic solvent, followed by concentrating the extract. The isolated the compound of the present invention represented by the formula (I) may be, if required, purified by chromatography, recrystallization and the like.

(Production Method 2)

A method to make react the compound (c) and the compound (d)

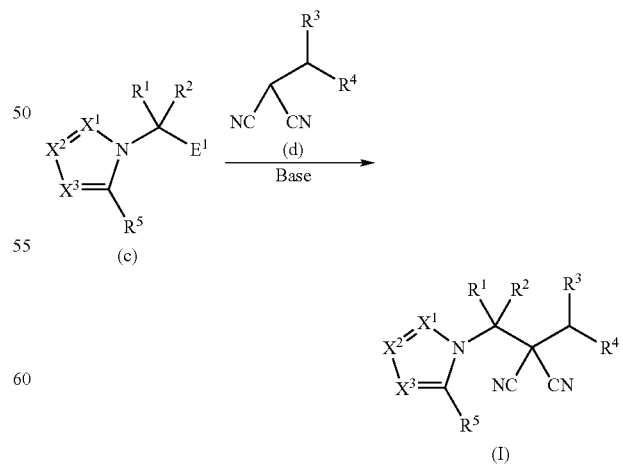

wherein, in the formula, E¹, R¹, R², R³, R⁴, R⁵, X¹, X² and X³ have the same meaning described above.

The reaction is usually carried out in a solvent and under the presence of a base.

The solvent used for the reaction includes, for example, acid amides such as N,N-dimethylformamide and the like, ethers such as diethylether, tetrahydrofuran and the like, organic sulfurs such as dimethylsulfoxide, sulfolane and the like, halogenated hydrocarbons such as 1,2-dichloroethane, chlorobenzene and the like, aromatic hydrocarbons such as toluene, xylene and the like, and mixtures thereof.

The base used for the reaction includes, for example, inorganic bases such as sodium hydride, sodium carbonate, potassium carbonate and the like, alkali metal alkoxides such as potassium-t-butoxide and the like, alkali metal amides such as lithium diisopropylamide and the like, and organic bases such as 4-dimethylaminopyridine, 1,4-diazabicyclo[2.2.2]octane, 1,8-diazabicyclo[5.4.0]-7-undecene and the like.

The amount of the base used for the reaction is usually 1 to 10 moles per 1 mole of the compound (c).

The amount of the compound (d) used for the reaction is usually 1 to 10 moles per 1 mole of the compound (c).

The reaction temperature of the reaction is usually in the range of −20 to 100° C., and the reaction time is usually in the range of 1 to 24 hours.

After the reaction has finished, the compound of the present invention represented by the formula (I) can be isolated by subjecting the reaction mixture to pose-treatment such as pouring the reaction mixture into water, extracting with an organic solvent, followed by concentrating the extract. The isolated the compound of the present invention represented by the formula (I) maybe, if required, purified by chromatography, recrystallization and the like.

Next, a method for producing the intermediate is described as Referential Production Method.

(Referential Production Method 1)

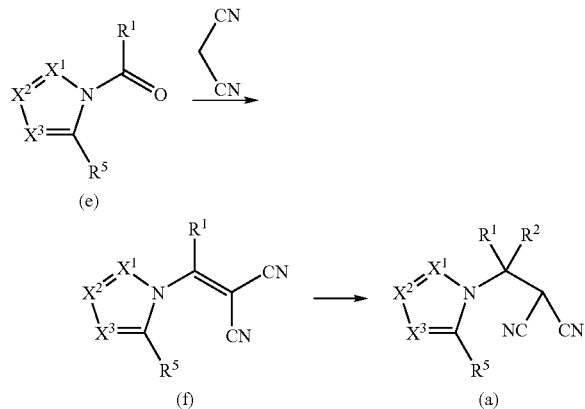

wherein, in the formula, $R^1$, $R^2$, $R^5$, $X^1$, $X^2$ and $X^3$ have the same meaning described above.

(First Step)

The compound (f) can be produced by making the compound (e) react with malononitrile.

The reaction is usually carried out in a solvent. The solvent used for the reaction includes, for example, acid amides such as N,N-dimethylformamide and the like, ethers such as diethylether, tetrahydrofuran and the like, halogenated hydrocarbons such as chloroform, 1,2-dichloroethane and the like, aromatic hydrocarbons such as toluene, xylene and the like, alcohols such as methanol, ethanol, isopropanol and the like and mixtures thereof.

The reaction is, if required, carried out under the presence of a base, and the base used for the reaction includes, for example, tetrabutylammonium hydroxide and the like.

The amount of the base used for the reaction is usually 0.01 to 0.5 moles per 1 mole of the compound (e).

The amount of malononitrile used for the reaction is usually 1 to 10 moles per 1 mole of the compound (e).

The reaction temperature of the reaction is usually in the range of −20 to 100° C., and the reaction time is usually in the range of 1 to 24 hours.

The reaction may be, if required, performed along with removing the water generated by the reaction out of the reaction system.

After the reaction has finished, the compound (f) can be isolated by subjecting the reaction mixture to pose-treatment such as pouring the reaction mixture into water, extracting with an organic solvent, followed by concentrating the extract. The isolated compound (f) may be, if required, purified by chromatography, recrystallization and the like.

(Second Step)

(1) In case that $R^2$ represents a C1-C5 alkyl group optionally substituted by at least one halogen atom, a C2-C5 alkenyl group optionally substituted by at least one halogen atom, or a alkenyl group optionally substituted by at least one halogen atom.

The compound (a) can be produced by subjecting the compound (f) to reaction with an organometallic compound.

The reaction is usually carried out in a solvent.

The solvent used for the reaction includes, for example, ethers such as diethylether, tetrahydrofuran and the like, aromatic hydrocarbons such as toluene, xylene and the like, and mixtures thereof.

The organo metallic compound used for the reaction includes, for example, organic magnesium compounds such as methyl magnesium iodide, ethyl magnesium bromide, isopropyl magnesium bromide, vinyl magnesium bromide, ethynyl magnesium bromide, dimethyl magnesium and the like, organic lithium compounds such as methyl lithium and the like, organic zinc compounds such as diethyl zinc and the like, and organic copper compound such as trifluoromethyl copper and the like.

The amount of the organometallic compound used for the reaction is usually 1 to 10 mole of the compound (f).

The reaction may be, if required, carried out under the presence of a copper salt. The copper salt used for the reaction includes, for example, copper iodide(I), copper bromide(I) and the like. The amount of the copper salt used for the reaction is usually 0.05 to 1 mole per 1 mole of the compound (f).

The reaction temperature of the reaction is usually in the range of −20 to 100° C., and the reaction time is usually in the range of 1 to 24 hours.

After the reaction has finished, the compound (a) can be isolated by subjecting the reaction mixture to pose-treatment such as pouring the reaction mixture into water, extracting with an organic solvent, followed by concentrating the extract. The isolated compound (a) may be, if required, purified by chromatography, recrystallization and the like.

(2) In case that $R^2$ represents a hydrogen atom.

The compound (a) can be produced by subjecting the compound (f) to reductive reaction.

The reduction reaction is usually carried out in a solvent.

The solvent used for the reaction includes, for example, ethers such as diethylether, tetrahydrofuran and the like, aromatic hydrocarbons such as toluene, xylene and the like, alcohols such as methanol, ethanol, propanol and the like, water and mixtures thereof.

The reducing agent used for the reaction includes, for example, sodium borohydride.

The amount of the reducing agent used for the reaction is usually 0.25 to 2 moles per 1 mole of the compound (f).

The reaction temperature of the reaction is usually in the range of 0 to 50° C., and the reaction time is usually in the range of the instant to 24 hours.

After the reaction has finished, the compound (a) can be isolated by subjecting the reaction mixture to pose-treatment such as pouring the reaction mixture into water, extracting with an organic solvent, followed by concentrating the extract. The isolated compound (a) may be, if required, purified by chromatography, recrystallization and the like.

(3) In case that $R^2$ represents a cyano group.

The compound (a) can be produced by subjecting the compound (f) to reaction with a cyanide compound.

The reaction is usually carried out in a solvent.

The solvent used for the reaction includes, for example, ethers such as diethylether, tetrahydrofuran and the like, aromatic hydrocarbons such as toluene, xylene and the like, and the mixture thereof.

The cyanide compound used for the reaction includes, for example, tetrabutylammonium cyanide.

The amount of the cyanide compound used for the reaction is usually 1 to 10 moles per 1 mole of the compound (f).

The reaction temperature of the reaction is usually in the range of −20 to 100° C., and the reaction time is usually in the range of 1 to 24 hours.

After the reaction has finished, the compound (a) can be isolated by subjecting the reaction mixture to pose-treatment such as pouring the reaction mixture into water, extracting with an organic solvent, followed by concentrating the extract. The isolated compound (a) may be, if required, purified by chromatography, recrystallization and the like.

(Referential Production Method 2)

The compound (d) can be produced by subjecting the compound (b) to reaction with malononitrile.

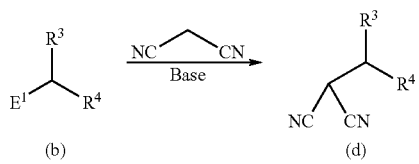

wherein, in the formula, $E^1$, $R^3$ and $R^4$ have the same meaning described above.

The reaction is usually carried out in a solvent and under the presence of a base.

The solvent used for the reaction includes, for example, acid amides such as N,N-dimethylformamide and the like, ethers such as diethylether, tetrahydrofuran and the like, organic sulfurs such as dimethylsulfoxide, sulfolane and the like, halogenated hydrocarbons such as 1,2-dichloroethane, chlorobenzene and the like, aromatic hydrocarbons such as toluene, xylene and the like and the like and mixtures thereof.

The base used for the reaction includes, for example, inorganic bases such as sodium hydride, sodium carbonate, potassium carbonate and the like, alkali metal alkoxides such as potassium-t-butoxide and the like, alkali metal amide such as lithium diisopropylamide and the like, and organic bases such as dimethylaminopyridine, 1,4-diazabicyclo[2.2.2]octane, 1,8-diazabicyclo[5.4.0]-7-undecene and the like.

The amount of the base used for the reaction is usually 1 to 10 moles per 1 mole of the compound (b).

The amount of malononitrile used for the reaction is usually 1 to 10 moles per 1 mole of the compound (b).

The reaction temperature of the reaction is usually in the range of −20 to 100° C., and the reaction time is usually in the range of 1 to 24 hours.

After the reaction has finished, the compound (d) can be isolated by subjecting the reaction mixture to pose-treatment such as pouring the reaction mixture into water, extracting with an organic solvent, followed by concentrating the extract. The isolated compound (d) may be, if required, purified by chromatography, recrystallization and the like.

(Referential Production Method 3)

The compound (d) can also be produced by following method.

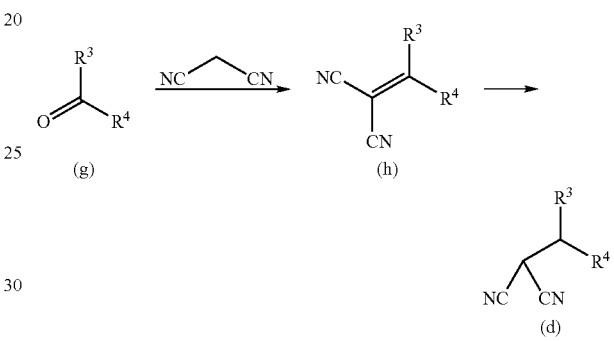

wherein, in the formula, $R^3$ and $R^4$ have the same meaning described above.

(First Step)

The compound (h) can be produced by making the compound (g) react with malononitrile.

The reaction is usually carried out in a solvent. The solvent used for the reaction includes, for example, acid amides such as N,N-dimethylformamide and the like, ethers such as diethylether, tetrahydrofuran and the like, halogenated hydrocarbons such as chloroform, 1,2-dichloroethane, chlorobenzene and the like, aromatic hydrocarbons such as toluene, xylene and the like, alcohols such as methanol, ethanol, isopropanol and the like and mixtures thereof.

The reaction is, if required, carried out under the presence of a base. The base used for the reaction includes, for example, tetrabutylammonium hydroxide and the like.

The amount of the base used for the reaction is usually 0.01 to 0.5 moles per 1 mole of the compound (g).

The amount of malononitrile used for the reaction is usually 1 to 10 moles per 1 mole of the compound (g).

The reaction temperature of the reaction is usually in the range of −20 to 100° C., and the reaction time is usually in the range of 1 to 24 hours.

The reaction may be, if required, performed along with removing the water generated by the reaction out of the reaction system.

After the reaction has finished, the compound (h) can be isolated by subjecting the reaction mixture to pose-treatment such as pouring the reaction mixture into water, extracting with an organic solvent, followed by concentrating the extract. The isolated compound (h) may be, if required, purified by chromatography, recrystallization and the like.

(Second Step)

The compound (d) can be produced by subjecting the compound (h) to reaction with reducing agent.

The reaction is usually carried out in a solvent.

The solvent used for the reaction includes, for example, alcohols such as methanol, ethanol, isopropyl alcohol, t-butyl alcohol and the like, ethers such as diethylether, tetrahydrofuran and the like, halogenated hydrocarbons such as 1,2-dichloroethane, chlorobenzene and the like, aromatic hydrocarbons such as toluene, xylene and the like, and mixtures thereof.

The reducing agent used for the reaction includes, for example, sodium borohydride, lithium borohydride, diisobutylalminum hydride and the like.

The amount of the reducing agent used for the reaction is, depend on the kind of the reducing agent used for the reaction, usually 0.25 to 5 moles per 1 mole of the compound (h).

The reaction temperature of the reaction is usually in the range of −20 to 100° C., and the reaction time is usually in the range of 1 to 24 hours.

After the reaction has finished, the compound (d) can be isolated by subjecting the reaction mixture to pose-treatment such as pouring the reaction mixture into water, extracting with an organic solvent, followed by concentrating the extract. The isolated compound (d) may be, if required, purified by chromatography, recrystallization and the like.

(Referential Production Method 4)

The compound (c-1) which $R^2$ is a hydrogen atom in the compound (c) can be produced by following method.

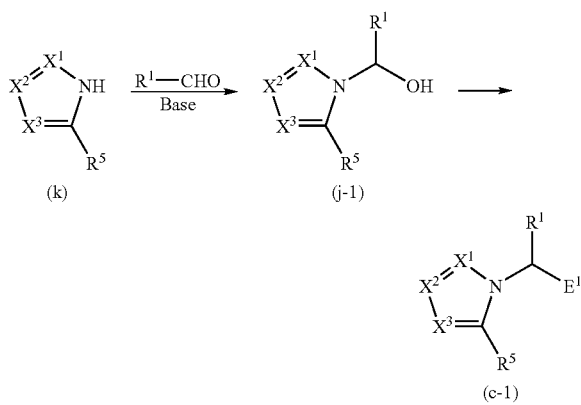

wherein, in the formula, $E^1$, $R^1$, $R^5$, $X^1$, $X^2$ and $X^3$ have the same meaning described above.

(First Step)

The compound (j-1) can be produced by subjecting the compound (k) to reaction with $R^1$—CHO.

The reaction is carried out under the presence or absence of a solvent. In case that the reaction is carried out under the presence of a solvent, the solvent to be used for the reaction includes, for example, aromatic hydrocarbons such as toluene, benzene and the like, halogenated hydrocarbons such as chlorobenzene and the like and mixtures thereof.

The reaction is carried out, if required, under the presence of a base. In case that the reaction is carried out under the presence of a base, the base used for the reaction includes, for example, organic bases such as triethylamine, ethyldiisopropylamine and the like, and the amount of the base used for the reaction is usually 0.5 to 5 moles per 1 mole of the compound (k).

The amount of $R^1$—CHO used for the reaction is usually 1 to 10 moles per 1 mole of the compound (k).

The reaction temperature of the reaction is usually in the range of 50 to 150° C., and the reaction time is usually in the range of 1 to 24 hours.

After the reaction has finished, the compound (j-1) can be isolated by subjecting the reaction mixture to pose-treatment such as adding an organic solvent including acetone to the reaction mixture, if required, and filtering the reaction mixture, then concentrating the filterate. The isolated compound (j-1) may be, if required, purified by chromatography, recrystallization and the like.

(Second Step)

The compound (c-1) can be produced by subjecting the compound (j-1) to halogenation such as subjecting the compound (j-1) to react with halogenating agent such as thionyl chloride, phosphorous oxychloride and the like; or to sulfonyl esterization such as subjecting the compound (j-1) to react with sulfonyl anhydride or sulfonyl chloride such as trifluoromethansulfonic anhydride, methansulfonyl chloride, toluensulfonyl chloride and the like.

Among the compound (c), (e), (k) and (j-1), the compound in which $X^1$, $X^2$ and $X^3$ are $CR^6$s can be synthesized according to the method disclosed in Houben-Weyl, Methoden der Organischen Chemi, Hetarene I, Teil.1, p.556-779.

Among the compound (c), (e), (k) and (j-1), the compound in which $X^1$ is a nitrogen atom and $X^2$ and $X^3$ are nitrogen atoms can be synthesized according to the method disclosed in Houben-Weyl, Methoden der Organischen Chemi, Hetarene III, Teil.3, p. 399-710.

Among the compound (c), (e), (k) and (j-1), the compound in which $X^2$ is a nitrogen atom and $X^1$ and $X^3$ are $CR^6$s can be synthesized according to the method disclosed in Houben-Weyl, Methoden der Organischen Chemi, Hetarene III, Teil.3, p. 1-192.

Among the compound (c), (e), (k) and (j-1), the compound in which $X^1$ and $X^2$ are nitrogen atoms and $X^3$ is $CR^6$ can be synthesized according to the method disclosed in Houben-Weyl, Methoden der Organischen Chemi, Hetarene III, Teil.4, p. 305-389.

Among the compound (c), (e), (k) and (j-1), the compound in which $X^1$ and $X^3$ are nitrogen atoms and $X^2$ is $CR^6$ can be synthesized according to the method disclosed in Houben-Weyl, Methoden der Organischen Chemi, Hetarene III, Teil.4, p. 479-586.

Among the compound (c), (e), (k) and (j-1), the compound in which $X^1$, $X^2$ and $X^3$ are nitrogen atoms can be synthesized according to the method disclosed in Houben-Weyl, Methoden der Organischen Chemi, Hetarene III, Teil.4, p. 664-777.

The pests against which the compound of the present invention has control activity may include, for example, arthropod pests such as insect pests and acarine pests and the like, and nematode pests. Specific examples are listed below:

Hemiptera:

Delphacidae such as *Laodelphax striatellus, Nilaparvata lugens, Sogatella furcifera* and the like, Deltocephalidae such as *Nephotettix cincticeps, Nephotettix virescens* and the like, Aphididae such as *Aphis gossypii, Myzus persicae* and the like, Pentatomidae such as *Nezara antennata, Riptortus clavetus, Eysarcoris lewisi, Eysarcoris parvus, Plautia stali, Halyomorpha mista* and the like, Aleyrodidae such as *Trialeurodes vaporariorum, Bemisia argentifolii* and the like, Coccidae such as *Aonidiella aurantii, Comstockaspis perniciosa, Unaspis citri, Ceroplastes rubens, Icerya purchasi* and the like,
Tingidae,
Psyllidae, and the like;
Lepidoptera:
Pyralidae such as *Chilo suppressalis, Cnaphalocrocis medinalis, Notarcha derogata, Plodia interpunctella* and the like,
Noctuidae such as *Spodoptera litura, Pseudaletia separata, Thoricoplusia* spp., *Heliothis* spp., *Helicoverpa* spp. and the like,
Pieridae such as *Pieris rapae* and the like,
Tortricidae such as *Adoxophyes* spp., *Grapholita molesta, Cydia pomonella* and the like,
Carposinidae such as *Carposina niponensis* and the like,
Lyonetiidae such as *Lyonetia* spp. and the like,
Lymantriidae such as *Lymantria* spp., *Euproctis* spp., and the like,
Yponomeutidae such as *Plutella xylostella* and the like,
Gelechiidae such as *Pectinophora gossypiella* and the like,
Arctiidae such as *Hyphantria cunea* and the like,
Tineidae such as *Tinea translucens, Tineola bisselliella* and the like;
Diptera:
Calicidae such as *Culex pipiens pallens, Culex tritaeniorhynchus, Culex quinquefasciatus* and the like,
*Aedes* spp. such as *Aedes aegypti, Aedes albopictus* and the like,
*Anopheles* spp. such as *Anopheles sinensis* and the like,
Chironomidae,
Muscidae such as *Musca domestica, Muscina stabulans* and the like,
Calliphoridae,
Sarcophagidae,
Fanniidae,
Anthomyiidae such as *Delia platura, Delia antiqua* and the like,
Tephritidae,
Drosophilidae,
Psychodidae,
Tabanidae,
Simuliidae,
Stomoxyidae,
Agromyzidae, and the like;
Coleoptera:
*Diabrotica* spp. such as *Diabrotica virgifera virgifera, Diabrotica undecimpunctata howardi* and the like,
Scarabaeidae such as *Anomala cuprea, Anomala rufocuprea* and the like,
Curculionidae such as *Sitophilus zeamais, Lissorhoptrus oryzophilus, Callosobruchuys chienensis* and the like,
Tenebrionidae such as *Tenebrio molitor, Tribolium castaneum* and the like,
Chrysomelidae such as *Oulema oryzae, Aulacophora femoralis, Phyllotreta striolata, Leptinotarsa decemlineata* and the like,
Anobiidae,
*Epilachna* spp. such as *Epilachna vigintioctopunctata* and the like,
Lyctidae,
Bostrychidae,
Cerambycidae,
*Paederus fuscipes*;
Blattodea: *Blattella germanica, Periplaneta fuliginosa, Periplaneta americana, Periplaneta brunnea, Blatta orientalis* and the like;

Thysanoptera: *Thrips palmi, Thrips tabaci, Frankliniella occidentalis, Frankliniella intonsa* and the like;
Hymenoptera: Formicidae, Vespidae, bethylid wasp, Tenthredinidae such as *Athalia japonica,* and the like;
Orthoptera: Gryllotalpidae, Acrididae, and the like;
Aphaniptera: *Ctenocephalides felis, Ctenocephalides canis, Pulex irritans, Xenopsylla cheopis,* and the like;
Anoplura: *Pediculus humanus corporis, Phthirus pubis, Haematopinus eurysternus, Dalmalinia ovis,* and the like;
Isoptera: *Reticulitermes speratus, Coptotermes formosanus,* and the like;
Acarina:
Tetranychidae such as *Tetranychus urticae, Tetranychus kanzawai, Panonychus citri, Panonychus ulmi, Oligonychus* spp., and the like,
Eriophyidae such as *Aculops pelekassi, Aculus schlechtendali,* and the like,
Tarsonemidae such as *Polyphagotarsonemus latus,* and the like,
Tenuipalpidae,
Tuckerellidae,
Ixodidae such as *Haemaphysalis longicornis, Haemaphysalis flava, Dermacentor taiwanicus, Ixodes ovatus, Ixodes persulcatus, Boophilus microplus,* and the like,
Acaridae such as *Tyrophagus putrescentiae,* and the like,
Epidermoptidae such as *Dermatophagoides farinae, Dermatophagoides ptrenyssnus,* and the like,
Cheyletidae such as *Cheyletus eruditus, Cheyletus malaccensis, Cheyletus moorei,* and the like,
Dermanyssidae;
Araneae: *Chiracanthium japonicum, Latrodectus hasseltii,* and the like;
Chilopoda: *Thereuonema hilgendorfi, Scolopendra subspinipes,* and the like;
Diplopoda: *Oxidus gracilis, Nedyopus tambanus,* and the like;
Isopoda: *Armadillidium vulgare,* and the like;
Gastropoda: *Limax marginatus, Limax flavus,* and the like;
Nematoda: *Pratylenchus coffeae, Pratylenchus fallax, Heterodera glycines, Globodera rostochiensis, Meloidogyne hapla, Meloidogyne incognita,* and the like.

The pesticide composition of the present invention contains an effective amount of the compound of the present invention and an inert carrier. Generally, it is a formulation obtained by mixing the compound of the present invention and a carrier such as a solid carrier, a liquid carrier and/or a gaseous carrier, and if necessary, adding a surfactant and other adjuvant for formulation. The formulation includes, for example, an emulsifiable concentrate, an oil solution, a shampoo formulation, a flowable, a dust, a wettable powder, a granule, a paste formulation, a microcapsule, a foam, an aerosol, a carbon dioxide gas formulation, a tablet and a resin formulation. These formulations maybe converted to use into a poison bait, a mosqito coil, an electric mosquito mat, a smoking agent, a fumigant or sheet.

In the pesticide composition of the present invention, the compound of the present invention is usually contained in an amount of 0.1% to 95% by weight.

The solid carrier for formulation includes, for example, a fine power and a granule of clays (e.g., kaolin clay, diatomite, bentonite, Fubasami clay, acid clay, etc.), synthetic hydrated silicon oxide, talc, ceramic, other inorganic minerals (e.g., sericite, quartz, sulfur, activated carbon, calcium carbonate, hydrated silica) or chemical fertilizers (e.g., ammonium sulfate, ammonium phosphate, ammonium nitrate, ammonium chloride, urea).

The liquid carrier for formulation includes, for example, aromatic or aliphatic hydrocarbons (e.g., xylene, toluene, alkylnaphthalene, phenylxylylethane, kerosine, light oil, hexane, cyclohexane), halogenated hydrocarbons (e.g., chlorobenzene, dichloromethane, dichloroethane, trichloroethane), alcohols (e.g., methanol, ethanol, isopropyl alcohol, butanol, hexanol, ethylene glycol), ethers (e.g., diethyl ether, ethylene glycol dimethyl ether, diethylene glycol monomethyl ether, diethylene glycol monoethyl ether, propylene glycolmonomethyl ether, tetrahydrofuran, dioxane), esters (e.g., ethyl acetate, butyl acetate), ketones (e.g., acetone, methyl ethyl ketone, methyl isobutyl ketone, cyclohexanone), nitriles (e.g., acetonitrile, isobutyronitrile), sulfoxides (e.g., dimethylsulfoxide), acid amides (e.g., N,N-dimethylformamide, N,N-dimethylacetamide), vegetable oils (e.g., soy bean oil, cotton seed oil), vegetable essential oils (e.g., orange oil, hyssop oil, lemon oil) and water.

The gaseous carrier for formulation includes, for example, butane gas, chlorofluorocarbons, liquefied petroleum gas (LPG), dimethyl ether, carbon dioxide and the like.

The surfactant includes, for example, alkyl sulfate salts, alkylsulfonic acid salts, alkylarylsulfonic acid salts, alkyl aryl ethers and their polyoxyethylene derivatives, polyethylene glycol ethers, polyhydric alcohol esters, and sugar alcohol derivatives.

The other adjuvant for formulation includes, binders, dispersants, stabilizers and the like, and specifically for example, casein, gelatin, polysaccharides (e.g., starch, gum arabic, cellulose derivatives, alginic acid), lignin derivatives, bentonite, sugars, synthetic water-soluble polymers (e.g., polyvinyl alcohol, polyvinylpyrrolidone, polyacrylic acid), PAP (isopropyl acid phosphate), BHT (2,6-di-t-butyl-4-methylphenol), BHA (a mixture of 2-t-butyl-4-methoxyphenol and 3-t-butyl-4-methoxyphenol), vegetable oils, mineral oils, fatty acids, and fatty acid esters.

The base for resin formulation includes, for example, polyvinyl chloride based copolymer, polyurethane and the like. To these bases, if necessary, a plasticizer such as phthalates (e.g., dimethyl phthalate, dioctyl phthalate), adipates and stearates may be added. The resin formulation can be obtained by kneading the compound into the base using a known kneader and then formulating by injection molding, extrusion molding, press molding and the like, and further, if necessary, via a process for molding, cutting and the like, the resin formulation can be converted into a resin formulation such as board, film, tape, net, string and the like. These resin formulations can be converted into, for example, an animal collar, an animal ear tag, a sheet formulation, an attraction string, a gardening stick.

A base for the poison bait includes, for example, grain powders, vegetable oils, sugars, and crystalline cellulose, and further, if necessary, antioxidants such as dibutylhydroxytoluene and nordihydroguaiaretic acid, preservatives such as dehydroacetic acid, agents for preventing children and pets from erroneously eating such as hot pepper powder, and pest-attractive flavors such as cheese flavor, onion flavor and peanut oil may be added to the base.

Pests can be controlled by applying an effective amount of the compound of the present invention to pests directly and/or habitats of pests (e.g., plant, animal, soil). Usually the formulation of the pesticide composition of the present invention is used as the method for controlling pests of the present invention.

When the pesticide composition of the present invention is used for a control of pests in agriculture and forestry, the application amount is usually 1 to 10,000 g/ha, preferably 10 to 1,000 g/ha, as an active ingredient. The emulsifiable concentrates, wettable powders, flowables, and microcapsule formulations are usually applied after dilution with water to have an active ingredient concentration of 1 to 10,000 ppm, while dusts and granules are usually applied as such. These formulations may be sprayed directly to the plant to be protected from pests. The pests living in the soil can be controlled by treating the soil with these formulations, and the formulations can also be applied to treat seedbeds prior to the planting plants or to treat planting holes or plant bottoms in the planting. Furthermore, the sheet formulation of the pesticide composition of the present invention can be applied by a method such as winding around plants, stretching in the vicinity of plants and laying on the soil surface at the plant bottom.

When the pesticide composition of the present invention is used for a control of epidemic, the application amount is usually 0.001 to 10 $mg/m^3$ as an active ingredient in case of application for open space, and 0.001 to 100 $mg/m^2$ as an active ingredient in case of application for plane surface. The emulsifiable concentrates, wettable powders, flowables, and microcapsule formulations are usually applied after dilution with water to have an active ingredient concentration of 0.01 to 10,000 ppm, while oil solutions, aerosols, smoking agents and poison baits are usually applied as such.

When the pesticide composition of the present invention is used for a control of parasite living outside of a livestock such as caw, horse, pig, sheep, goat and chicken, and a small animal such as dog, cat, rat and mouse, the pesticide composition can be applied to said animal by a veterinarily known method. Specifically, for systemic control, the pesticide composition is administered by means of, for example, a tablet, a mixture with feed, a suppository or an injection (e.g., intramuscular, subcutaneous, intravenous, intraperitoneal), and for non-systemic control, it is applied by a method such as spraying an oil solution or an aqueous liquid formulation, carrying out pour-on treatment or spot-on treatment, washing said animal with a shampoo formulation, attaching the resin formulation on said animal as a collar or an ear-tag, and the like. When the compound of the present invention is administered to an animal, its amount is usually in the range of 0.1 to 1,000 mg/kg body weight of the animal.

The pesticide composition of the present invention can also be used in admixture or combination with other insecticides, nematocides, acaricides, fungicides, herbicides, plant growth regulators, synergists, fertilizers, soil conditioners, animal feeds, and the like.

The active ingredients of such other insecticide and acaricide include, for example, pyrethroid compounds such as allethrin, tetramethrin, prallethrin, phenothrin, resmethrin, cyphenothrin, permethrin, cypermethrin, alpha-cypermethrin, zeta-cypermethrin, deltamethrin, tralomethrin, cyfluthrin, beta-cyfluthrin, cyhalothrin, lambda-cyhalothrin, flumethrin, imiprothrin, etofenprox, fenvalerate, esfenvalerate, fenpropathrin, silafluofen, bifenthrin, transfluthrin, flucythrinate, tau-fluvalinate, acrinathrin and tefluthrin; organophosphorus compounds such as dichlorvos, fenitrothion, cyanophos, profenofos, sulprofos, phenthoate, isoxathion, tetrachlorvinphos, fenthion, chlorpyriphos, diazinon, acephate, terbufos, phorate, chlorethoxyfos, fosthiazate, ethoprophos, cadusafos andmethidathion; carbamate compounds such aspropoxur, carbaryl, metoxadiazone, fenobucarb, methomyl, thiodicarb, alanycarb, benfuracarb, oxamyl, aldicarb and methiocarb; benzoylphenylurea compounds such as lufenuron, chlorfluazuron, hexaflumuron, diflubenzuron, triflumuron, teflubenzuron, flufenoxuron, fluazuron, novaluron and triazuron; juvenile hormone-like substances such as pyriproxyfen, methoprene, hydroprene and fenoxycarb; neonicotinoid compounds such as acetamiprid, nitenpyram, thiacloprid, thiamethoxam and dinotefuran; N-phenylpyrazole compounds such as acetoprole and ethiprole; benzoylhydrazine compounds such as tebufenozide, chromafenozide, methoxyfenozide and halofenozide; diafenthiuron; pymetrozine; flonicamid; triazamate; buprofezin; spinosad; emamectin benzoate; chlorfenapyr; indoxacarb MP; pyridalyl; cyromazine; fenpyroximate; tebufenpyrad; tolfenpyrad; pyridaben; pyrimidifen; fluacrypyrim; etoxazole; fenazaquin; acequinocyl; hexythiazox; clofentezine; fenbutatin oxide; dicofol, propargite; abamectin; milbemectin; amitraz; cartap; bensultap; thiocyclam; endosulfan; spirodiclofen; spiromesifen; and azadirachtin.

The active ingredients of such other fungicide include, for example, strobilurin compounds such as azoxystrobin; organophosphorus compounds such as tolclofos-methyl; azole compounds such as triflumizole, pefurazoate and difenoconazole; phthalide; flutolanil; validamycin; probenazole; diclomezine; pencycuron; dazomet; kasugamycin; IBP; pyroquilon; oxolinic acid; tricyclazole; ferimzone; mepronil; EDDP; isoprothiolane; carpropamid; diclocymet; furametpyr; fludioxonil; procymidone; and diethofencarb.

EXAMPLES

The present invention is constructed in more detail by production examples, formulation examples, test examples and the like, but should not be limited thereto.

Firstly, production examples of the compound of the present invention are illustrated.

Production Example 1

0.76 g of 1-(chloromethyl)-1H-pyrazole hydrochloride and 0.81 g of (3,3,3-trifluoropropyl)malononitrile were dissolved in 10 ml of N,N-dimethylformamide. 1.38 g of potassium carbonate was added to the solution under ice cooling with stirring, followed by stirring at room temperature for 5 hours. Water was added to the reaction mixture, and then extracted with methyl-t-butyl ether (may be referred as MTBE, hereinafter). The organic layer was washed with water, dried over anhydrous magnesium sulfate, filtered, and concentrated under reduced pressure. The residue was recrystallized from hexane-ethyl acetate to obtain 0.36 g of (1H-pyrazole-1-yl methyl) (3,3,3-trifluoropropyl) malononitrile (referred as the compound of the present invention (1), hereinafter) shown by below formula.

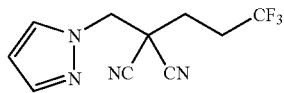

$^1$H-NMR(CDCl$_3$,TMS,δ(ppm)):2.21-2.27(2H,m),2.47-2.59(2H,m),4.76(2H,s),6.42(1H,t),7.63-7.64(2H,m)

Production Example 2

0.77 g of 3-i-propyl-1-(chloromethyl)-1H-pyrazole hydrochloride and 0.64 g of (3,3,3-trifluoropropyl)malononitrile were dissolved in 8 ml of N,N-dimethylformamide. 1.54 g of potassium carbonate was added to the solution under ice cooling with stirring, followed by stirring at room temperature for overnight. Water was added to the reaction mixture, and then extracted with MTBE. The organic layer was washed with water, dried over anhydrous magnesium sulfate, filtered, and concentrated under reduced pressure. The residue was subjected to silica gel column chromatography, and then recrystallized from hexane-ethyl acetate to obtain 0.42 g of [(3-i-propyl-1H-pyrazole-1-yl)methyl](3,3,3-trifluoropropyl) malononitrile (referred as the compound of the present invention (2), hereinafter) shown by below formula.

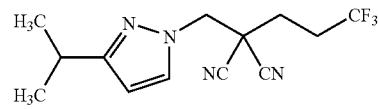

$^1$H-NMR(CDCl$_3$,TMS,δ(ppm)):1.24(6H,d),2.20-2.24(2H,m),2.47-2.58(2H,m),2.93-3.00(1H,m),4.34(2H,s),6.20(1H,d),7.50(1H,d)

Production Example 3

1.16 g of 3-t-butyl-1-(chloromethyl)-1H-pyrazole hydrochloride and 0.98 g of (3,3,3-trifluoropropyl)malononitrile were dissolved in 17 ml of N,N-dimethylformamide. 1.54 g of potassium carbonate was added to the solution under ice cooling with stirring, followed by stirring at room temperature for overnight. Water was added to the reaction mixture, and then extracted with MTBE. The organic layer was washed with water, dried over anhydrous magnesium sulfate, filtered, and concentrated under reduced pressure. The residue was subjected to silica gel column chromatography to obtain 0.63 g of [(3-t-butyl-1H-pyrazole-1-yl)methyl](3,3,3-trifluoropropyl) malononitrile (referred as the compound of the present invention (3), hereinafter) shown by below formula.

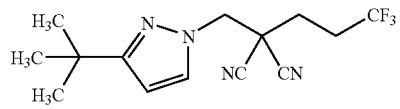

$^1$H-NMR(CDCl$_3$,TMS,δ(ppm)):1.28(9H,s),2.19-2.24(2H,m),2.48-2.57(2H,m),4.64(2H,s),6.23(1H,d),7.49(1H,d)

Production Example 4

1.24 g of 3-t-butyl-1-(chloromethyl)-1H-pyrazole hydrochloride and 0.63 g of allyl malononitrile were dissolved in 18 ml of N,N-dimethylformamide. 1.63 g of potassium carbonate was added to the solution, followed by stirring at room temperature for overnight. Water was added to the reaction mixture, and then extracted with MTBE. The organic layer was washed with water, dried over anhydrous magnesium sulfate, filtered, and concentrated under reduced pressure. The residue was subjected to silica gel column chromatography to obtain 0.38 g of allyl [(3-t-butyl-1H-pyrazole-1-yl)methyl]malononitrile (referred as the compound of the present invention (4), hereinafter) shown by below formula.

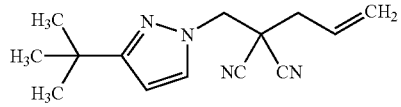

$^1$H-NMR(CDCl$_3$,TMS,δ(ppm)):1.30(9H,s),2.69(2H,dd),4.58(2H,s),5.45-5.51(2H,m),5.88-5.99(1H,m),6.21(1H,d),7.48(1H,d)

Production Example 5

0.58 g of 2-(chloromethyl)-6,6-dimethyl-2,4,5,6-tetrahydrocyclopenta[c]pyrazole hydrochloride and 0.43 g of (3,3, 3-trifluoropropyl) malononitrile were dissolved in 8 ml of N,N-dimethylformamide. 0.73 g of potassium carbonate was added to the solution under ice cooling with stirring, followed by stirring at room temperature for overnight. Water was added to the reaction mixture, and then extracted with MTBE. The organic layer was washed with water, dried over anhydrous magnesium sulfate, filtered, and concentrated under reduced pressure. The residue was subjected to silica gel column chromatography to obtain 0.27 g of [(6,6-dimethyl-5,6-dihydro-cyclopenta[c]pyrazole-2(4H)-yl)methyl](3,3,3-trifluoropropyl) malononitrile (referred as the compound of the present invention (5), hereinafter) shown by below formula.

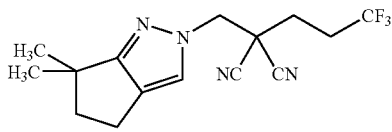

$^1$H-NMR(CDCl$_3$,TMS,δ(ppm)):1.24(6H,s),2.15-2.23 (4H,m),2.42-2.65(4H,m),5.97(2H,s),7.15(1H,s)

Production Example 6

1.44 g of 1-(chloromethyl)-3-(trifluoromethyl)-1H-pyrazole and 1.30 g of (3,3,3-trifluoropropyl) malononitrile were dissolved in 16 ml of N,N-dimethylformamide. 2.21 g of potassium carbonate was added to the solution under ice cooling with stirring, followed by stirring at room temperature for overnight. Water was added to the reaction mixture, and then extracted with MTBE. The organic layer was washed with water, dried over anhydrous magnesium sulfate, filtered, and concentrated under reduced pressure. The residue was recrystallized from hexane-ethyl acetate to obtain 0.87 g of {[3-(trifluoromethyl)-1H-pyrazole-1-yl]methyl}(3,3,3-trifluoropropyl) malononitrile (referred as the compound of the present invention (6), hereinafter) shown by below formula.

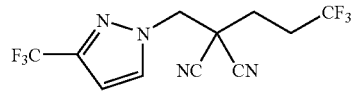

$^1$H-NMR(CDCl$_3$,TMS,δ(ppm)):2.25-2.29(2H,m),2.50-2.61(2H,m),4.75(2H,s),6.70(1H,s),7.72(1H,s)

Production Example 7

1.33 g of 1-(chloromethyl)-3-(trifluoromethyl)-1H-pyrazole and 0.76 g of allyl malononitrile were dissolved in 21 ml of N,N-dimethylformamide. 1.99 g of potassium carbonate was added to the solution under ice cooling with stirring, followed by stirring at room temperature for overnight. Water was added to the reaction mixture, and then extracted with MTBE. The organic layer was washed with water, dried over anhydrous magnesium sulfate, filtered, and concentrated under reduced pressure. The residue was recrystallized from hexane-ethyl acetate to obtain 0.57 g of allyl {[3-(trifluoromethyl)-1H-pyrazole-1-yl]methyl}malononitrile (referred as the compound of the present invention (7), hereinafter) shown by below formula.

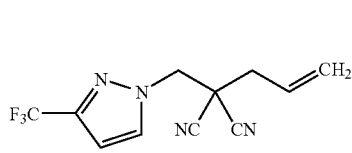

$^1$H-NMR(CDCl$_3$,TMS,δ(ppm)):2.74(2H,d),4.69(2H,s), 5.49-5.54(2H, m),5.87-5.98(1H,m),6.67(1H,s),7.71(1H,s)

Production Example 8

1.57 g of 1-chloromethyl-3-formylpyrazole hydrochloride and 1.52 g of (3,3,3-trifluoropropyl) malononitrile were dissolved in 30 ml of N,N-dimethylformamide. 2.76 g of potassium carbonate was added to the solution under ice cooling with stirring, followed by stirring at room temperature for 5 hours. Water was added to the reaction mixture, and then extracted with MTBE. The organic layer was washed with water, dried over anhydrous magnesium sulfate, filtered, and concentrated under reduced pressure. The residue was subjected to silica gel column chromatography to obtain 0.05 g of [(3-formyl-1H-pyrazole-1-yl)methyl](3,3,3-trifluoropropyl) malononitrile (referred as the compound of the present invention (8), hereinafter) shown by below formula.

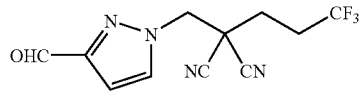

$^1$H-NMR(CDCl$_3$,TMS,δ(ppm)):2.28-2.34(2H,m),2.52-2.63(2H,m),4.77(2H,s),6.93(1H,s),7.70(1H,s),9.99(1H,s)

Production Example 9

1.00 g of 1-(chloromethyl)-3-cyano-1H-pyrazole and 1.15 g of (3,3,3-trifluoropropyl) malononitrile were dissolved in 21 ml of N,N-dimethylformamide. 1.96 g of potassium carbonate was added to the solution under ice cooling with stirring, followed by stirring at room temperature for 5 hours. Water was added to the reaction mixture, and then extracted with MTBE. The organic layer was washed with water, dried over anhydrous magnesium sulfate, filtered, and concentrated under reduced pressure. The residue was subjected to silica gel column chromatography to obtain 1.11 g of [(3-cyano-1H-pyrazole-1-yl)methyl](3,3,3-trifluoropropyl) malononitrile (referred as the compound of the present invention (9), hereinafter) shown by below formula.

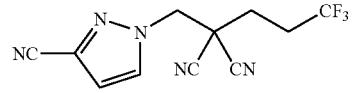

$^1$H-NMR(CDCl$_3$,TMS,δ(ppm)):2.23-2.27(2H,m),2.49-2.60(2H,m),4.75(2H,s),7.60(1H,s),7.66(1H,s)

Production Example 10

2.01 g of 1-(chloromethyl)-3-phenyl-1H-pyrazole hydrochloride and 1.42 g of (3,3,3-trifluoropropyl) malononitrile were dissolved in 27 ml of N,N-dimethylformamide. 2.43 g of potassium carbonate was added to the solution under ice cooling with stirring, followed by stirring at room temperature for overnight. Water was added to the reaction mixture, and then extracted with MTBE. The organic layer was washed with water, dried over anhydrous magnesium sulfate, filtered, and concentrated under reduced pressure. The residue was subjected to silica gel column chromatography to obtain 0.66 g of [(3-phenyl-1H-pyrazole-1-yl)methyl](3,3,3-trifluoropropyl)malononitrile (referred as the compound of the present invention (10), hereinafter) shown by below formula.

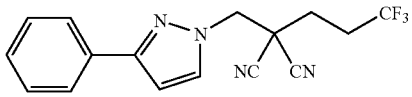

$^1$H-NMR(CDCl$_3$,TMS,δ(ppm)):2.33-2.37(2H,m),2.53-2.62(2H,m),4.73(2H,s),6.70(1H,d),7.33-7.44(3H,m),7.64(1H,d),7.78-7.80(2H, m)

Production Example 11

1.38 g of 4-bromo-3-i-propyl-1-(chloromethyl)-1H-pyrazole hydrochloride and 0.81 g of (3,3,3-trifluoropropyl) malononitrile were dissolved in 15 ml of N,N-dimethylformamide. 1.38 g of potassium carbonate was added to the solution under ice cooling with stirring, followed by stirring at room temperature for overnight. Water was added to the reaction mixture, and then extracted with MTBE. The organic layer was washed with water, dried over anhydrous magnesium sulfate, filtered, and concentrated under reduced pressure. The residue was subjected to silica gel column chromatography to obtain 0.91 g of [(4-bromo-3-i-propyl-1H-pyrazole-1-yl)methyl] (3,3,3-trifluoropropyl) malononitrile (referred as the compound of the present invention (11), hereinafter) shown by below formula.

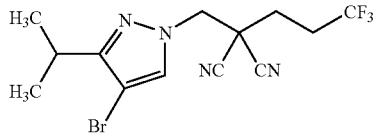

$^1$H-NMR(CDCl$_3$,TMS,δ(ppm)):1.25(6H,d),2.20-2.29(2H,m),2.51-2.58(2H,m),3.00-3.06(1H,m),4.60(2H,s),7.56(1H,s)

Production Example 12

1.85 g of 4-bromo-3-t-butyl-1-(chloromethyl)-1H-pyrazole hydrochloride and 1.18 g of (3,3,3-trifluoropropyl) malononitrile were dissolved in 21 ml of N,N-dimethylformamide. 2.02 g of potassium carbonate was added to the solution under ice cooling with stirring, followed by stirring at room temperature for overnight. Water was added to the reaction mixture, and then extracted with MTBE. The organic layer was washed with water, dried over anhydrous magnesium sulfate, filtered, and concentrated under reduced pressure. The residue was subjected to silica gel column chromatography to obtain 1.91 g of [(4-bromo-3-t-butyl-1H-pyrazole-1-yl)methyl](3,3,3-trifluoropropyl) malononitrile (referred as the compound of the present invention (12), hereinafter) shown by below formula.

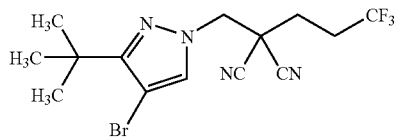

$^1$H-NMR(CDCl$_3$,TMS,δ(ppm)):1.38(9H,s),2.20-2.23(2H,m),2.49-2.61(2H,m),4.57(2H,s),7.57(1H,s)

Production Example 13

0.98 g of 4-chloro-3-t-butyl-1-(chloromethyl)-1H-pyrazole hydrochloride and 0.65 g of (3,3,3-trifluoropropyl) malononitrile were dissolved in 12 ml of N,N-dimethylformamide. 1.11 g of potassium carbonate was added to the solution under ice cooling with stirring, followed by stirring at room temperature for overnight. Water was added to the reaction mixture, and then extracted with MTBE. The organic layer was washed with water, dried over anhydrous magnesium sulfate, filtered, and concentrated under reduced pressure. The residue was subjected to silica gel column chromatography to obtain 0.40 g of [(4-chloro-3-t-butyl-1H-pyrazole-1-yl)methyl](3,3,3-trifluoropropyl) malononitrile (referred as the compound of the present invention (13), hereinafter) shown by below formula.

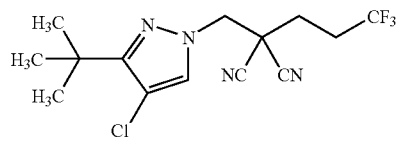

$^1$H-NMR(CDCl$_3$,TMS,δ(ppm)):1.36(9H,s),2.20-2.24(2H,m),2.49-2.61(2H,m),4.56(2H,s),7.54(1H,s)

Production Example 14

1.84 g of 4-bromo-3-t-butyl-1-(chloromethyl)-1H-pyrazole hydrochloride and 0.77 g of allyl malononitrile were dissolved in 21 ml of N,N-dimethylformamide. 2.02 g of potassium carbonate was added to the solution under ice cooling with stirring, followed by stirring at room temperature for overnight. Water was added to the reaction mixture, and then extracted with MTBE. The organic layer was washed with water, dried over anhydrous magnesium sulfate, filtered, and concentrated under reduced pressure. The residue was subjected to silica gel column chromatography to obtain 0.84 g of allyl [(4-bromo-3-t-butyl-1H-pyrazole-1-yl)methyl]malononitrile (referred as the compound of the present invention (14), hereinafter) shown by below formula.

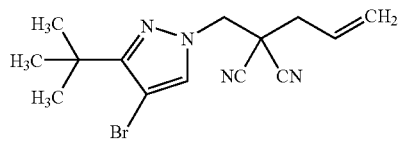

$^1$H-NMR(CDCl$_3$,TMS,δ(ppm)):1.40(9H,s),2.71(2H,d),4.51(2H,s),5.43-5.52(2H,m),5.87-5.98(1H,m),7.56(1H,s)

Production Example 15

1.67 g of 4-bromo-1-(chloromethyl)-3-trifluoromethyl-1H-pyrazole and 1.03 g of (3,3,3-trifluoropropyl) malononitrile were dissolved in 18 ml of N,N-dimethylformamide. 1.74 g of potassium carbonate was added to the solution under ice cooling with stirring, followed by stirring at room temperature for overnight. Water was added to the reaction mixture, and then extracted with MTBE. The organic layer was washed with water, dried over anhydrous magnesium sulfate, filtered, and concentrated under reduced pressure. The residue was subjected to silica gel column chromatography to obtain 0.97 g of [(4-bromo-3-trifluoromethyl-1H-pyrazole-1-yl)methyl](3,3,3-trifluoropropyl) malononitrile (referred as the compound of the present invention (15), hereinafter) shown by below formula.

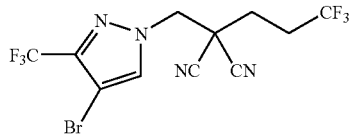

¹H-NMR(CDCl₃,TMS,δ(ppm)):2.25-2.30(2H,m),2.49-2.62(2H,m),4.70(2H,s),7.77 (1H,s)

Production Example 16

1.67 g of 4-bromo-1-(chloromethyl)-3-(trifluoromethyl)-1H-pyrazole and 0.67 g of allyl malononitrile were dissolved in 18 ml of N,N-dimethylformamide. 1.74 g of potassium carbonate was added to the solution under ice cooling with stirring, followed by stirring at room temperature for overnight. Water was added to the reaction mixture, and then extracted with MTBE. The organic layer was washed with water, dried over anhydrous magnesium sulfate, filtered, and concentrated under reduced pressure. The residue was subjected to silica gel column chromatography to obtain 0.90 g of allyl {[4-bromo-3-(trifluoromethyl)-1H-pyrazole-1-yl]methyl}}malononitrile (referred as the compound of the present invention (16), hereinafter) shown by below formula.

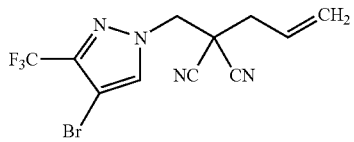

¹H-NMR(CDCl₃,TMS,δ(ppm)):2.75(2H,d),4.63(2H,s),5.50-5.55(2H,m),5.86-5.97(1H,m),7.76(1H,s)

Production Example 17

0.93 g of 1-(chloromethyl)-3,5-dimethyl-1H-pyrazole hydrochloride and 0.81 g of (3,3,3-trifluoropropyl)malononitrile were dissolved in 15 ml of N,N-dimethylformamide. 1.38 g of potassium carbonate was added to the solution under ice cooling with stirring, followed by stirring at room temperature for 4 hours. Water was added to the reaction mixture, and then extracted with MTBE. The organic layer was washed with water, dried over anhydrous magnesium sulfate, filtered, and concentrated under reduced pressure. The residue was subjected to silica gel column chromatography to obtain 0.45 g of the compound referred to as the compound of the present invention (17), hereinafter) shown by below formula.

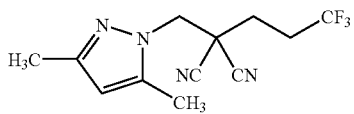

¹H-NMR(CDCl₃,TMS,δ(ppm)):2.23(3H,s),2.37(3H,s),2.41-2.61(4H,m),4.52(2H,s),5.91(1H,s)

Production Example 18

1.46 g of 1-(chloromethyl)-4-methyl-1H-pyrazole hydrochloride and 1.42 g of (3,3,3-trifluoropropyl) malononitrile were dissolved in 30 ml of N,N-dimethylformamide. 2.40 g of potassium carbonate was added to the solution under ice cooling with stirring, followed by stirring at room temperature for overnight. Water was added to the reaction mixture, and then extracted with MTBE. The organic layer was washed with water, dried over anhydrous magnesium sulfate, filtered, and concentrated under reduced pressure. The residue was subjected to silica gel column chromatography to obtain 0.83 g of the compound (referred to as the compound of the present invention (18), hereinafter) shown by below formula.

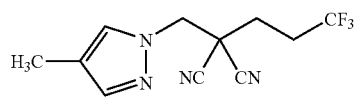

¹H-NMR(CDCl₃,TMS,δ(ppm)):2.11(3H,s),2.20-2.24(2H,m),2.46-2.58(2H,m),4.64(2H,s),7.38(1H,s),7.42(H,s)

Production Example 19

1.44 g of 4-chloro-1-(chloromethyl)-1H-pyrazole hydrochloride and 1.56 g of (3,3,3-trifluoropropyl) malononitrile were dissolved in 30 ml of N,N-dimethylformamide. 2.76 g of potassium carbonate was added to the solution under ice cooling with stirring, followed by stirring at room temperature for overnight. Water was added to the reaction mixture, and then extracted with MTBE. The organic layer was washed with water, dried over anhydrous magnesium sulfate, filtered, and concentrated under reduced pressure. The residue was subjected to silica gel column chromatography to obtain 1.73 g of [(4-chloro-1H-pyrazole-1-yl)methyl](3,3,3-trifluoropropyl) malononitrile (referred as the compound of the present invention (19), hereinafter) shown by below formula.

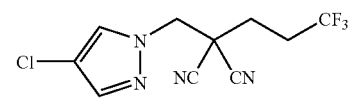

¹H-NMR(CDCl₃,TMS,δ(ppm)):2.17-2.31(2H,m),2.46-2.60(2H,m),4.64(2H,s),7.57(1H,s),7.63(1H,s)

Production Example 20

1.43 g of 4-chloro-1-(chloromethyl)-1H-pyrazole hydrochloride and 1.01 g of allyl malononitrile were dissolved in 30 ml of N,N-dimethylformamide. 2.76 g of potassium carbonate was added to the solution under ice cooling with stirring, followed by stirring at room temperature for overnight. Water was added to the reaction mixture, and then extracted with MTBE. The organic layer was washed with water, dried over anhydrous magnesium sulfate, filtered, and concentrated under reduced pressure. The residue was subjected to silica gel column chromatography to obtain 1.22 g of allyl [(4-chloro-1H-pyrazole-1-yl)methyl]malononitrile (referred as the compound of the present invention (20), hereinafter) shown by below formula.

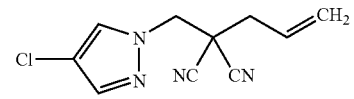

¹H-NMR(CDCl₃,TMS,δ(ppm)):2.72(2H,d),4.58(2H,s),5.46-5.52(2H,m),5.87-5.98(1H,m),7.57(1H,s),7.63(1H,s)

Production Example 21

3.27 g of 4-bromo-1-(chloromethyl)-1H-pyrazole hydrochloride and 2.29 g of (3,3,3-trifluoropropyl) malononitrile were dissolved in 28 ml of N,N-dimethylformamide. 3.89 g of potassium carbonate was added to the solution under ice cooling with stirring, followed by stirring at room temperature for overnight. Water was added to the reaction mixture, and then extracted with MTBE. The organic layer was washed with water, dried over anhydrous magnesium sulfate, filtered, and concentrated under reduced pressure. The residue was subjected to silica gel column chromatography to obtain 3.28 g of [(4-bromo-1H-pyrazole-1-yl)methyl](3,3,3-trifluoropropyl) malononitrile (referred as the compound of the present invention (21), hereinafter) shown by below formula.

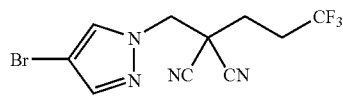

$^1$H-NMR(CDCl$_3$,TMS,δ(ppm)):2.17-2.27(2H,m),2.48-2.60(2H,m),4.66(2H,s),7.60(1H,s),7.65(1H,s)

Production Example 22

0.60 g of 1-(chloromethyl)-4-(trifluoromethyl)-1H-pyrazole and 0.54 g of (3,3,3-trifluoropropyl) malononitrile were dissolved in 10 ml of N,N-dimethylformamide. 0.99 g of potassium carbonate was added to the solution under ice cooling with stirring, followed by stirring at room temperature for overnight. Water was added to the reaction mixture, and then extracted with MTBE. The organic layer was washed with water, dried over anhydrous magnesium sulfate, filtered, and concentrated under reduced pressure. The residue was subjected to silica gel column chromatography and then recrystallized from hexane-chloroform to obtain 0.19 g of {[4-(trifluoromethyl)-1H-pyrazole-1-yl]methyl}(3,3,3-trifluoropropyl) malononitrile (referred as the compound of the present invention (22), hereinafter) shown by below formula.

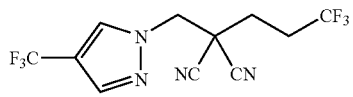

$^1$H-NMR(CDCl$_3$,TMS,δ(ppm)):2.28-2.32(2H,m),2.53-2.57(2H,m),4.71(2H,s),7.85(1H,s),7.93(1H,s)

Production Example 23

0.80 g of 1-(chloromethyl)-4-methoxycarbonyl-1H-pyrazole and 0.75 g of (3,3,3-trifluoropropyl) malononitrile were dissolved in 15 ml of N,N-dimethylformamide. 1.27 g of potassium carbonate was added to the solution under ice cooling with stirring, followed by stirring at room temperature for overnight. Water was added to the reaction mixture, and then extracted with MTBE. The organic layer was washed with water, dried over anhydrous magnesium sulfate, filtered, and concentrated under reduced pressure. The residue was subjected to silica gel column chromatography, and then recrystallized from hexane-chloroform to obtain 0.48 g of [{4-(methoxycarbonyl)-1H-pyrazole-1-yl}methyl](3,3,3-trifluoropropyl) malononitrile (referred to as the compound of the present invention (23), hereinafter) shown by below formula.

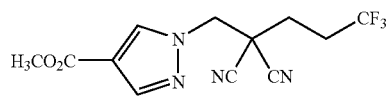

$^1$H-NMR(CDCl$_3$,TMS,δ(ppm)):2.27-2.32(2H,m),2.47-2.62(2H,m),3.86(3H,s),4.71(2H,s),8.03(1H,s),8.12(1H,s)

Production Example 24

0.79 g of 1-(chloromethyl)-4-methoxycarbonyl-1H-pyrazole and 0.49 g of allyl malononitrile were dissolved in 15 ml of N,N-dimethylformamide. 1.26 g of potassium carbonate was added to the solution under ice cooling with stirring, followed by stirring at room temperature for overnight. Water was added to the reaction mixture, and then extracted with MTBE. The organic layer was washed with water, dried over anhydrous magnesium sulfate, filtered, and concentrated under reduced pressure. The residue was subjected to silica gel column chromatography, and then recrystallized from hexane-chloroform to obtain 0.50 g of allyl [{4-(methoxycarbonyl)-1H-pyrazole-1-yl}methyl]malononitrile (referred to as the compound of the present invention (24), hereinafter) shown by below formula.

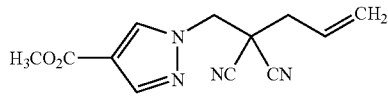

$^1$H-NMR(CDCl$_3$,TMS,δ(ppm)):2.76(2H,d),3.85(3H,s),4.64(2H,s),5.47-5.54(2H,m),5.85-5.99(1H,m),8.02(1H,s),8.11(1H,s)

Production Example 25

1.13 g of 1-(chloromethyl)-3-(trifluoromethyl)-4-ethoxycarbonyl-1H-pyrazole and 0.71 g of (3,3,3-trifluoropropyl) malononitrile were dissolved in 13 ml of N,N-dimethylformamide. 1.22 g of potassium carbonate was added to the solution under ice cooling with stirring, followed by stirring at room temperature for overnight. Water was added to the reaction mixture, and then extracted with MTBE. The organic layer was washed with water, dried over anhydrous magnesium sulfate, filtered, and concentrated under reduced pressure. The residue was subjected to silica gel column chromatography to obtain 0.30 g of {[4-ethoxycarbonyl-3-(trifluoromethyl)-pyrazole-1H-yl]methyl}(3,3,3-trifluoropropyl) malononitrile (referred as the compound of the present invention (25), hereinafter) shown by below formula.

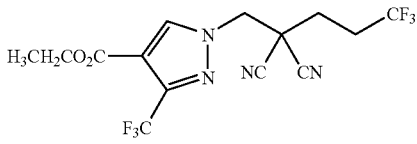

$^1$H-NMR(CDCl$_3$,TMS,δ(ppm)):1.37(3H,t),2.30-2.34(2H,m),2.52-2.63(2H,m),4.35(2H,q),4.73(2H,s),8.24(1H,s)

Production Example 26

1.25 g of 1-(chloromethyl)-3-(trifluoromethyl)-4-ethoxycarbonyl-1H-pyrazole and 0.52 g of allyl malononitrile were dissolved in 15 ml of N,N-dimethylformamide. 1.35 g of potassium carbonate was added to the solution under ice cooling with stirring, followed by stirring at room temperature for overnight. Water was added to the reaction mixture, and then extracted with MTBE. The organic layer was washed with water, dried over anhydrous magnesium sulfate, filtered, and concentrated under reduced pressure. The residue was subjected to silica gel column chromatography, and then recrystallized from hexane to obtain 0.14 g of allyl {[4-ethoxycarbonyl-3-(trifluoromethyl)-pyrazole-1H-yl]methyl}malononitrile (referred as the compound of the present invention (26), hereinafter) shown by below formula.

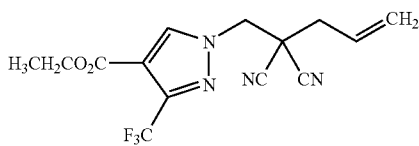

$^1$H-NMR(CDCl$_3$,TMS,δ(ppm)):1.36(3H,t),2.80(2H,d), 4.30(2H,q),4.68(2H,s),5.46-5.56(2H,m),5.88-5.98(1H,m), 8.24(1H,s)

Production Example 27

0.77 g of 1-(chloromethyl)-1H-1,2,4-triazole hydrochloride and 0.81 g of (3,3,3-trifluoropropyl) malononitrile were dissolved in 15 ml of N,N-dimethylformamide. 1.38 g of potassium carbonate was added to the solution under ice cooling with stirring, followed by stirring at room temperature for 7 hours. Water was added to the reaction mixture, and then extracted with MTBE. The organic layer was washed with water, dried over anhydrous magnesium sulfate, filtered, and concentrated under reduced pressure. The residue was recrystallized from hexane-MTBE to obtain 0.42 g of [(1H-1,2,4-triazole-1-yl)methyl](3,3,3-trifluoropropyl) malononitrile (referred as the compound of the present invention (27), hereinafter) shown by below formula.

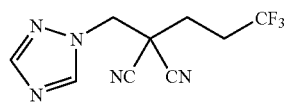

$^1$H-NMR(CDCl$_3$,TMS,δ(ppm)):2.31-2.37(2H,m),2.52-2.63(2H,m),4.77(2H, s) ,8.09 (1H, s) ,8.33 (1H, s)

Production Example 28

0.78 g of 3-i-propyl-1-(chloromethyl) -1H-1,2,4-triazole hydrochloride and 0.65 g of (3,3,3-trifluoropropyl) malononitrile were dissolved in 12 ml of N,N-dimethylformamide. 1.10 g of potassium carbonate was added to the solution under ice cooling with stirring, followed by stirring at room temperature for overnight. Water was added to the reaction mixture, and then extracted with MTBE. The organic layer was washed with water, dried over anhydrous magnesium sulfate, filtered, and concentrated under reduced pressure. The residue was recrystallized from hexane-MTBE to obtain 0.31 g of [(3-i-propyl-1H-1,2,4-triazole-1-yl)methyl](3,3,3-trifluoropropyl) malononitrile (referred as the compound of the present invention (28), hereinafter) shown by below formula.

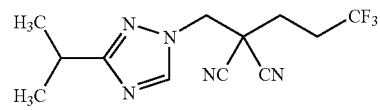

$^1$H-NMR(CDCl$_3$,TMS,δ(ppm)):1.32(6H,d),2.31-2.35 (2H,m),2.45-2.63(2H,m),3.06-3.13(1H,m),4.68(2H,s),8.19 (1H,s)

Production Example 29

1.61 g of 3-t-butyl-1-(chloromethyl)-1H-1,2,4-triazole hydrochloride and 1.24 g of (3,3,3-trifluoropropyl) malononitrile were dissolved in 22 ml of N,N-dimethylformamide. 2.13 g of potassium carbonate was added to the solution under ice cooling with stirring, followed by stirring at room temperature for 4 hours. Water was added to the reaction mixture, and then extracted with MTBE. The organic layer was washed with water, dried over anhydrous magnesium sulfate, filtered, and concentrated under reduced pressure. The residue was recrystallized from hexane-MTBE to obtain 0.77 g of [(3-t-butyl-1H-1,2,4-triazole-1-yl)methyl](3,3,3-trifluoropropyl) malononitrile (referred as the compound of the present invention (29), hereinafter) shown by below formula.

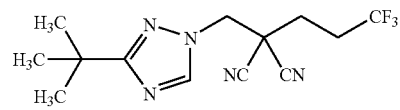

$^1$H-NMR(CDCl$_3$,TMS,δ(ppm)):1.37(9H,s),2.31-2.34 (2H,m),2.51-2.63(2H,m),4.67(2H,s),8.18(1H,s)

Production Example 30

0.98 g of 3-(1,1-dimethylpropyl)-1-(chloromethyl)-1H-1, 2,4-triazole hydrochloride and 0.65 g of (3,3,3-trifluoropropyl) malononitrile were dissolved in 12 ml of N,N-dimethylformamide. 1.11 g of potassium carbonate was added to the solution under ice cooling with stirring, followed by stirring at room temperature for overnight. Water was added to the reaction mixture, and then extracted with MTBE. The organic layer was washed with water, dried over anhydrous magnesium sulfate, filtered, and concentrated under reduced pressure. The residue was recrystallized from hexane-MTBE to obtain 0.29 g of {[3-(1,1-dimethylpropyl)-1H-1,2,4-triazole-1-yl]methyl}(3,3,3-trifluoropropyl) malononitrile (referred as the compound of the present invention (30), hereinafter) shown by below formula.

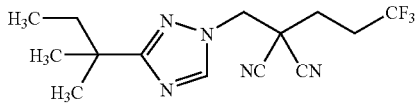

$^1$H-NMR(CDCl$_3$,TMS,δ(ppm)):0.72(3H,t),1.33(6H,s), 1.69(2H,q),2.31-2.35(2H,m),2.51-2.63(2H,m),4.68(2H,s), 8.19(1H,s)

Production Example 31

1.28 g of 1-(chloromethyl)-3-t-butyl-1H-1,2,4-triazole hydrochloride and 0.77 g of allyl malononitrile were dissolved in 21 ml of N,N-dimethylformamide. 1.01 g of potassium carbonate was added to the solution under ice cooling with stirring, followed by stirring at room temperature for 4 hours. Water was added to the reaction mixture, and then extracted with MTBE. The organic layer was washed with water, dried over anhydrous magnesium sulfate, filtered, and concentrated under reduced pressure. The residue was recrystallized from hexane-MTBE to obtain 0.16 g of allyl [(3-t-butyl-1H-1,2,4-triazole-1-yl)methyl]malononitrile (referred as the compound of the present invention (31), hereinafter) shown by below formula.

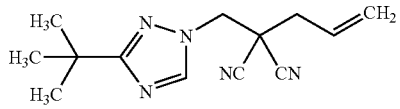

$^1$H-NMR(CDCl$_3$,TMS,δ(ppm)):1.38(9H,s),2.79(2H,d), 4.61(2H,s),5.50-5.54(2H,m),5.89-6.00(1H,m),8.16(1H,s)

Production Example 32

2.03 g of 5-bromo-3-t-butyl-1-(chloromethyl)-1H-1,2,4-triazole hydrochloride and 1.30 g of (3,3,3-trifluoropropyl)malononitrile were dissolved in 24 ml of N,N-dimethylformamide. 2.21 g of potassium carbonate was added to the solution under ice cooling with stirring, followed by stirring at room temperature for overnight. Water was added to the reaction mixture, and then extracted with MTBE. The organic layer was washed with water, dried over anhydrous magnesium sulfate, filtered, and concentrated under reduced pressure. The residue was subjected to silica gel column chromatography to obtain 0.76 g of [(5-bromo-3-t-butyl-1H-1,2,4-triazole 1-yl)methyl](3,3, 3-trifluoropropyl)malononitrile (referred as the compound of the present invention (32), hereinafter) shown by below formula.

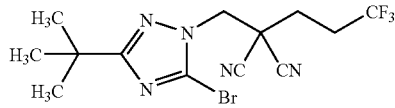

$^1$H-NMR (CDCl$_3$, TMS, δ(ppm)): 1.34 (9H,s),2.40-2.45 (2H,m),2.51-2.64 (2H,m),4.62(2H,s)

Production Example 33

1.56 g of 1-(chloromethyl)-3-(trifluoromethyl)-1H-1,2,4-triazole and 1.38 g of (3,3,3-trifluoropropyl)malononitrile were dissolved in 25 ml of N,N-dimethylformamide. 2.35 g of potassium carbonate was added to the solution under ice cooling with stirring, followed by stirring at room temperature for 4 hours. Water was added to the reaction mixture, and then extracted with MTBE. The organic layer was washed with water, dried over anhydrous magnesium sulfate, filtered, and concentrated under reduced pressure. The residue was recrystallized from hexane-MTBE to obtain 0.15 g of {[3-(trifluoromethyl)-1H-1,2,4-triazole-1-yl]methyl}(3,3,3-trifluoropropyl)malononitrile (referred as the compound of the present invention (33), hereinafter) shown by below formula.

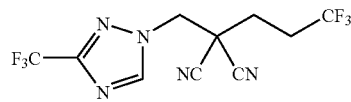

1H-NMR (CDCl$_3$, TMS, δ (ppm)): 2.34-2.38(2H,m),2.51-2.65(2H,m),4.82 (2H,s),8.45 (1H,s)

Production Example 34

1.74 g of 1-(chloromethyl)-3-(pentafluoroethyl)-1H-1,2,4-triazole and 1.20 g of (3,3,3-trifluoropropyl)malononitrile were dissolved in 21 ml of N,N-dimethylformamide. 2.04 g of potassium carbonate was added to the solution under ice cooling with stirring, followed by stirring at room temperature for 4 hours. Water was added to the reaction mixture, and then extracted with MTBE. The organic layer was washed with water, dried over anhydrous magnesium sulfate, filtered, and concentrated under reduced pressure. The residue was recrystallized from hexane-MTBE to obtain 0.25 g of {[3-(pentafluoroethyl)-1H-1,2,4-triazole 1-yl]methyl}(3,3,3-trifluoropropyl) malononitrile (referred as the compound of the present invention (34), hereinafter) shown by below formula.

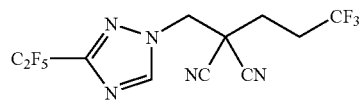

1H-NMR (CDCl$_3$, TMS, δ (ppm)): 2.32-2.36 (2H, m), 2.52-2.64 (2H, m), 4. 84 (2H, s), 8.47 (1H, s)

Production Example 35

2.24 g of 1-(chloromethyl)-3-(pentafluoroethyl)-1H-1,2,4-triazole and 1.02 g of allyl malononitrile were dissolved in 28 ml of N,N-dimethylformamide. 2.76 g of potassium carbonate was added to the solution under ice cooling with stirring, followed by stirring at room temperature for overnight. Water was added to the reaction mixture, and then extracted with MTBE. The organic layer was washed with water, dried over anhydrous magnesium sulfate, filtered, and concentrated under reduced pressure. The residue was subjected to silica gel column chromatography, and then subjected to preparative high performance liquid chromatography to obtain 0.54 g of allyl {[3-(pentafluoroethyl)-1H-1,2,4-triazole 1-yl]methyl}malononitrile (referred as the compound of the present invention (35), hereinafter) shown by below formula.

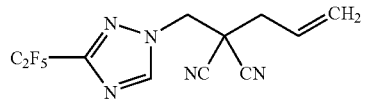

$^1$H-NMR (CDCl$_3$, TMS, δ (ppm)): 2.81 (2H, d), 4.76 (2H, s), 5.53-5.59 (2H , m), 5.88-5.97 (1H, m), 8.45 (1H, s)

Production Example 36

2.01 g of 1-(chloromethyl)-3-(pentafluoroethyl)-1H-pyrazole and 1.39 g of (3,3,3-trifluoropropyl)malononitrile were dissolved in 25 ml of N,N-dimethylformamide. 2.38 g of potassium carbonate was added to the solution under ice cooling with stirring, followed by stirring at room temperature for overnight. Water was added to the reaction mixture, and then extracted with MTBE. The organic layer was washed with water, dried over anhydrous magnesium sulfate, filtered, and concentrated under reduced pressure. The residue was subjected to silica gel column chromatography to obtain 1.31 g of {[3-(pentafluoroethyl)-1H-pyrazole-1-yl] methyl}(3,3, 3-trifluoropropyl)malononitrile (referred as the compound of the present invention (36), hereinafter) shown by below formula.

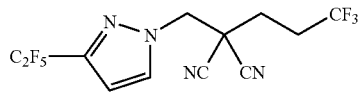

¹H-NMR (CDCl₃, TMS, δ (ppm)): 2.23-2.27 (2H, m), 2.49-2.59 (2H, m), 4.77 (2H, s), 6.72 (1H, d), 7.75 (1H, d)

Production Example 37

6.84 g of 4-bromo-1-(chloromethyl)-3-(pentafluoroethyl)-1H-pyrazole and 3.54 g of (3,3,3-trifluoropropyl)malononitrile were dissolved in 60 ml of N,N-dimethylformamide. 6.08 g of potassium carbonate was added to the solution under ice cooling with stirring, followed by stirring at room temperature for overnight. Water was added to the reaction mixture, and then extracted with MTBE. The organic layer was washed with water, dried over anhydrous magnesium sulfate, filtered, and concentrated under reduced pressure. The residue was subjected to silica gel column chromatography to obtain 7.15 g of [(4-bromo-3-(pentafluoroethyl)-1H-pyrazole-1-yl) methyl](3,3, 3-trifluoropropyl) malononitrile (referred as the compound of the present invention (37), hereinafter) shown by below formula.

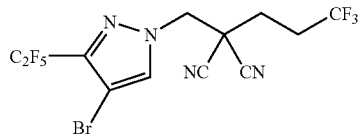

¹H-NMR (CDCl₃, TMS, δ (ppm)): 2.24-2.29 (2H, m), 2.49-2.61 (2H, m), 4.75 (2H, s), 7.81 (1H, s)

Production Example 38

2.90 g of 1-(chloromethyl)-4-(trifluoromethyl)-1H-imidazole hydrochloride and 2.11 g of (3,3,3-trifluoropropyl)malononitrile were dissolved in 39 ml of N,N-dimethylformamide. 3.59 g of potassium carbonate was added to the solution under ice cooling with stirring, followed by stirring at room temperature for overnight. Water was added to the reaction mixture, and then extracted with MTBE. The organic layer was washed with water, dried over anhydrous magnesium sulfate, filtered, and concentrated under reduced pressure. The residue was subjected to silica gel column chromatography to obtain 1.12 g of {[4-(trifluoromethyl)-1H-imidazole-1-yl]methyl}(3,3,3-trifluoropropyl) malononitrile (referred as the compound of the present invention (38), hereinafter) shown by below formula.

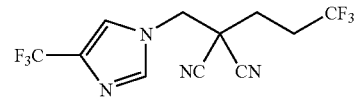

¹H-NMR (CDCl₃, TMS, δ (ppm)): 2.24-2.28 (2H, m), 2.54-2.65 (2H, m), 4.53 (2H, s), 7.50 (1H, s), 7.73 (1H, s)

Production Example 39

1.70 g of 1-(chloromethyl)-3-cyano-1H-indole and 1.45 g of (3,3,3-trifluoropropyl) malononitrile were dissolved in 27 ml of N,N-dimethylformamide. 2.49 g of potassium carbonate was added to the solution under ice cooling with stirring, followed by stirring at room temperature for 7 hours. Water was added to the reaction mixture, and then extracted with MTBE. The organic layer was washed with water, dried over anhydrous magnesium sulfate, filtered, and concentrated under reduced pressure. The residue was subjected to silica gel column chromatography to obtain 1.48 g of [{3-cyano-1H-indole-1-yl}methyl] (3,3,3-trifluoropropyl) malononitrile (referred to as the compound of the present invention (39), hereinafter) shown by below formula.

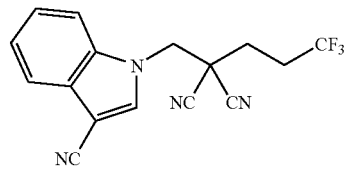

¹H-NMR(CDCl₃. TMS,δ (ppm)):2.28-2.32(2H, m), 2.51-2.63 (2H, m), 4.78 (2H, s), 7.37-7.47(2H, m), 7.53 (1H, d), 7.80-7.83 (2H, m)

Production Example 40

3.02 g of 1-(chloromethyl)-3-formyl-1H-indole and 2.53 g of (3,3,3-trifluoropropyl) malononitrile were dissolved in 45 ml of N,N-dimethylformamide. 4.35 g of potassium carbonate was added to the solution under ice cooling with stirring, followed by stirring at room temperature for 3 hours. Water was added to the reaction mixture, and then extracted with MTBE. The organic layer was washed with water, dried over anhydrous magnesium sulfate, filtered, and concentrated under reduced pressure. The residue was subjected to silica gel column chromatography to obtain 2.68 g of [{3-formyl-1H-indole-1-yl}methyl](3,3,3-trifluoropropyl)malononitrile (referred to as the compound of the present invention (40), hereinafter) shown by below formula.

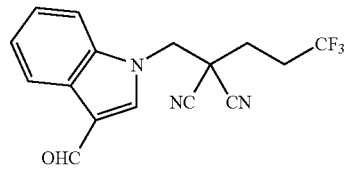

¹H-NMR (DMSO-d₆, TMS, δ (ppm)): 2.33-2.51 (2H, m), 2.59-2.75 (2H, m), 5.29 (2H, s), 7.30-7.40 (2H, m), 7.97 (1H, d), 8.14 (1H, d), 8.36 (1H, s), Production Example 41

3.53 g of 1-(chloromethyl)-3-(trifluoroacetyl)-1H-indole and 2.19 g of(3,3,3-trifluoropropyl) malononitrile were dissolved in 27 ml of N,N-dimethylformamide. 3.74 g of potassium carbonate was added to the solution under ice cooling with stirring, followed by stirring at room temperature for overnight. Water was added to the reaction mixture, and then extracted with MTBE. The organic layer was washed with water, dried over anhydrous magnesium sulfate, filtered, and concentrated under reduced pressure. The residue was subjected to silica gel column chromatography to obtain 3.06 g of [{3-(trifluoroacetyl)-1H-indole-1-yl}methyl](3,3,3-trifluoropropyl) malononitrile (referred to as the compound of the present invention (41), hereinafter) shown by below formula.

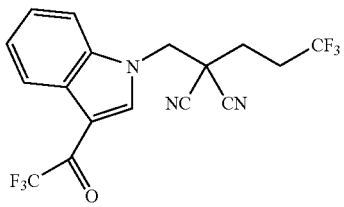

¹H-NMR (CDCl₃, TMS, δ (ppm)): 2.33-2.37 (2H, m), 2.53-2.65 (2H, m), 4.85 (2H, s), 7.44-7.50 (2H, m), 7.52-7.57 (1H, m), 8.16 (1H, s), 8.44-8.47 (1H, m)

Production Example 42

1.21 g of [(1H-pyrazole-1-yl)methyl](3,3,3-trifluoropropyl)malononitrile (the compound of the present invention (1)) was dissolved in 50 ml of acetonitrile. 2.19 g of ammonium cerium (IV) nitrate and 1.02 g of iodine were added to the solution, followed by stirring at room temperature for 10 hours. The reaction mixture was concentrated under reduced pressure. The residue was subjected to silica gel column chromatography to obtain 1.71 g of [(4-iodo-1H-pyrazole-1-yl)methyl] (3,3,3-trifluoropropyl) malononitrile (referred as the compound of the present invention (42), hereinafter) shown by below formula.

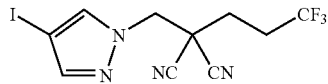

¹H-NMR (CDCl₃, TMS, δ (ppm)): 2.04-2.27 (2H, m), 2.48 (2H, m), 4.69 (2H, s), 7.65 (1H, s), 7.67 (1H, s)

Production Example 43

0.21 g of 1-(chloromethyl)-4-[(dichlorofluoromethyl) thio]-1H-pyrazole and 0.14 g of (3,3,3-trifluoropropyl) malononitrile were dissolved in 2 ml of N,N-dimethylformamide. 0.12 g of potassium carbonate was added to the solution under ice cooling, followed by stirring at room temperature for overnight. Water was added to the reaction mixture, and then extracted with MTBE. The organic layer was washed with water, dried over anhydrous magnesium sulfate, filtered. The filtrate was concentrated under reduced pressure to obtain 0.06 g of [(4-{(dichlorofuoromethyl)thio}-1H-pyrazole-1-yl)methyl](3,3,3-trifluoropropyl)malononitrile (referred as the compound of the present invention (43), hereinafter) shown by below formula.

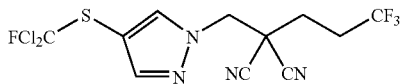

¹H-NMR (CDCl₃, TMS, δ (ppm)): 2.24-2.33 (2H, m), 2.49-2.59 (2H, m), 5. 43 (2H, s), 7.83 (1H, s), 7.96 (1H, s)

Production Example 44

0.61 g of 1-(chloromethyl)-3-{[dichlorofluoromethyl] thio}-1H-indole and 0.35 g of (3,3,3-trifluoropropyl)malononitrile were dissolved in 2 ml of N,N-dimethylformamide. 0.28g of potassium carbonate was added to the solution under ice cooling, followed by stirring at room temperature for overnight. Water was added to the reaction mixture, and then extracted with MTBE. The organic layer was washed with water, dried over anhydrous magnesium sulfate, filtered. The filtrate was concentrated under reduced pressure. The residue was subjected to silica gel column chromatography to obtain 0.65 g of [(3-{[dichlorofluoromethyl]thio}-1H-indole-1-yl) methyl](3,3, 3-trifluoropropyl) malononitrile (referred as the compound of the present invention (44), hereinafter) shown by below formula.

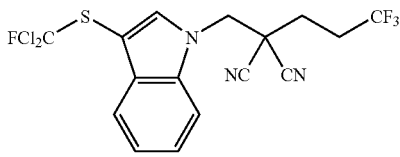

¹H-NMR (CDCl₃, TMS, δ (ppm)): 2.05-2.28 (2H, m), 2.49-2.60 (2H, m), 4. 80 (2H, s), 7.34-7.42 (2H, m), 7.50 (1H, d), 7.67 (1H, s), 7.86 (1H, s)

Production Example 45

0.61 g of 1-chloromethyl-3-nitro-1H-pyrole and 0.65 g of (3,3,3-trifluoropropyl) malononitrile were dissolved in 10 ml of N,N-dimethylformamide. 0.28 g of potassium carbonate was added to the solution under ice cooling, followed by stirring at room temperature for overnight. Water was added to the reaction mixture, and then extracted with ethyl acetate. The organic layer was washed with saturated aqueous solution of sodium chloride, dried over anhydrous magnesium sulfate, filtered. The filtrate was concentrated under reduced pressure. The residue was subjected to silica gel column chromatography to obtain 0.80 g of [(3-nitro-1H-pyrole-1-yl) methyl](3,3,3-trifluoropropyl) malononitrile (referred as the compound of the present invention (45), hereinafter) shown by below formula.

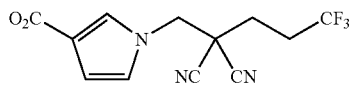

¹H-NMR (CDCl₃, TMS, δ (ppm)): 2.22-2.26 (2H, m), 2.52-2.63 (2H, m), 4. 46 (2H,s), 6.81-6.83 (1H, m), 6.88 (1H, t), 7.69 (1H, d)

Production Example 46

0.80 g of 1-chloromethyl-3-cyano-4-trifluoromethyl-1H-pyrole and 0.67 g of (3,3,3-trifluoropropyl)malononitrile were dissolved in 10 ml of N,N-dimethylformamide. 0.57 g of potassium carbonate was added to the solution under ice cooling, followed by stirring at room temperature for overnight. Water was added to the reaction mixture, and then extracted with ethyl acetate. The organic layer was washed with saturated aqueous solution of sodium chloride, dried over anhydrous magnesium sulfate, filtered. The filtrate was concentrated under reduced pressure. The residue was subjected to silica gel column chromatography to obtain 0.33 g of [(3-cyano-4-trifluoromethyl-1H-pyrole-1-yl) methyl](3,3, 3-trifluoropropyl) malononitrile (referred as the compound of the present invention (46), hereinafter) shown by below formula.

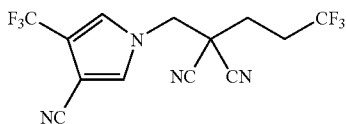

¹H-NMR (DMSO-d₆, TMS, δ (ppm)): 2.45-2.51 (2H, m), 2.62-2.74 (2H, m), 4.98 (2H, s), 7.76-7.77 (1H, m), 8.04 (1H, d)

Production Example 47

0.23 g of 1-chloromethyl-4-trifluoromethyl-3-ethoxycarbonyl-1H-pyrole and 0.15 g of (3,3,3-trifluoropropyl)malononitrile were dissolved in 2 ml of N,N-dimethylformamide. 0.13 g of potassium carbonate was added to the solution under ice cooling, followed by stirring at room temperature for overnight. Water was added to the reaction mixture, and then extracted with ethyl acetate. The organic layer was washed with saturated aqueous solution of sodium chloride, dried over anhydrous magnesium sulfate, filtered. The filtrate was concentrated under reduced pressure. The residue was subjected to silica gel column chromatography to obtain 0.20 g of [(3-ethoxycarbonyl-4-trifluoromethyl-1H-pyrole-1-yl) methyl](3,3,3-trifluoropropyl)malononitrile (referred as the compound of the present invention (47), hereinafter) shown by below formula.

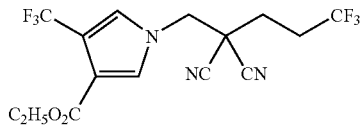

¹H-NMR (CDCl₃, TMS, δ (ppm)): 1.35 (3H, t), 2.21-2.26 (2H, m), 2.56-2.63 (2H, m), 4.35 (2H, q), 4.45 (2H, s), 7.20 (1H, d), 7.53 (1H, d)

Production Example 48

0.27 g of 1-chloromethyl-3-cyano-1H-pyrole and 0.34 g of (3,3,3-trifluoropropyl)malononitrile were dissolved in 3ml of N,N-dimethylformamide. 0.29 g of potassium carbonate was added to the solution under ice cooling, followed by stirring at room temperature for 1 hour. Water was added to the reaction mixture, and then extracted with ethyl acetate. The organic layer was washed with saturated aqueous solution of sodium chloride, dried over anhydrous magnesium sulfate, filtered. The filtrate was concentrated under reduced pressure. The residue was subjected to silica gel column chromatography to obtain 0.37 g of [(3-cyano-1H-pyrole-1-yl) methyl] (3,3,3-trifluoropropyl) malononitrile (referred as the compound of the present invention (48), hereinafter) shown by below formula.

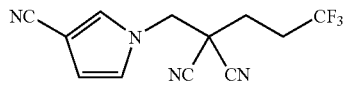

¹H-NMR (CDCl₃, TMS, δ (ppm)): 2.18-2.23 (2H, m), 2.46-2.64 (2H, m), 4.46 (2H, s), 6.58-6.59 (1H, m), 6.87-6.88 (1H, m), 7.33-7.35 (1H, m)

Next, reference production examples of the intermediate compound are illustrated.

Reference Production Example 1-1

1H-pyrazole-1-ylmethanol

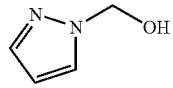

The mixture of 2.04 g of pyrazole, 2.00 g of paraformaldehyde and 1 ml of triethylamine was stirred at 130° C. for 10 hours. After the reaction mixture was cooled to room temperature, acetone was added to the reaction mixture, and then the mixture was filtered. The filterate was concentrated under reduced pressure. Hexane was added to the residue, and then crystalline was formed. The crystalline was collected to obtain 3.10 g of 1H-pyrazole-1-ylmethanol.

¹H-NMR(CDCl₃, TMS, δ (ppm)): 5.51 (2H, s), 6.30 (1H, t), 7.58-7.61 (2H, m)

Reference Production Example 1-2

1-(chloromethyl)-1H-pyrazole hydrochloride

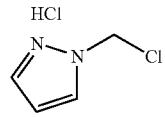

3.10 g of 1H-pyrazole-1-ylmethanol was dissolved to 100 ml of dichloromethane. 6.8 ml of thionyl chloride was added to the solution, followed by stirring at room temperature for overnight. The reaction mixture was concentrated under reduced pressure. The residue was recrystallized from hexane-chloroform to obtain 2.66 g of 1-(chloromethyl)-1H-pyrazole hydrochloride.

¹H-NMR(CDCl₃, TMS, δ (ppm)): 5.91 (2H, s), 6.38 (1H, t), 7.61-7.68 (2H, m)

Reference Production Example 2-1

3-i-propyl-1H-pyrazole

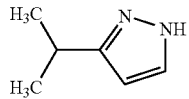

Under nitrogen atmosphere, mixture of 17.23 g of isopropyl methyl ketone and 12.01 g of methyl formate was cooled to 0° C., and then 22.44 g of potassium t-butoxide dissolved to 200 ml of tetrahydrofuran was added to the mixture over the period for 1 hour. During that, the temperature of the mixture was kept below 20° C. After that, the reaction mixture was stirred at 30 C. for 5 hours. 200 ml of diethyl ether was added to the reaction mixture which was cooled to room temperature, as a result, solid was produced. The solid was collected by filtration, and washed with 20 ml of diethyl ether. The obtained solid was dried under reduced pressure to give 14.14 g of 1-hydroxy-4-methyl-1-pentene-3-one potassium salt. 14.14 g of 1-hydroxy-4-methyl-1-pentene-3-one potassium salt was suspended to 90 ml of ethanol. 5.11 g of hydrazine hydrate was added to the suspension, and then refluxed for 7 hours. 30 ml of water was added to the reaction mixture which was cooled to room temperature, and the mixture was concentrated to 30 ml under reduced pressure. The residue was extracted by ethyl acetate. The organic layer was dried over anhydrous magnesium sulfate, filtered, and concentrated under reduced pressure. The residue was subjected to silica gel column chromatography to obtain 6.83 g of 3-i-propyl-1H-pyrazole.

$^1$H-NMR (CDCl$_3$. TMS, δ (ppm)): 1.29 (6H, d), 3.01-3.08 (1H, m), 6.10 (1H, s), 7.49 (1H,s)

Reference Production Example 2-2

3-i-propyl-1H-pyrazole-1-ylmethanol

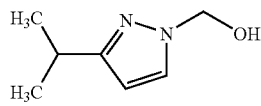

The mixture of 1.15 g of 3-i-propyl-1H-pyrazole, 0.94 g of paraformaldehyde and 0.14 g of triethylamine was stirred at 130° C. for 7 hours. After the reaction mixture was cooled to room temperature, acetone was added to the reaction mixture. The mixture was filtered. The filtrate was concentrated under reduced pressure. Hexane was added to the residue, and then crystalline was formed. The crystalline was collected to obtain 1.28 g of 3-i-propyl-1H-pyrazole-1-ylmethanol.

$^1$H-NMR (CDCl$_3$, TMS, δ (ppm)): 1.24 (6H, d), 2.94-3.02 (1H, m), 5.48 (2H ,s), 6.10 (1H, d), 7.47 (1H, d)

Reference Production Example 2-3

3-i-propyl-1-(chloromethyl)-1H-pyrazole hydrochloride

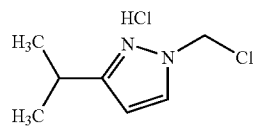

1.28 g of 3-i-propyl-1H-pyrazole-1-ylmethanol was dissolved to 20 ml of dichloromethane. 2 ml of thionyl chloride was added to the solution, followed by stirring at room temperature for overnight. The reaction mixture was concentrated under reduced pressure to obtain 1.58 g of 3-i-propyl-1-(chloromethyl)-1H-pyrazole hydrochloride.

Reference Production Example 3-1

3-t-butyl-1H-pyrazole

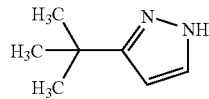

Under nitrogen atmosphere, mixture of 50.00 g of pinacolone and 42.00 g of methyl formate was cooled to 0° C., and then 56.00 g of potassium t-butoxide was added to the mixture over the period for 3 hours. During that, the temperature of the mixture was kept below 20° C. After that, the reaction mixture was stirred at 30° C. for 5 hours. Diethyl ether was added to the reaction mixture which was cooled to room temperature, as a result, solid was produced. The solid was collected by filtration, and dried under reduced pressure to give 32.12 g of 1-hydroxy-4,4-dimethyl-1-pentene-3-one potassium salt. 21.61 g of 1-hydroxy-4,4-dimethyl-1-pentene-3-one potassium salt was suspended to 150 ml of ethanol. 6.52 g of hydrazine hydrate was added to the suspension, and then refluxed for 7 hours. 50 ml of water was added to the reaction mixture which was cooled to room temperature, and the mixture was concentrated to 40 ml under reduced pressure. The concentrated solution was extracted by ethyl acetate. The organic layer was dried over anhydrous magnesium sulfate, filtered, and concentrated under reduced pressure. The residue was subjected to silica gel column chromatography to obtain 6.83 g of 3-t-butyl-1H-pyrazole.

$^1$H-NMR (CDCl$_3$, TMS, δ (ppm)): 1.34 (9H, s), 6.11 (1H, d), 7.47 (1H, d)

Reference Production Example 3-2

3-t-butyl-1H-pyrazole-1-ylmethanol

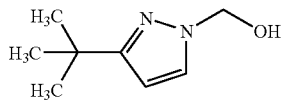

The mixture of 1.28 g of 3-t-butyl-1H-pyrazole, 0.66 g of paraformaldehyde and 0.3 g of triethylamine was stirred at 130° C. for 7 hours. After the reaction mixture was cooled to room temperature, acetone was added to the reaction mixture. The mixture was filtered. The filtrate was concentrated under reduced pressure. Hexane was added to the residue, and then crystalline was formed. The crystalline was collected to obtain 1.07 g of 3-t-butyl-1H-pyrazole-1-ylmethanol.

$^1$H-NMR (CDCl$_3$, TMS, δ (ppm)): 1.28 (9H, s), 5.50 (2H, s), 6.13 (1H, s), 7 .46 (1H, s)

Reference Production Example 3-3

3-t-butyl-1-(chloromethyl)-1H-pyrazole hydrochloride

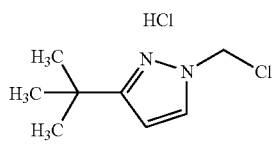

1.07 g of 3-t-butyl-1H-pyrazole-1-ylmethanol was dissolved to 140 ml of dichloromethane. 2 ml of thionyl chloride was added to the solution, followed by stirring at room temperature for overnight. The reaction mixture was concentrated under reduced pressure to obtain 1.66 g of 3-t-butyl-1-(chloromethyl)-1H-pyrazole hydrochloride.

$^1$H-NMR (CDCl$_3$, TMS, δ (ppm)): 6.25 (2H, s), 6.40 (1H, d), 7.69 (1H, d)

Reference Production Example 4-1

6,6-dimethyl-2,4,5,6-tetrahydrocyclopenta [c] pyrazole

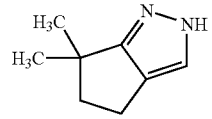

Under nitrogen atmosphere, mixture of 12.22 g of 2,2-dimethyl cyclopentanone and 6.01 g of methyl formate was cooled to 0° C., and then 6.74 g of potassium t-butoxide was added to the mixture over the period for 1 hour. During that, the temperature of the mixture was kept below 20° C. After that, the reaction mixture was stirred at room temperature for 18 hours. Diethyl ether was added to the reaction mixture, as a result, solid was produced. The solid was collected by filtration. The obtained solid was dried under reduced pressure to give 9.94 g of 1-hydroxymethylene-5,5-dimethyl cyclopentanone potassium salt. 9.94 g of 1-hydroxymethylene-5,5-dimethyl cyclopentanone potassium salt was suspended to 80 ml of ethanol. 2.80 g of hydrazine hydrate was added to the suspension, and then refluxed for 5 hours. 50 ml of water was added to the reaction mixture which was cooled to room temperature, and the mixture was concentrated to 40 ml under reduced pressure. The concentrated solution was extracted by ethyl acetate. The organic layer was dried over anhydrous magnesium sulfate, filtered, and concentrated under reduced pressure. The residue was subjected to silica gel column chromatography to obtain 1.68 g of 6,6-dimethyl-2,4,5,6-tetrahydrocyclopenta [c] pyrazole.

$^1$H-NMR (CDCl$_3$, TMS, δ (ppm)): 1.32 (6H, s), 2.23-2.28 (2H, t), 2.60-2.64 (2H, t), 7.11 (1H, s)

Reference Production Example 4-2

{6,6-dimethyl-5,6-dihydrocyclopenta [c] pyrazole-2 (4H)-yl} methanol

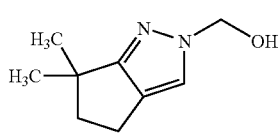

The mixture of 1.68 g of 6,6-dimethyl-2,4,5,6-tetrahydrocyclopenta [c] pyrazole, 0.41 g of paraformaldehyde and 0.2 g of triethylamine was stirred at 130° C. for 5 hours. After the reaction mixture was cooled to room temperature, acetone was added to the reaction mixture. The mixture was filtered. The filterate was concentrated under reduced pressure. Hexane was added to the residue, and then crystalline was formed. The crystalline was collected to obtain 0.31 g of {6,6-dimethyl-5,6-dihydrocyclopenta [c] pyrazole-2 (4H)-yl} methanol.

$^1$H-NMR (CDCl$_3$, TMS, δ (ppm)): 1.28 (6H, s), 2.18 (2H, t), 2.59 (2H, t), 5.44 (2H, s), 7.13 (1H, s)

Reference Production Example 4-3

1-(chloromethyl)-6,6-dimethyl-5,6-dihydrocyclopenta [c] pyrazole hydrochloride

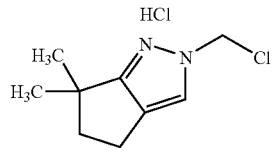

0.31 g of (6,6-dimethyl-5,6-dihydrocyclopenta [c] pyrazole-2 (4H)-yl) methanol was dissolved to 5 ml of dichloromethane. 1 ml of thionyl chloride was added to the solution, followed by stirring at room temperature for overnight. The reaction mixture was concentrated under reduced pressure to obtain 0.58 g of 1-(chloromethyl)-6,6-dimethyl-5,6-dihydrocyclopenta [c] pyrazole hydrochloride.

$^1$H-NMR (CDCl$_3$, TMS, δ (ppm)): 1.46 (6H, s), 2.33 (2H, t), 2.73 (2H, t), 6.18 (2H, s), 7.45 (1H, s)

Reference Production Example 5-1

3-(trifluoromethyl)-1H-pyrazole-1-ylmethanol

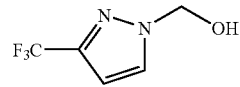

The mixture of 4.08 g of 3-(trifluoromethyl)-1H-pyrazole, 2.00 g of paraformaldehyde and 1 ml of triethylamine was stirred at 80° C. for 5 hours. After the reaction mixture was cooled to room temperature, acetone was added to the reaction mixture. The mixture was filtered. The filterate was concentrated under reduced pressure. Hexane was added to the residue, and then crystalline was formed. The crystalline was collected to obtain 4.31 g of 3-(trifluoromethyl)-1H-pyrazole-1-ylmethanol.

$^1$H-NMR (CDCl$_3$, TMS, δ (ppm)): 4.73 (1H, br. s), 5.58 (2H, s), 6.58 (1H, s), 7.66 (1H, s)

Reference Production Example 5-2

1-(chloromethyl)-3-(trifluoromethyl)-1H-pyrazole

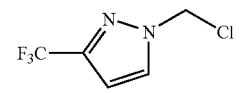

1.33 g of 3-(trifluoromethyl)-1H-pyrazole-1-ylmethanol was dissolved to 40 ml of dichloromethane. 2.7 ml of thionyl chloride was added to the solution, followed by stirring at room temperature for overnight. The reaction mixture was concentrated under reduced pressure to obtain 1.44 g of 1-(chloromethyl)-3-(trifluoromethyl)-1H-pyrazole.

$^1$H-NMR (CDCl$_3$, TMS, δ (ppm)): 5.88 (2H, s), 6.62 (1H, d), 7.68 (1H, d)

Reference Production Example 6-1

1-(hydroxymethyl)-3-formyl-1H-pyrazole

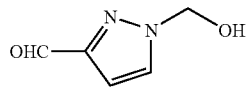

The mixture of 0.96 g of 3-formyl-1H-pyrazole, 0.60 g of paraformaldehyde and 0.3 ml of triethylamine was stirred at 100° C. for 5 hours. After the reaction mixture was cooled to room temperature, acetone was added to the reaction mixture. The mixture was filtered. The filterate was concentrated under reduced pressure to obtain 1.21 g of 1-(hydroxymethyl)-3-formyl-1H-pyrazole. The crude product was used for next process without purification.
$^1$H-NMR (CDCl$_3$, TMS, δ (ppm)): 5.63 (2H, s), 6.84 (1H, d), 7.67 (1H, d), 9.96 (1H, s)

Reference Production Example 6-2

1-(chloromethyl)-3-formyl-1H-pyrazole hydrochloride

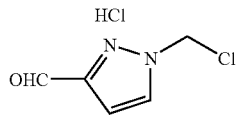

1.21 g of 1-(hydroxymethyl)-3-formyl-1H-pyrazole was dissolved to 50 ml of dichloromethane. 2.4 ml of thionyl chloride was added to the solution, followed by stirring at room temperature for overnight. The reaction mixture was concentrated under reduced pressure to obtain 1.57 g of 1-(chloromethyl)-3-formyl-1H-pyrazole hydrochloride.
$^1$H-NMR (CDCl$_3$, TMS, δ (ppm)): 5.92 (2H, s), 6.88 (1H, s), 7.67 (1H, s), 10.00 (1H, s)

Reference Production Example 7-1

3-cyano-1H-pyrazole

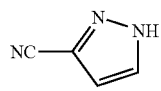

2.18 g of 3-formyl-1H-pyrazole was dissolved to 12 ml of pyridine. 1.58 g of hydroxylamine hydrochloride was added to the solution, followed by stirring at room temperature for 5 hours. The reaction mixture was concentrated under reduced pressure. 30 ml of acetic anhydride was added to the residue followed by stirring at 100° C. for 5 hours. After the reaction mixture was cooled to room temperature, it was concentrated under reduced pressure. 30 ml of ethanol was added to the residue, and then the mixture was stirred at 100° C. for 3 hours. After the reaction mixture was cooled to room temperature, it was concentrated under reduced pressure. The residue was subjected to silica gel column chromatography to obtain 0.86 g of 3-cyano-1H-pyrazole.
$^1$H-NMR (CDCl$_3$, TMS, δ (ppm)): 6.79 (1H, d), 7.75 (1H, d)

Reference Production Example 7-2

1-(hydroxymethyl)-3-cyano-1H-pyrazole

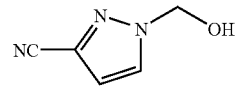

The mixture of 0.86 g of 3-cyano-1H-pyrazole and 0.55 g of paraformaldehyde was stirred at 130° C. for 7 hours. After the reaction mixture was cooled to room temperature, acetone was added to the reaction mixture. After the mixture was filtered, the filterate was concentrated under reduced pressure to obtain 0.89 g of 1-(hydroxymethyl)-3-cyano-1H-pyrazole.
$^1$H-NMR (DMSO-d$_6$, TMS, δ (ppm)): 5.54 (2H, s), 6.70 (1H, d), 7.72 (1H, d)

Reference Production Example 7-3

3-cyano-1-(chloromethyl)-1H-pyrazole

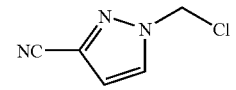

0.89 g of 1-(hydroxymethyl)-3-cyano-1H-pyrazole was dissolved to 30 ml of dichloromethane. 1.6 ml of thionyl chloride was added to the solution, followed by stirring at room temperature for overnight. The reaction mixture was concentrated under reduced pressure to obtain 1.00 g of 3-cyano-1-(chloromethyl)-1H-pyrazole.
$^1$H-NMR (CDCl$_3$, TMS, δ (ppm)): 5.87 (2H, s), 6.76 (1H, s), 7.72 (1H, s)

Reference Production Example 8-1

3-phenyl-1H-pyrazole-1-ylmethanol

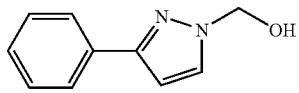

The mixture of 2.88 g of 3-phenyl-1H-pyrazole, 0.67 g of paraformaldehyde and 0.3 ml of triethylamine was stirred at 130° C. for 5 hours. After the reaction mixture was cooled to room temperature, acetone was added to the reaction mixture. After the mixture was filtered, hexane was added to the filterate to produce a crystal. The crystal was collected to obtain 2.64 g of 3-phenyl-1H-pyrazole-1-ylmethanol.

Reference Production Example 8-2

1-(chloromethyl)-3-phenyl-1H-pyrazole hydrochloride

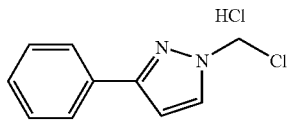

1.74 g of 3-phenyl-1H-pyrazole-1-ylmethanol was dissolved to 50 ml of dichloromethane. 3.4 ml of thionyl chloride was added to the solution, followed by stirring at room temperature for overnight. The reaction mixture was concentrated under reduced pressure. Hexane and chloroform was added to the residue to produce a crystal. The crystal was collected to obtain 2.01 g of 1-(chloromethyl)-3-phenyl-1H-pyrazole hydrochloride.

$^1$H-NMR (CDCl$_3$, TMS, δ (ppm)): 6.15 (2H, s), 6.76 (1H, d), 7.39-7.49 (3H, m), 7.76 (1H, d), 7.90-7.94 (2H, m)

Reference Production Example 9-1

4-bromo-3-i-propyl-1H-pyrazole

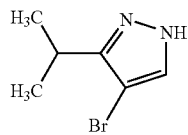

1.10 g of 3-i-propyl-1H-pyrazole was suspended in 20 ml of water, and 1.6 g of 50% aqueous solution of sodium hydroxide was added to it. The mixture was cooled to 0° C., and then 1.76 g of bromine was added to the mixture, followed by stirring at room temperature for 5 hours. The reaction mixture was extracted by ethyl acetate. The organic layer was washed with water, dried over anhydrous magnesium sulfate, filtered, and concentrated under reduced pressure. The residue was subjected to silica gel column chromatography to obtain 1.88 g of 4-bromo-3-i-propyl-1H-pyrazole.

$^1$H-NMR (CDCl$_3$, TMS, δ (ppm)): 1.31 (6H, d), 3.07-3.18 (1H, m), 7.49 (1H, s)

Reference Production Example 9-2

4-bromo-3-i-propyl-1H-pyrazole-1-ylmethanol

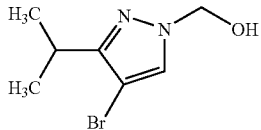

The mixture of 1.88 g of 4-bromo-3-i-propyl-1H-pyrazole, 0.60 g of paraformaldehyde and 0.10 g of triethylamine was stirred at 130° C. for 5 hours. After the reaction mixture was cooled to room temperature, acetone was added to the reaction mixture. The mixture was filtered, and the filtrate was concentrated under reduced pressure to obtain 1.29 g of 4-bromo-3-i-propyl-1H-pyrazole-1-ylmethanol.

$^1$H-NMR (CDCl$_3$, TMS, δ (ppm)): 1.26 (6H, d), 3.02-3.11 (1H, m), 5.43 (2H, s), 7.54 (1H, s)

Reference Production Example 9-3

4-bromo-3-i-propyl-1-(chloromethyl)-1H-pyrazole hydrochloride

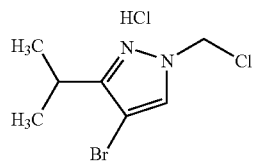

1.29 g of 4-bromo-3-i-propyl-1H-pyrazole-1-ylmethanol was dissolved to 20 ml of dichloromethane. 2 ml of thionyl chloride was added to the solution, followed by stirring at room temperature for overnight. The reaction mixture was concentrated under reduced pressure to obtain 1.28 g of 4-bromo-3-i-propyl-1-(chloromethyl)-1H-pyrazole hydrochloride.

$^1$H-NMR (CDCl$_3$, TMS, δ (ppm)): 1.29 (6H, d), 2.99-3.10 (1H, m), 5.75 (2H, s) 7.54 (1H, s)

Reference Production Example 10-1

4-bromo-3-t-butyl-1H-pyrazole

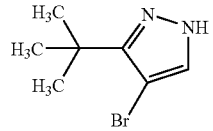

2.48 g of 3-t-butyl-1H-pyrazole was suspended in 35 ml of water, and 2.5 g of 50% aqueous solution of sodium hydroxide was added to it. The mixture was cooled to 0° C., and then 3.50 g of bromine was added to the mixture, followed by stirring at room temperature for 7 hours. The reaction mixture was extracted by ethyl acetate. The organic layer was washed with water dried over anhydrous magnesium sulfate, filtered, and concentrated under reduced pressure. The residue was subjected to silica gel column chromatography to obtain 3.14 of 4-bromo-3-t-butyl-1H-pyrazole.

$^1$H-NMR (CDCl$_3$, TMS, δ (ppm)): 1.45(9H, s), 7.48 (1H, s)

Reference Production Example 10-2

4-bromo-3-t-butyl-1H-pyrazole-1-ylmethanol

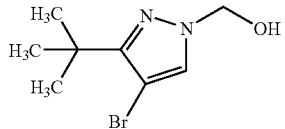

The mixture of 3.14 g of 4-bromo-3-t-butyl-1H-pyrazole, 0.93 g of paraformaldehyde and 0.11 g of triethylamine was stirred at 130° C. for 7 hours. After the reaction mixture was cooled to room temperature, acetone was added to the reaction mixture. The mixture was filtered. Hexane was added to the residue obtained by concentration of the filtrate under reduced pressure, as a result, a crystal was formed. The crystal was collected to obtain 3.79 g of 4-bromo-3-t-butyl-1H-pyrazole-1-ylmethanol.

$^1$H-NMR (CDCl$_3$, TMS, δ (ppm)): 1.37 (9H, s), 5.40 (2H, s), 7.55 (1H, s)

Reference Production Example 10-3

4-bromo-3-t-butyl-1-(chloromethyl)-1H-pyrazole hydrochloride

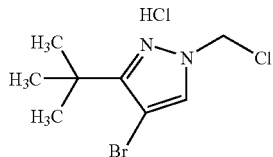

3.79g of 4-bromo-3-t-butyl-1H-pyrazole-1-ylmethanol was dissolved to 45 ml of dichloromethane. 3.4 ml of thionyl chloride was added to the solution, followed by stirring at room temperature for overnight. The reaction mixture was concentrated under reduced pressure. The solid obtained was washed with hexane and chloroform to obtain 3.69 g of 4-bromo-3-t-butyl-1-(chloromethyl)-1H-pyrazole hydrochloride.

$^1$H-NMR (CDCl$_3$, TMS, δ (ppm)): 1.40 (9H, s), 5.76 (2H, s), 7.56 (1H, s)

Reference Production Example 11-1

3-t-butyl-4-chloro-1H-pyrazole

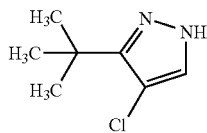

1.42 g of 3-t-butyl-1H-pyrazole was dissolved to 230 ml of chloroform. 1.55 g of N-chlorosuccinimide was added to the solution, followed by stirring at room temperature for overnight. The reaction mixture was concentrated under reduced pressure, and the residue was subjected to silica gel column chromatography to obtain 0.62 of 3-t-butyl-4-chloro-1H-pyrazole.

Reference Production Example 11-2

3-t-butyl-4-chloro-1H-pyrazole-1-methanol

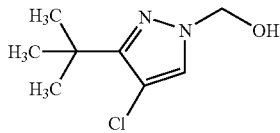

The mixture of 0.62 g of 3-t-butyl-4-chloro-1H-pyrazole, 0.24 g of paraformaldehyde and 0.10 g of triethylamine was stirred at 130° C. for 7 hours. After the reaction mixture was cooled to room temperature, acetone was added to the reaction mixture. The mixture was filtered. Hexane was added to the residue obtained by concentration of the filtrate under reduced pressure, as a result, a crystal was formed. The crystal was collected to obtain 0.82 g of 3-t-butyl-4-chloro-1H-pyrazole-1-ylmethanol.

$^1$H-NMR (CDCl$_3$, TMS, δ (ppm)): 1.38 (9H, s), 5.39 (2H, s), 7.51 (1H, s)

Reference Production Example 11-3

3-t-butyl-4-chloro-1-(chloromethyl)-1H-pyrazole hydrochloride

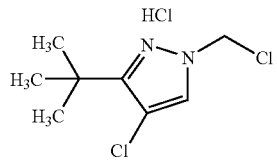

0.82 g of 3-t-butyl-4-chloro-1H-pyrazole-1-ylmethanol was dissolved to 45 ml of dichloromethane. 3.4 ml of thionyl chloride was added to the solution, followed by stirring at room temperature for overnight. The reaction mixture was concentrated under reduced pressure to obtain 0.98 g of 3-t-butyl-4-chloro-1-(chloromethyl)-1H-pyrazole hydrochloride.

$^1$H-NMR (CDCl$_3$, TMS, δ (ppm)): 1.39 (9H, s), 5.75 (2H, s), 7.52 (1H, s)

Reference Production Example 12-1

4-bromo-3-(trifluoromethyl)-1H-pyrazole

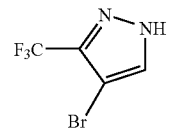

3.50 g of 3-(trifluoromethyl)-1H-pyrazole was suspended in 45 ml of water, and 3.2 g of 50% aqueous solution of sodium hydroxide was added to it. The mixture was cooled to 0° C., and then 3.20 g of bromine was added to the mixture, followed by stirring at room temperature for 7 hours. The reaction mixture was extracted by ethyl acetate. The organic layer was washed with water dried over anhydrous magnesium sulfate, filtered, and concentrated under reduced pressure. Hexane was added to the residue, as a result, a crystal was formed. The crystal was collected to obtain 3.38 g of 4-bromo-3-(trifluoromethyl)-1H-pyrazole.

$^1$H-NMR (CDCl$_3$, TMS, δ (ppm)): 7.72 (1H, s)

Reference Production Example 12-2

4-bromo-3-(trifluoromethyl)-1H-pyrazole-1-yl-methanol

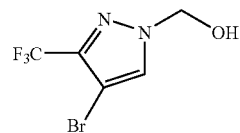

The mixture of 3.38 g of 4-bromo-3-(trifluoromethyl)-1H-pyrazole and 0.66 g of paraformaldehyde was stirred at 140°

C. for 5 hours. After the reaction mixture was cooled to room temperature, acetone was added to the reaction mixture. The mixture was filtered. Hexane was added to the residue obtained by concentration of the filtrate under reduced pressure, as a result, a crystal was formed. The crystal was collected to obtain 3.28 g of 4-bromo-3-(trifluoromethyl)-1H-pyrazole-1-ylmethanol.

$^1$H-NMR (CDCl$_3$, TMS, δ (ppm)): 5.52 (2H, s), 7.71 (1H, s)

Reference Production Example 12-3

4-bromo-1-(chloromethyl)-3-(trifluoromethyl)-1H-pyrazole

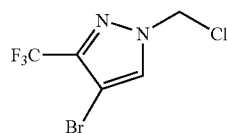

3.28 g of 4-bromo-3-(trifluoromethyl)-1H-pyrazole-1-ylmethanol was dissolved to 40 ml of dichloromethane. 2.9 ml of thionyl chloride was added to the solution, followed by stirring at room temperature for overnight. The reaction mixture was concentrated under reduced pressure. The obtained solid was washed with the mixture of hexane and chloroform to obtain 3.33 g of 4-bromo-1-(chloromethyl)-3-(trifluoromethyl)-1H-pyrazole.

$^1$H-NMR (CDCl$_3$, TMS, δ (ppm)): 5.82 (2H, s), 7.74 (1H, s)

Reference Production Example 13

1-(chloromethyl)-3,5-dimethylpyrazole hydrochloride

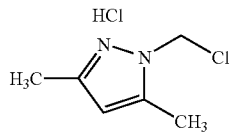

0.63 g of 3,5-dimethyl-1H-pyrazole-1-ylmethanol was dissolved to 25 ml of dichloromethane. 1.2 ml of thionyl chloride was added to the solution, followed by stirring at room temperature for overnight. The reaction mixture was concentrated under reduced pressure to obtain 0.93 g of 1-(chloromethyl)-3,5-dimethyl-1H-pyrazole hydrochloride.

$^1$H-NMR (CDCl$_3$, TMS, δ (ppm)): 2.49 (3H, s), 2.50 (3H, s), 6.20 (3H, s)

Reference Production Example 14-1

4-methyl-1H-pyrazole-1-ylmethanol

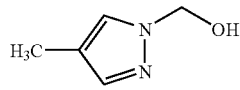

The mixture of 1.93 g of 4-methyl-1H-pyrazole, 0.97 g of paraformaldehyde and 0.4 ml of triethylamine was stirred at 130° C. for 5 hours. After the reaction mixture was cooled to room temperature, acetone was added to the reaction mixture. The mixture was filtered. Hexane was added to the residue obtained by concentration of the filtrate under reduced pressure, as a result, a crystal was formed. The crystal was collected to obtain 1.72 g of 4-methyl-1H-pyrazole-1-ylmethanol.

$^1$H-NMR (CDCl$_3$, TMS, δ(ppm)): 2.08 (3H,s), 5.43 (2H, s), 7.36 (2H, s)

Reference Production Example 14-2

1-(chloromethyl)-4-methyl-1H-pyrazole hydrochloride

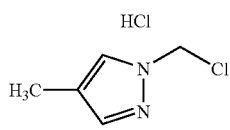

1.12 g of 4-methyl-1H-pyrazole-1-ylmethanol was dissolved to 50 ml of dichloromethane. 3.4 ml of thionyl chloride was added to the solution, followed by stirring at room temperature for overnight. The reaction mixture was concentrated under reduced pressure to obtain 1.61 g of 1-(chloromethyl)-4-methyl-1H-pyrazole hydrochloride.

Reference Production Example 15-1

4-chloro-1H-pyrazle-1-ylmethanol

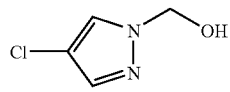

The mixture of 2.05g of 4-chloropyrazole, 0.66 g of paraformaldehyde and 0.11 g of triethylamine was stirred at 130° C. for 5 hours. After the reaction mixture was cooled to room temperature, acetone was added to the reaction mixture. The mixture was filtered. Hexane was added to the residue obtained by concentration of the filtrate under reduced pressure, as a result, a crystal was formed. The crystal was collected to obtain 2.73 g of 4-chloro-1H-pyrazole-1-ylmethanol.

$^1$H-NMR (CDCl$_3$, TMS, δ (ppm)): 5.45 (2H, s), 7.49 (1H, s), 7.60 (1H, s)

Reference Production Example 15-2

4-chloro-1-(chloromethyl)-1H-pyrazle hydrochloride

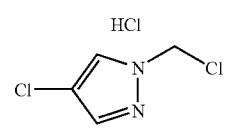

2.73 g of 4-chloro-1H-pyrazole-1-ylmethanol was dissolved to 20 ml of dichloromethane. 4.4 ml of thionyl chloride was added to the solution, followed by stirring at room temperature for overnight. The reaction mixture was concentrated under reduced pressure to obtain 2.90 g of 4-chloro-1-(chloromethyl)-1H-pyrazole hydrochloride.

$^1$H-NMR (CDCl$_3$, TMS, δ (ppm)): 5.81 (2H, s), 7.53 (1H, s), 7.60 (1H, s)

Reference Production Example 16-1

4-bromo-1H-pyrazle-1-ylmethanol

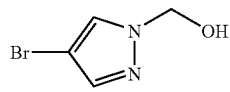

The mixture of 2.94 g of 4-bromo-1H-pyrazole, 0.66 g of paraformaldehyde and 0.3 ml of triethylamine was stirred at 130° C. for 4 hours. After the reaction mixture was cooled to room temperature, acetone was added to the reaction mixture. The mixture was filtered. Hexane was added to the residue obtained by concentration of the filtrate under reduced pressure, as a result, a crystal was formed. The crystal was collected to obtain 2.97 g of 4-bromo-1H-pyrazole-1-ylmethanol.

$^1$H-NMR (CDCl$_3$, TMS, δ (ppm)): 5.46 (2H, s), 7.53 (1H, s), 7.63 (1H, s)

Reference Production Example 16-2

4-bromo-1-(chloromethyl)-1H-pyrazle hydrochloride

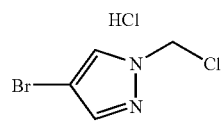

2.97 g of 4-bromo-1H-pyrazole-1-ylmethanol was dissolved to 100ml of dichloromethane. 5 ml of thionyl chloride was added to the solution, followed by stirring at room temperature for overnight. The reaction mixture was concentrated under reduced pressure to obtain 3.27 g of 4-bromo-1-(chloromethyl)-1H-pyrazole hydrochloride.

$^1$H-NMR (CDCl$_3$, TMS, δ (ppm)): 5.83 (2H, s), 7.57 (1H, s), 7.63(1H, s)

Reference Production Example 17-1

4-(trifluoromethyl)-1H-pyrazole

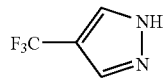

The above mentioned compound was produced by the method disclosed by Tetrahedron Letters 1829 (1996).

Reference Production Example 17-2

4-(trifluoromethyl)pyrazole-1-yl-1H-methanol

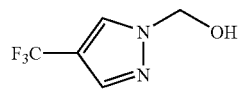

The mixture of 0.59 g of 4-(trifluoromethyl)-1H-pyrazole and 0.26 g of paraformaldehyde was stirred at 130° C. for 4 hours. After the reaction mixture was cooled to room temperature, acetone was added to the reaction mixture. The mixture was filtered. The residue was concentration under reduced pressure to obtain 0.60 g of 4-(trifluoromethyl)-1H-pyrazole-1-ylmethanol.

$^1$H-NMR (CDCl$_3$, TMS, δ (ppm)): 5.58 (2H, s), 7.77 (1H, s), 7.90 (1H, s)

Reference Production Example 17-3

1-(chloromethyl)-4-(trifluoromethyl)-1H-pyrazole

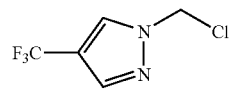

0.60 g of 4-(trifuluoromethyl)-1H-pyrazole-1-ylmethanol was dissolved to 10 ml of dichloromethane. 1 ml of thionyl chloride was added to the solution, followed by stirring at room temperature for overnight. The reaction mixture was concentrated under reduced pressure to obtain 0.60 g of 1-(chloromethyl)-4-trifluoromethyl-1H-pyrazole.

$^1$H-NMR (CDCl$_3$, TMS, δ (ppm)): 5.89 (2H, s), 7.80 (1H, s), 7.91 (1H, s)

Reference Production Example 18-1

4-methoxycarbonyl-1H-pyrazole

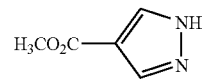

44.45 g of methyl 3,3-dimethoxypropionate and 45 ml of methyl formate was dissolved to 180 ml of dimethoxyethane. Under nitrogen atmosphere, 12.8 g of 60% sodium hydride was added to the solution keeping the temperature of the solution at 40 to 50° C. during addition. Then the mixture was stirred at room temperature for 18 hours. 180 ml of diethylether was added to the reaction mixture, as a result, a solid was formed. The solid was collected by filteration, followed by washing with 60 ml of diethylether. The obtained solid was dried under reduced pressure for overnight to obtain 49.41 g of methyl 2-(dimethoxymethyl)-3-hydroxy-acrylate sodium salt. 9.91 g of methyl 2-(dimethoxymethyl)-3-hydroxy-acrylate sodium salt was suspended to 100 ml of ethanol. 2.50 g of hydrazine hydrate was added to the suspension, followed by stirring at room temperature for 3 hours and at 80° C. for 1 hour. 100 ml of water was added to the reaction mixture which was cooled to room temperature. The mixture was concentrated under reduced pressure to about 100 ml. The concentrated solution was extracted by ethyl acetate. The organic layer was washed with saturated aqueous solution of sodium chloride, dried over anhydrous magnesium sulfate, filtered, and concentrated under reduced pressure. The residue was dissolved to ethyl acetate, activated carbon was added to it, and stirred for overnight. The suspension was filtered. The filtrate was concentrated under reduced pressure. The residue was recrystallized from hexane-ethyl acetate to obtain 1.40 g of 4-methoxycarbonyl-1H-pyrazole.

¹H-NMR (DMSO-d6 TMS,δ (ppm)): 3.74 (3H, s), 8.08 (2H, s), 13.43 (1H, s)

Reference Production Example 18-2

1-(hydroxymethyl)-4-methoxycarbonyl-1H-pyrazole

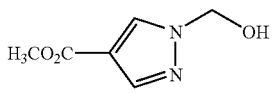

The mixture of 1.40 g of 4-methoxycarbonyl-1H-pyrazole, 0.37 g of paraformaldehyde and 0.11 g of triethylamine was stirred at 130° C. for 1 hour. 0.74 g of paraformaldehyde and 2 ml of triethylamine were added to the mixture and stirred at 130° C. for 2 hours. After the reaction mixture was cooled to room temperature, acetone was added. After the mixture was filtered, the filtrate was concentrated under reduced pressure. The residue was subjected to silica gel column chromatography to obtain 1.38 g of 1-(hydroxymethyl)-4-methoxycarbonyl-1H-pyrazole.
¹H-NMR (CDCl₃, TMS, δ (ppm)): 3.84 (3H, s), 5.53 (2H, s), 7.96 (1H, s), 8.08 (1H, s)

Reference Production Example 18-3

1-(chloromethyl)-4-methoxycarbonyl-1H-pyrazole

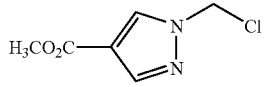

1.38 g of 1-(hydroxymethyl)-4-methoxycarbonyl-1H-pyrazole was dissolved to 10 ml of dichloromethane. 1 ml of thionyl chloride was added to the solution, followed by stirring at room temperature for overnight. The reaction mixture was concentrated under reduced pressure to obtain 1.59 g of 1-(chloromethyl)-4-methoxycarbonyl-1H-pyrazole.
¹H-NMR (CDCl₃, TMS, δ (ppm)): 3.85 (3H, s), 5.85 (2H, s), 7.98 (1H, s), 8.10 (1H, s)

Reference Production Example 19-1

1-(hydroxymethyl)-3-(trifluoromethyl)-4-ethyoxy-carbonyl-1H-pyrazole

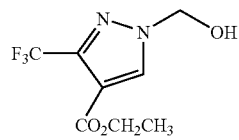

The mixture of 2.08 g of 3-(trifluoromethyl)-4-ethyoxy-carbonyl-1H-pyrazole and 0.66 g of paraformaldehyde was stirred at 150° C. for 4 hours. After the reaction mixture was cooled to room temperature, acetone was added. After the mixture was filtered, the filtrate was concentrated under reduced pressure to obtain 2.23 g of 1-(hydroxymethyl)-3-(trifluoromethyl)-4-ethoxycarbonyl-1H-pyrazole.
¹H-NMR (CDCl₃, TMS, δ (ppm)): 1.34 (3H, t), 4.30 (2H, q), 5.58 (2H, s), 8.21 (1H, s)

Reference Production Example 19-2

1-(chloromethyl)-3-(trifluoromethyl)-4-ethyoxycarbonyl-1H-pyrazole

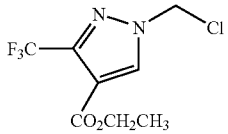

2.23 g of 1-(hydroxymethyl)-3-(trifluoromethyl)-4-ethyoxycarbonyl-1H-pyrazole was dissolved to 30 ml of dichloromethane. 1.4 ml of thionyl chloride was added to the solution, followed by stirring at room temperature for overnight. The reaction mixture was concentrated under reduced pressure to obtain 2.38 g of 1-(chloromethyl)-3-(trifluoromethyl)-4-ethoxycarbonyl-1H-pyrazole.
¹H-NMR (CDCl₃, TMS, δ (ppm)): 1.31 (3H, t), 4.31 (2H, q), 5.85 (2H, s), 8.20 (1H, s)

Reference Production Example 20

1-chloromethyl-1H-1,2,4-trizole hydrochloride

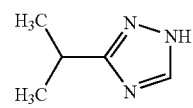

The compound above was produced by the method disclosed by JP S57-165374 A.
¹H-NMR (DMSO-d₆, TMS, δ (ppm)):6.26 (2H, s), 8.16 (1H, s), 8.85 (1H, s)

Reference Production Example 21-1

3-i-propyl-1H-1,2,4-triazole

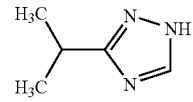

Above compound was produced in a similar manner as the method disclosed by JP H6-87839 A.
¹H-NMR (CDCl₃, TMS, δ (ppm)): 1.39 (6H, d), 3.14-3.74 (1H, m), 7.99 (1H, s)

Reference Production Example 21-2

3-i-propyl-1H-1,2,4-triazole 1-ylmethanol

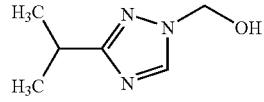

The mixture of 1.15 g of 3-i-propyl-1H-1,2,4-triazole, 0.94 g of paraformaldehyde and 0.14 g of triethylamine was stirred at 150° C. for 5 hours. After the reaction mixture was cooled to room temperature, acetone was added. The mixture was filtered. The filtrate was concentrated under reduced pressure. Hexane was added to the obtained residue, as a result, a crystal was formed. The crystal was collected to obtain 1.28 g of 3-i-propyl-1H-triazole-1-ylmethanol.

$^1$H-NMR (CDCl$_3$, TMS, δ (ppm)): 1.32 (6H, d), 3.04-3.12 (1H, m), 5.54 (2H, s), 8.14 (1H, s)

Reference Production Example 21-3

1-(chloromethyl)-3-i-propyl-1H-1,2,4-triazole hydrochloride

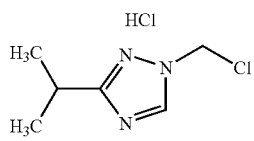

1.28 g of 3-i-propyl-1H-1,2,4-triazole1-ylmethanol was dissolved to 20 ml of dichloromethane, and 2 ml of thionyl chloride was added to the solution, followed by stirring at room temperature for 8 hours. The reaction mixture was concentrated under reduced pressure. Diethylether was added to the residue, as a result, a crystal was formed. The crystal was collected to obtain 1.58 g of 1-(chloromethyl)-3-i-propyl-1H-1,2,4-triazole hydrochloride.

Reference Production Example 22-1

3-t-butyl-1H-1,2,4-triazole

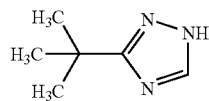

Above compound was produced by the method described JP H6-87839 A.

$^1$H-NMR (CDCl$_3$, TMS, δ (ppm)): 1.45 (9H, s), 8.25 (1H, s)

Reference Production Example 22-2

3-t-butyl-1H-1,2,4-triazole1-ylmethanol

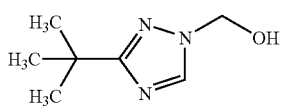

The mixture of 3.76 g of 3-t-butyl-1H-1,2,4-triazole, 1.00 g of paraformaldehyde and 0.3 ml of triethylamine was stirred at 150° C. for 5 hours. After the reaction mixture was cooled to room temperature, acetone was added. The mixture was filtered. The filtrate was concentrated under reduced pressure. Hexane was added to the obtained residue, as a result, a crystal was formed. The crystal was collected to obtain 1.38 g of 3-t-butyl-1H-triazole-1-ylmethanol.

$^1$H-NMR (CDCl$_3$, TMS, δ (ppm)): 1.37 (9H, s), 1.81 (1H, br. s), 5.55 (2H, s), 8.16 (1H, s)

Reference Production Example 22-3

3-t-butyl-1-(chloromethyl)-1H-1,2,4-triazole hydrochloride

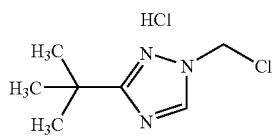

The mixture of 1.38 g of 3-t-butyl-1H-1,2,4-triazole1-yl-methanol and 2.7 ml of thionyl chloride was stirred under reflux condition for 3 hours. After the reaction mixture was cooled to room temperature, the reaction mixture was concentrated under reduced pressure. The residue was recrystallized from hexane to obtain 1.72 g of 3-t-butyl-1-(chloromethyl)-1H-1,2,4-triazole hydrochloride. $^1$H-NMR (CDCl$_3$, TMS, δ (ppm)): 1.36 (9H, s), 5.83 (2H, s), 8.17 (1H, s)

Reference Production Example 23-1

3-(1,1-dimethylpropyl)-1H-1,2,4-triazole

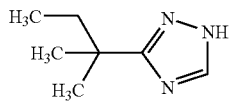

Above compound was produced in a similar manner as the method disclosed by JP H6-87839 A.

$^1$H-NMR (CDCl$_3$, TMS, δ (ppm)): 0.77 (3H, t), 1.40 (6H, s), 1.74 (2H, q), 7.98 (1H, s)

Reference Production Example 23-2

3-(1,1-dimethylpropyl)-1H-1,2,4-triazole1-ylmethanol

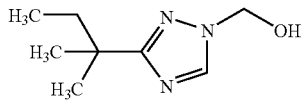

The mixture of 0.86 g of 3-(1,1-dimethylpropyl)-1H-1,2,4-triazole, 0.37 g of paraformaldehyde and 0.63 g of triethylamine was stirred at 150 ° C. for 5 hours. After the reaction mixture was cooled to room temperature, acetone was added. The mixture was filtered. The filtrate was concentrated under reduced pressure to obtain 1.10 g of 3-(1,1-dimethylpropyl)-1H-triazole-1-ylmethanol.

$^1$H-NMR (CDCl$_3$, TMS, δ (ppm)): 0.73 (3H, t), 1.33 (6H, s), 1.71 (2H, q), 5.54 (2H, s), 8.16 (1H, s)

Reference Production Example 23-3

1-(chloromethyl)-3-(1,1-dimethylpropyl)-1H-1,2,4-triazole hydrochloride

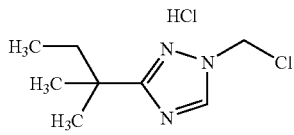

1.10 g of 3-(1,1-dimethylpropyl)-1H-1,2,4-triazole1-yl-methanol was dissolved to 18 ml of dichloromethane. 1.8 ml of thionyl chloride was added to the solution, followed by stirring at room temperature for 8 hours. The reaction mixture was concentrated under reduced pressure to obtain 1.47 g of 1-(chloromethyl)-3-(1,1-dimethylpropyl)-1H-1,2,4-triazole hydrochloride.

Reference Production Example 24-1

5-bromo-3-t-butyl-1H-1,2,4-triazole

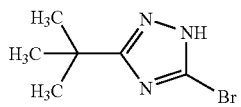

The mixture of 2.51 g of 3-t-butyl-1H-1,2,4-triazole, 35 ml of water and 2.5 ml of 50% aqueous solution of sodium hydroxide was cooled to 0° C., then 3.5 g of bromine was added to it. It was stirred at room temperature for 3 hours. The reaction mixture was extracted by ethyl acetate, dried over anhydrous sodium sulfate, and concentrated under reduced pressure. The residue was recrystallized from hexane to obtain 3.80 g of 5-bromo-3-t-butyl-1H-1,2,4-triazole.

$^1$H-NMR (CDCl$_3$, TMS, δ (ppm)): 1.41 (9H, s), 11.60 (1H, br. s)

Reference Production Example 24-2

5-bromo-3-t-butyl-1H-1,2,4-triazole1-ylmethanol

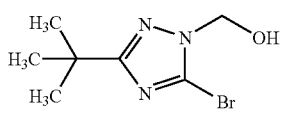

The mixture of 3.45 g of 5-bromo-3-t-butyl-1H-1,2,4-triazole, 0.61 g of paraformaldehyde and 0.17 g of triethylamine was stirred at 130 ° C. for 5 hours. After the reaction mixture was cooled to room temperature, acetone was added. The mixture was filtered. Hexane was added to the residue and filtered. The filtrate was concentrated under reduced pressure to obtain 2.88 g of 5-bromo-3-t-butyl-1H-1,2,4-triazole1-yl-methanol.

$^1$H-NMR (CDCl$_3$, TMS, δ (ppm)): 1.34 (9H, s), 5.55 (2H, s)

Reference Production Example 24-3

5-bromo-3-t-butyl-1-(chloromethyl)-1H-1,2,4-triazole hydrochloride

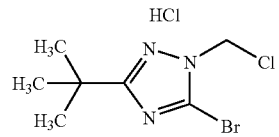

2.88 g of 5-bromo-3-t-butyl-1H-1,2,4-triazole 1-ylmethanol was dissolved to 100 ml of dichloromethane. 4.2 ml of thionyl chloride was added to the solution, followed by stirring at room temperature for 3 hours. The reaction mixture was concentrated under reduced pressure. Chloroform was added to the residue and filtered. The filtrate was concentrated under reduced pressure to obtain 2.03 g of 5-bromo-3-t-butyl-1-(chloromethyl)-1H-1,2,4-triazole hydrochloride.

$^1$H-NMR (CDCl$_3$, TMS, δ (ppm)): 1.35 (9H, s), 5.79 (2H, s)

Reference Production Example 25-1

3-(trifluoromethyl)-1H-1,2,4-triazole

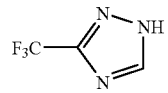

4.76 g of hydrazine hydrate was dissolved to 160 ml of ethanol, and it was cooled to 0° C. 14.21 g of ethyl 2,2,2-trifluoroacetate was dropped to it over the period of 30 minutes, followed by stirring at 0° C. for 1 hour. 9.89 g of formamidine acetic acid salt was added to the reaction mixture, followed by stirring at room temperature for 30 minutes. The reaction mixture was concentrated under reduced pressure. 200 ml of acetic acid was added to the residue, followed by stirring at 100° C. for 5 hours. The reaction mixture which was cooled to room temperature was concentrated under reduced pressure. Saturated aqueous solution of sodium hydrogen carbonate was added to the residue so as to be pH 6. And then it was extracted with ethyl acetate. The organic layer was dried over anhydrous sodium sulfate, and concentrated under reduced pressure. The residue was recrystallized from hexane to obtain 5.44 g of 3-(trifluoromethyl)-1H-1,2,4-triazole.

$^1$H-NMR (CDCl$_3$, TMS, δ (ppm)): 8.45 (1H, s), 12.47 (1H, br.s)

Reference Production Example 25-2

3-(trifluoromethyl)-1H-1,2,4-triazole 1-ylmethanol

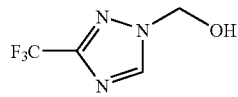

The mixture of 2.74 g of 3-(trifluoromethyl)-1H-1,2,4-triazole and 1.20 g of paraformaldehyde was stirred at 150° C. for 5 hours. After the reaction mixture was cooled to room temperature, acetone was added to the reaction mixture, and the mixture was filtered. The filtrate was concentrated. The residue was subjected to silica gel column chromatography to obtain 3.15 g of 3-(trifluoromethyl)-1H-1,2,4-triazole 1-ylmethanol.

$^1$H-NMR (CDCl$_3$, TMS, δ (ppm)): 4.04 (1H, t), 5.67 (2H, d), 8.37 (1H, s)

Reference Production Example 25-3

1-(chloromethyl)-3-(trifluoromethyl)-1H-1,2,4-triazole

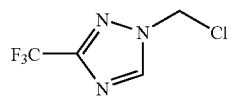

1.52 g of 3-(trifluoromethyl)-1H-1,2,4-triazole 1-ylmethanol was dissolved to 50 ml of dichloromethane, and 2.7 ml of thionyl chloride was added to the solution, followed by stirring at room temperature for overnight. The reaction mixture was concentrated under reduced pressure to obtain 1.36 g of 1-(chloromethyl)-3-(trifluoromethyl)-1H-1,2,4-triazole.

$^1$H-NMR (CDCl$_3$, TMS, δ (ppm)): 5.92 (2H, s), 8.44 (1H, s)

Reference Production Example 26-1

3-(pentafluoroethyl)-1H-1,2,4-triazole

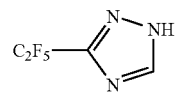

1.25 g of hydrazine hydrate was dissolved to 45 ml of ethanol, and it was cooled to 0° C. 5.38 g of ethyl 2,2,3,3,3-pentafluoropropionate was dropped to it over the period of 15 minutes, followed by stirring at 0° C. for 1 hour. 2.61 g of formamidine acetic acid salt was added to the reaction mixture, followed by stirring at room temperature for 30 minutes. The reaction mixture was concentrated under reduced pressure. 50 ml of acetic acid was added to the residue, followed by stirring at 100° C. for 5 hours. The reaction mixture was concentrated under reduced pressure. Saturated aqueous solution of sodium hydrogen carbonate was added to the residue so as to be around pH 6. And then it was extracted with ethyl acetate. The organic layer was dried over anhydrous sodium sulfate, and concentrated under reduced pressure. The residue was subjected to silica gel column chromatography to obtain 2.98 g of 3-pentafluoroethyl-1H-1,2,4-triazole.

$^1$H-NMR (CDCl$_3$, TMS, δ (ppm)): 8.47 (1H, s), 12.39 (1H, br. s)

Reference Production Example 26-2

3-(pentafluoroethyl)-1H-1,2,4-triazole 1-ylmethanol

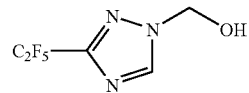

The mixture of 1.45 g of 3-(pentafluoroethyl)-1H-1,2,4-triazole and 0.46 g of paraformaldehyde was stirred at 150° C.

for 5 hours. After the reaction mixture was cooled to room temperature, acetone was added. The mixture was filtered. The filtrate was concentrated. Hexane was added to the residue, as a result, a crystal was formed. The crystal was collected to obtain 1.52 g of 3-(pentafluoroethyl)-1H-1,2,4-triazole 1-ylmethanol.

$^1$H-NMR (CDCl$_3$, TMS, δ (ppm)): 5.69 (2H, s), 8.41 (1H, s)

Reference Production Example 26-3

1-(chloromethyl)-3-(pentafluoroethyl)-1H-1,2,4-triazole

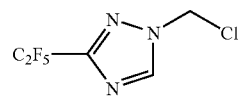

1.52 g of 3-(pentafluoroethyl)-1H-1,2,4-triazole 1-ylmethanol was dissolved to 50 ml of dichloromethane, and 2.7 ml of thionyl chloride was added to the solution, followed by stirring at room temperature for overnight. The reaction mixture was concentrated under reduced pressure to obtain 1.36 g of 1-(chloromethyl)-3-(pentafluoroethyl)-1H-1,2,4-triazole.

$^1$H-NMR (CDCl$_3$, TMS, δ (ppm)): 5.93 (2H, s), 8.44 (1H, s)

Reference Production Example 27-1

3-(pentafluoroethyl)-1H-pyrazole-1-ylmethanol

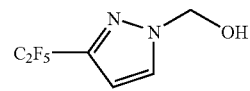

The mixture of 1.86 g of 3-(pentafluoroethyl)-1H-pyrazole and 0.60 g of paraformaldehyde was stirred at 130° C. for 5 hours. After the reaction mixture was cooled to room temperature, acetone was added. The mixture was filtered. The filtrate was concentrated under reduced pressure to obtain 1.98 g of 3-(pentafluoroethyl)-1H-pyrazole-1-ylmethanol.

$^1$H-NMR (CDCl$_3$, TMS, δ (ppm)): 4.54 (1H, br. s), 5.58 (2H, d), 6.60 (1H, d), 7.68 (1H, d)

Reference Production Example 27-2

1-(chloromethyl)-3-(pentafluoroethyl)-1H-pyrazole

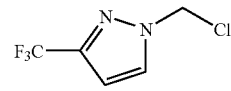

1.98 g of 3-(pentafluoroethyl)-1H-pyrazole-1-ylmethanol was dissolved to 20 ml of dichloromethane. 1.5 ml of thionyl chloride was added to the solution, followed by stirring at room temperature for overnight. The reaction mixture was concentrated under reduced pressure to obtain 2.01 g of 1-(chloromethyl)-3-(pentafluoroethyl)-1H-pyrazole.

$^1$H-NMR (CDCl$_3$, TMS, δ (ppm)): 5.89 (2H, s), 6.65 (1H, d), 7.71 (1H, d)

Reference Production Example 28-1

4-bromo-3-(pentafluoroethyl)-1H-pyrazole

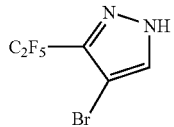

9.30 g of 3-(pentafluoroethyl)-1H-pyrazole was suspended to 90 ml of water, and 6.0 g of 50% aqueous solution of sodium hydroxide was added to the suspension. The mixture was cooled to 0° C., then 8.79 g of bromine was added to the mixture, followed by stirring at room temperature for 7 hours. The reaction mixture was extracted by ethyl acetate. The organic layer was washed with water, dried over anhydrous magnesium salfate, filtered, and concentrated under reduced pressure to obtain 13.72 g of 4-bromo-3-(pentafluoroethyl)-1H-pyrazole.

$^1$H-NMR (CDCl$_3$, TMS, δ (ppm)): 7.71 (1H, s)

Reference Production Example 28-2

4-bromo-3-(pentafluoroethyl)-1H-pyrazole-1-yl-methanol

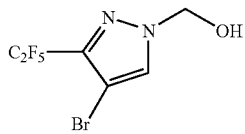

The mixture of 13.72 g of 4-bromo-3-(pentafluoroethyl)-1H-pyrazole and 3.00 g of paraformaldehyde was stirred at 130° C. for 5 hours. After the reaction mixture was cooled to room temperature, acetone was added. The mixture was filtered. The filtrate was concentrated under reduced pressure. Hexane was added to the filtrate, as a result, a crystal was formed. The crystal was collected to obtain 7.69 g of 4-bromo-3-(pentafluoroethyl)-1H-pyrazole-1-ylmethanol.

$^1$H-NMR (CDCl$_3$, TMS, δ (ppm)): 3.53 (1H, br. s), 5.54 (2H, s), 7.73 (1H, s)

Reference Production Example 28-3

4-bromo-1-(chloromethyl)-3-(pentafluoroethyl)-1H-pyrazole

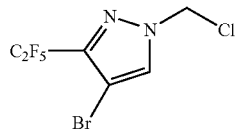

6.49 g of 4-bromo-3-(pentafluoroethyl)-1H-pyrazole-1-ylmethanol was dissolved to 60 ml of dichloromethane. 3.2 ml of thionyl chloride was added to the solution, followed by stirring at room temperature for overnight. The reaction mixture was concentrated under reduced pressure to obtain 6.84 g of 4-bromo-1-(chloromethyl)-3-(pentafluoroethyl)-1H-pyrazole.

$^1$H-NMR (CDCl$_3$, TMS, δ (ppm)): 5.82 (2H, s), 7.75 (1H, s)

Reference Production Example 29-1

4-(trifluoromethyl)-1H-imidazole-1-ylmethanol

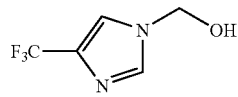

The mixture of 1.80 g of 4-(trifluoromethyl)-1H-imidazole, 0.78 g of paraformaldehyde was stirred at 140° C. for 4 hours. After the reaction mixture was cooled to room temperature, acetone was added. The mixture was filtered, and then the filtrate was concentrated under reduced pressure to obtain 2.16 g of 4-(trifluoromethyl)-1H-imidazole-1-yl-methanol.

$^1$H-NMR (CDCl$_3$, TMS, δ (ppm)): 5.39 (2H, d), 7.44 (1H, s), 7.61 (1H, s)

Reference Production Example 29-2

1-(chloromethyl)-4-(trifluoromethyl)-1H-imidazole hydrochloride

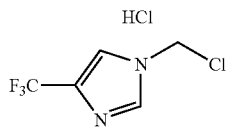

2.16 g of 4-(trifluoromethyl)-1H-imidazole-1-ylmethanol was dissolved to 40 ml of dichloromethane. 1.9 ml of thionyl chloride was added to the solution, followed by stirring at room temperature for overnight. The reaction mixture was concentrated under reduced pressure to obtain 2.90 g of 1-(chloromethyl)-4-(trifluoromethyl)-1H-pyrazole hydrochloride.

$^1$H-NMR (CDCl$_3$, TMS, δ (ppm)): 6.12 (2H, s), 8.10 (1H, s), 8.16 (1H, s)

Reference Production Example 30-1

3-cyano-1H-indole-1-ylmethanol

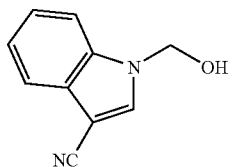

The mixture of 1.42 g of 3-cyano-1H-indole, 0.60 g of paraformaldehyde and 0.1 g of triethylamine was stirred at 130 ° C. for 1 hour. After the reaction mixture was cooled to room temperature, acetone was added to the reaction mixture. The mixture was filtered. The filtrate was concentrated under reduced pressure. The residue was subjected to silica gel column chromatography to obtain 1.69 g of 3-cyano-1H-indole-1-ylmethanol.

$^1$H-NMR (CDCl$_3$, TMS, δ (ppm)): 3.73 (1H, br. s), 5.64 (2H, d), 7.29-7.39 (2H, m), 7.56-7.59 (1H, m), 7.71-7.75 (2H, m)

Reference Production Example 30-2

1-(chloromethyl)-3-cyano-1H-indole

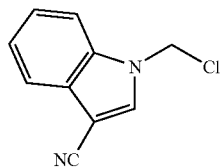

1.69 g of 3-cyano-1H-indole-1-ylmethanol was dissolved to 30 ml of dichloromethane. 1.4 ml of thionyl chloride was added to the solution, followed by stirring at room temperature for 3 hours. The reaction mixture was concentrated under reduced pressure to obtain 1.70 g of 1-(chloromethyl)-3-cyano-1H-indole.

$^1$H-NMR (DMSO-$d_6$, TMS, δ (ppm)): 6.44 (2H, s), 7.34-7.48 (2H, m), 7.64-7.74 (1H, m), 7.83 (1H, d), 8.47 (1H, s)

Reference Production Example 31-1

3-formyl-1H-indole-1-ylmethanol

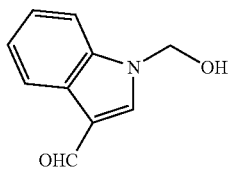

The mixture of 5.81 g of 3-formyl-1H-indole, 1.80 g of paraformaldehyde and 0.40 g of triethylamine was stirred at 120° C. for 3 hours. After the reaction mixture was cooled to room temperature, acetone was added to the reaction mixture. The mixture was filtered, and then the filtrate was concentrated under reduced pressure. The residue was subjected to silica gel column chromatography to obtain 3.08 g of 3-formyl-1H-indole-1-ylmethanol.

$^1$H-NMR (DMSO-$d_6$, TMS, δ (ppm)): 5.61 (2H, d), 6.78 (1H, t), 7.21-7.34 (2H, m), 7.49 (1H, d), 8.08 (1H, d), 8.34 (1H, s), 9.94 (1H, s)

Reference Production Example 31-2

1-(chloromethyl)-3-formyl-1H-indole

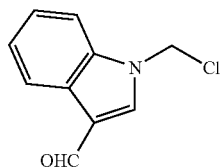

3.08 g of 3-formyl-1H-indole-1-ylmethanol was dissolved to 60 ml of dichloromethane. 2.5 ml of thionyl chloride was added to the solution, followed by stirring at room temperature for 3 hours. The reaction mixture was concentrated under reduced pressure to obtain 3.02 g of 1-(chloromethyl)-3-formyl-1H-indole.

$^1$H-NMR (CDCl$_3$, TMS, δ (ppm)): 5.99 (2H, s), 7.35-7.52 (3H, m), 7.81 (1H, s), 7.83 (1H, d), 8.32 (1H, d), 10.05 (1H, s)

Reference Production Example 32-1

3-(trifluoroacetyl)-1H-indole-1-ylmethanol

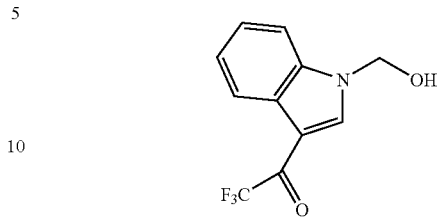

The mixture of 4.80 g of 3-(trifluoroacetyl)-1H-indole, 1.35 g of paraformaldehyde and 0.10 g of triethylamine was stirred at 130° C. for 2 hours. After the reaction mixture was cooled to room temperature, acetone was added to the reaction mixture. The mixture was filtered, and then the filtrate was concentrated under reduced pressure. The residue was subjected to silica gel column chromatography, and hexane was added to the residue, as a result, a crystal was formed. The crystal was collected to obtain 5.36 g of 3-(trifluoroacetyl)-1H-indole-1-ylmethanol.

$^1$H-NMR (DMSO-$d_6$, TMS, δ (ppm)): 5.71 (2H, d), 6.92 (1H, t), 7.36-7.43 (2H, m), 7.76 (1H, d), 8.19 (1H, d), 8.31 (1H, s)

Reference Production Example 32-2

1-(chloromethyl)-3-(trifluoroacetyl)-1H-indole

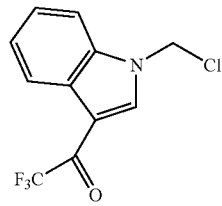

5.36 g of 3-(trifluoroacetyl)-1H-indole-1-ylmethanol was dissolved to 60 ml of dichloromethane. 2.5 ml of thionyl chloride was added to the solution, followed by stirring at room temperature for 3 hours. The reaction mixture was concentrated under reduced pressure and the residue was recrystallized from hexane-chloroform to obtain 3.79 g of 1-(chloromethyl)-3-(trifluoroacetyl)-1H-indole.

$^1$H-NMR (CDCl$_3$, TMS, δ (ppm)): 6.00 (2H, s), 7.30-7.57 (3H, m), 8.05 (1H, s), 8.39-8.41 (1H, m)

Reference Production Example 33-1

2-(4-methoxybenzyl)-4-thiocyanato-2H-pyrazole-3-ylamine

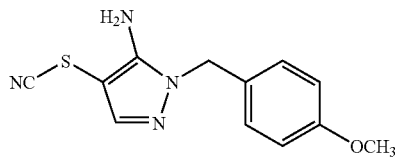

3.89 g of potassium thiocyanate was suspended to 40 ml of methanol. Under nitrogen atmosphere, this suspension was cooled to −78° C. 1.76 g of bromine which was dissolved to 40 ml of methanol was dropped to it during the period for 30 minutes, followed by stirring for 30 minutes. Then 2.03 g of 2-(4-methoxybenzyl)-2H-pyrazole-3-ylamine which was dissolved to 10 ml of methanol was dropped to it during the period for 10 minutes, followed by stirring at −78° C. for 1 hour and at room temperature for 8 hours. The reaction mixture was concentrated under reduced pressure. Water was added to the residue, and extracted with ethyl acetate. The organic layer was dried over anhydrous sodium sulfate, and then concentrated. The residue was subjected to silica gel column chromatography to obtain 1.54 g of 2-(4-methoxybenzyl)-4-thiocyanato-2H-pyrazole-3-ylamine.

$^1$H-NMR (DMSO-$d_6$, TMS, δ (ppm)): 3.72 (3H, s), 5.07 (2H, s), 6.37 (2H, b. s.), 6.87 (2H, d), 7.14 (2H, d), 7.42 (1H, s)

Reference Production Example 33-2

4-{[5-amino-1-(4-methoxybenzyl)-1H-pyrazole-4-yl]dithio}-1-(4-methoxybenzyl)-1H-pyrazole-5-amine

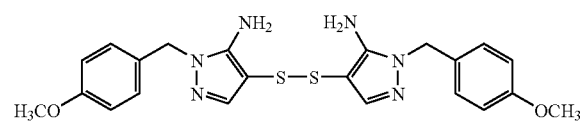

1.42 g 2-(4-methoxybenzyl)-4-thiocyanato-2H-pyrazole-3-ylamine was added to 20 ml of 10% aqueous solution of sodium hydroxide, and then the mixture was refluxed for 2 hours. The reaction mixture was cooled to room temperature, as a result, a crystal was formed. The crystal was collected by filtration. The crystal was washed with 30 ml of water for three times. The crystal was dried under reduced pressure to obtain 1.27 g of 4-{[5-amino-1-(4-methoxybenzyl)-1H-pyrazole-4-yl]dithio}-1-(4-methoxybenzyl)-1H-pyrazole-5-amine.

$^1$H-NMR (DMSO-$d_6$, TMS, δ (ppm)): 3.71 (6H, s), 5.07 (4H, s), 5.73 (4H, b. s.), 6.83 (4H, d), 6.98 (2H, s), 7.07 (4H, d)

Reference Production Example 33-3

4-{[dichlorofluoromethyl]thio}-1-(4-methoxybenzyl)-1H-pyrazole-5-amine

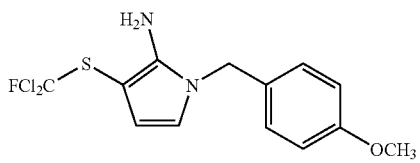

1.58 g of 4-{[5-amino-1-(4-methoxybenzyl)-1H-pyrazole-4-yl]dithio}1-(4-methoxybenzyl)-1H-pyrazole-5-amine was dissolved to 20 ml of N,N-dimethylformamide. 20 ml of water, 1.42 g of sodium hydrogen carbonate and 2.93 g of sodium hydrosulfite were added to the solution under ice-cooling. 5.28 g of trichlorofluoromethane was added to the mixture, followed by stirring at room temperature for 15 hours. Water was added to the reaction mixture, and extracted with ethyl acetate. The organic layer was washed with water, dried over sodium sulfate, and filtered. The filtrate was concentrated under reduced pressure. The residue was subjected to silica gel column chromatography to obtain 1.04 g of 4-{[dichlorofluoromethyl]thio}-1-(4-methoxybenzyl)-1H-pyrazole-5-amine.

$^1$H-NMR (CDCl$_3$, TMS, δ (ppm)): 3.79 (3H, s), 3.99 (2H, b. s.), 5.16 (2H, s), 6.86 (2H, d), 7.11 (2H, d), 7.52 (1H, s)

Reference Production Example 33-4

4-{[dichlorofluoromethyl]thio}-1-(4-methoxybenzyl)-1H-pyrazole

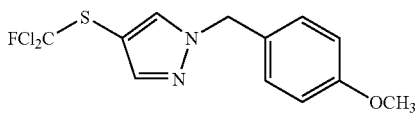

1.04 g of 4-{[dichlorofluoromethyl]thio}-1-(4-methoxybenzyl)-1H-pyrazole-5-amine was dissolved to 20 ml of tetrahydrofuran. 1.55 g of t-butyl nitrite was added to the solution, followed by reflux for 3 hours. After the reaction mixture was cooled to room temperature, water was added to the reaction mixture, and extracted with diethyl ether. The organic layer was washed with water, dried over sodium sulfate, and filtered. The filtrate was concentrated under reduced pressure. The residue was subjected to silica gel column chromatography to obtain 0.94 g of 4-{[dichlorofluoromethyl]thio}-1-(4-methoxybenzyl)-1H-pyrazole.

$^1$H-NMR (CDCl$_3$, TMS, δ (ppm)): 3.81 (3H, s), 5.27 (2H, s), 6.89 (2H, d), 7 .19 (2H, d), 7.60 (1H, s), 7.72 (1H, s)

Reference Production Example 33-5

4-{[dichlorofluoromethyl]thio}-1H-pyrazole

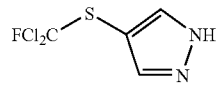

1.04 g of 4-{[dichlorofluoromethyl]thio}-1-(4-methoxybenzyl)-1H-pyrazole was dissolved to 6 ml of trifluoroacetic acid, followed by stirring at 65° C. for 3 hours. After the reaction mixture was cooled to room temperature, it was added to saturated aqueous solution of sodium hydrogen carbonate. The mixture was extracted with ethyl acetate. The organic layer was dried over anhydrous sodium sulfate, and filtered. The filtrate was concentrated under reduced pressure. The residue was subjected to silica gel column chromatography to obtain 0.19 g of 4-{[dichlorofluoromethyl]thio}-1H-pyrazole.

$^1$H-NMR (CDCl$_3$, TMS, δ (ppm)): 7.88 (2H, s)

Reference Production Example 33-6

4-{[dichlorofluoromethyl]thio}-1H-pyrazole-1-yl-methanol

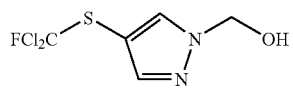

0.19 g of 4-{[dichlorofluoromethyl]thio}-1H-pyrazole was dissolved to 5 ml of tetrahydrofuran. 5 ml of formaldehyde 36% in water and 0.1 ml of tetrabutylammonium hydroxide 10% in water were added to the solution, followed by stirring at room temperature for 4 hours. Water was added to the reaction mixture, and extracted with MTBE. The organic layer was washed with water, dried over anhydrous magnesium sulfate, and filtered. The filtrate was concentrated under reduced pressure. The residue was subjected to silica gel column chromatography to obtain 0.22 g of 4-{[dichlorofluoromethyl]thio}-1H-pyrazole-1-ylmethanol.

$^1$H-NMR (CDCl$_3$,TMS,δ (ppm)): 5.57 (2H, s), 7.77 (1H, s), 7.90 (1H, s)

Reference Production Example 33-7

1-(chloromethyl)-4-{[dichlorofluoromethyl]thio}-1H-pyrazole

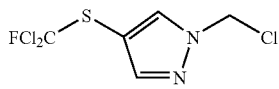

0.22 g of 4-{[dichlorofluoromethyl]thio}-1H-pyrazole-1-ylmethanol was dissolved to 10 ml of chloroform. 0.3 ml of thionyl chloride was added to the solution, and refluxed for 4 hours. The reaction mixture was concentrated under reduced pressure to obtain 0.21 g of 1-(chloromethyl)-4-{[dichloro(fluoro)methyl]thio}-1H-pyrazole.

$^1$H-NMR (CDCl$_3$, TMS, δ (ppm)): 5.88 (2H, s), 7.79 (1H, s), 7.92 (1H, s)

Reference Production Example 34-1

3-{[dichlorofluoromethyl]thio}-1H-indole-1-yl-methanol

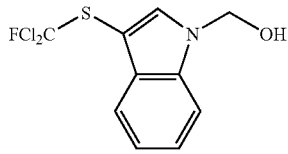

0.50 g of 3-{[dichlorofluoromethyl]thio}-1H-indole was dissolved to 10 ml of tetrahydrofuran. 10 ml of formaldehyde 36% in water and 0.4 ml of tetrabutylammonium hydroxide 10% in water were added to the solution, followed by stirring at room temperature for 30 minutes. Water was added to the reaction mixture, and extracted with MTBE. The organic layer was washed with water, dried over anhydrous magnesium sulfate, and filtered. The filtrate was concentrated under reduced pressure to obtain 0.54 g of 3-{[dichlorofluoromethyl]thio}-1H-indole-1-ylmethanol.

$^1$H-NMR (DMSO-d$_6$, TMS, δ (ppm)): 5.61 (2H, d) 6.73 (1H, t) 7.23-7.33 (2H, m), 7.66-7.70 (2H, m), 8.04 (1H, s)

Reference Production Example 34-2

1-(chloromethyl)-3-{[dichlorofluoromethyl]thio}-1H-indole

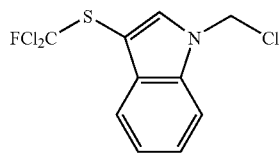

0.54 g of 3-{[dichlorofluoromethyl]thio}-1H-indole-1-yl-methanol was dissolved to 10 ml of chloroform. 0.3 ml of thionyl chloride was added to the solution, and refluxed for 4 hours. The reaction mixture was concentrated under reduced pressure to obtain 0.61 g of 1-(chloromethyl)-3-{[dichlorofluoromethyl]thio}-1H-indole.

Reference Production Example 35

1-chloromethyl-3-nitro-1H-pyrole

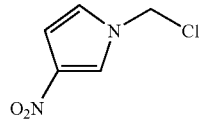

840 mg of 3-nitro-1H-pyrole, 15 ml of tetrahydrofuran and 15 ml of formaldehyde 36% in water were mixed. 0.5 ml of tetrabutylammonium hydroxide 10% in water was added at room temperature, followed by stirring at room temperature for 30 minutes. The reaction mixture was poured into ice-water, and extracted with ethyl acetate. The organic layer was washed with saturated aqueous sodium chloride solution, dried over anhydrous magnesium sulfate, and filtered. The filtrate was concentrated under reduced pressure to obtain 1-hydroxymethyl-3-nitro-1H-pyrole.

The obtained 1-hydroxymethyl-3-nitro-1H-pyrole was dissolved to 3 ml of chloroform, and 3 ml of thionyl chloride was added, followed by stirring at room temperature for 1 hour. After the reaction mixture was cooled to 0° C., it was poured into ice-water. The mixture was extracted with ethyl acetate. The organic layer was washed with saturated aqueous solution of sodium hydrogen carbonate, dried over anhydrous magnesium sulfate, and filtered. The filtrate was concentrated under reduced pressure. The residue was subjected to silica gel column chromatography to obtain 620 mg of 1-chloromethyl-3-nitro-1H-pyrole.

$^1$H-NMR (CDCl$_3$, TMS, δ (ppm)): 5.63 (2H, s), 6.77-6.78 (2H, m), 7.68-7.69 (1H, m)

Reference Production Example 36

1-chloromethyl-3-cyano-4-trifluoromethyl-1H-pyrole

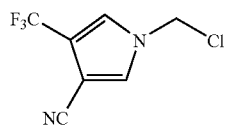

585 mg of 3-cyano-4-trifluoromethyl-1H-pyrole, 10 ml of tetrahydrofuran and 10 ml of formaldehyde 36% in water were mixed. 0.1 ml of tetrabutylammonium hydroxide 10% in water was added to the mixture at room temperature, followed by stirring at room temperature for 30 minutes. The reaction mixture was poured into ice-water, and extracted with ethyl acetate. The organic layer was washed with saturated aqueous sodium chloride solution, dried over anhydrous magnesium sulfate, and filtered. The filtrate was concentrated under reduced pressure to obtain 1-hydroxymethyl-3-cyano-4-trifluoromethyl-1H-pyrole.

The obtained 1-hydroxymethyl-3-cyano-4-trifluoromethyl-1H-pyrole was dissolved to 3 ml of chloroform, and 3 ml of thionyl chloride was added, followed by stirring at room temperature for 1 hour. After the reaction mixture was cooled to 0° C., it was poured into ice-water. The mixture was extracted with ethyl acetate. The organic layer was washed with saturated aqueous solution of sodium hydrogen carbonate, dried over anhydrous magnesium sulfate, and filtered. The filtrate was concentrated under reduced pressure to obtain 800 mg of 1-chloromethyl-3-cyano-4-trifluoromethyl-1H-pyrole.

$^1$H-NMR (CDCl$_3$, TMS, δ (ppm)): 5.62 (2H, s), 7.21 (1H, d), 7.39 (1H, d)

Reference Production Example 37

1-chloromethyl-4-trifluoromethyl-3-ethoxycarbony-1H-pyrole

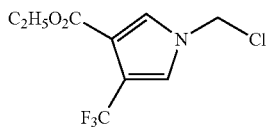

207 mg of 4-trifluoromethyl-3-ethoxycarbonyl-1H-pyrole, 5 ml of tetrahydrofuran and 5 ml of formaldehyde 36% in water were mixed. 0.2 ml of tetrabutylammonium hydroxide 10% in water was added to the mixture at room temperature, followed by stirring at room temperature for 10 minutes. The reaction mixture was poured into ice-water, and extracted with ethyl acetate. The organic layer was washed with saturated aqueous sodium chloride solution, dried over anhydrous magnesium sulfate, and filtered. The filtrate was concentrated under reduced pressure to obtain crude product of 1-hydroxymethyl-4-trifluoromethyl-3-ethoxycarbonyl-1H-pyrole.

The obtained 1-hydroxymethyl-4-trifluoromethyl-3-ethoxycarbonyl-1H-pyrole was dissolved to 3 ml of chloroform, and 4 ml of thionyl chloride was added, followed by refluxing for 30 minutes. After the reaction mixture was cooled to 0° C., it was poured into ice-water. The mixture was extracted with ethyl acetate. The organic layer was washed with saturated aqueous solution of sodium hydrogen carbonate, dried over anhydrous magnesium sulfate, and filtered. The filtrate was concentrated under reduced pressure to obtain 225 mg of 1-chloromethyl-4-trifluoromethyl-3-ethoxycarbonyl-1H-pyrole.

$^1$H-NMR (CDCl$_3$, TMS, δ (ppm)): 1.35 (3H, t), 4.31 (2H, q), 5.64(2H, s), 7 .17 (1H, d), 7.51 (1H, d)

Reference Production Example 38

1-chloromethyl-3-cyano-1H-pyrole

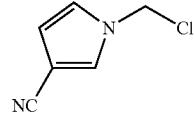

670 mg of 3-cyano-1H-pyrole, 10 ml of tetrahydrofuran and 10 ml of formaldehyde 36% in water were mixed. 0.1 ml of tetrabutylammonium hydroxide 10% in water was added at room temperature, followed by stirring at room temperature for 30 minutes. The reaction mixture was poured into ice-water, and extracted with ethyl acetate. The organic layer was washed with saturated aqueous sodium chloride solution, dried over anhydrous magnesium sulfate, and filtered. The filtrate was concentrated under reduced pressure to obtain 1-hydroxymethyl-3-cyano-1H-pyrole.

The obtained 1-hydroxymethyl-3-cyano-1H-pyrole was dissolved to 3 ml of chloroform, and 2 ml of thionyl chloride was added, followed by stirring at room temperature for 1 hour. After the reaction mixture was cooled to 0° C., it was poured into ice-water. The mixture was extracted with ethyl acetate. The organic layer was washed with saturated aqueous solution of sodium hydrogen carbonate, dried over anhydrous magnesium sulfate, and filtered. The filtrate was concentrated under reduced pressure and subjected to silica gel column chromatography to obtain 290 mg of 1-chloromethyl-3-cyano-1H-pyrole.

$^1$H-NMR (CDCl$_3$, TMS, δ (ppm)): 5.66 (2H, s), 6.46-6.47 (1H, m), 6.84 (1H, d), 7.32-7.33 (1H, m)

Formulation Examples are exemplified below. In addition, "part" means part by weight. The compounds of the present invention are designated by their compound numbers shown above.

Formulation Example 1

9 parts of each of the compounds of the present invention (1) to (48) are dissolved in 37.5 parts of xylene and 37.5 parts of dimethylformamide, and 10 parts of polyoxyethylene styryl phenyl ether and 6 parts of calcium dodecylbenzenesulfonate are added thereto, followed by stirring and mixing well, to give an emulsifiable concentrate for each compound.

Formulation Example 2

To 40 parts of each of the compounds of the present invention (1) to (48) are added 5 parts of SORPOL 5060 (registered trade name for TOHO KAGAKU KOGYO), followed by mixing well. To the mixture are added 32 parts of CARPLEX #80 (registered trade name for SHIONOGI & Co., synthetic hydrated silicone oxide fine powder) and 23 parts of 300 mesh diatomaceous earth, followed by mixing with a juice mixer, to give a wettable powder for each compound.

Formulation Example 3

To 3 parts of each of the compound of the present invention (1) to (48) are added 5 parts of synthetic hydrated silicon oxide fine powder, 5 parts of sodium dodecylbenzenesulfonate, 30 parts of bentonite, and 57 parts of clay, followed by stirring and mixing well. Then an appropriate amount of water is added to this mixture, followed by further stirring, granulating with a granulator, and air drying, to give a granule for each compound.

Formulation Example 4

4.5 parts of each of the compounds of the present invention (1) to (48), 1 part of synthetic hydrated silicon oxide fine powder, 1 part of Doriresu B (Sankyo Co., Ltd.) as a flocculant and 7 parts of clay are well mixed with a mortar, followed by stirring and mixing with a juice mixer. To the resulting mixture are added 86.5 parts of cut clay, followed by stirring and mixing well, to give a dust for each compound.

Formulation Example 5

10 parts of each of the compound of the present invention (1) to (48), 35 parts of white carbon containing 50 parts of polyoxyethylene alkyl ether sulfate ammonium salt and 55 parts of water are mixed and pulverized by the wet grinding method to give a formulation for each compound.

Formulation Example 6

0.5 parts of each of the compound of the present invention (1) to (48) are dissolved in 10 parts of dichloromethane, and the resulting solution is mixed with 89.5 parts of Iso-Par M (isoparaffine: registered trade name for EXXON CHEMICAL LTD) to give an oil solution.

Formulation Example 7

0.1 parts of each of the compound of the present invention (1) to (48) and 49.9 parts of NEO-CHIOZOL (CHUO KASEI Co., LTD) are charged into aerosol can, and aerosol valve is fixed to the can. Then 25 parts of dimethyl ether and 25 parts of LPG are filled in the can, followed by shaking and fitting an actuator on it, to give an oil aerosol.

Formulation Example 8

0.6 parts of each of the compounds of the present invention (1) to (48), 0.01 parts of BHT, 5 parts of xylene, 3.39 parts of deodorized kerosene and 1 part of emulsifier [Atmos 300 (registered trade name for ATMOS CHEMICAL LTD)] are mixed and dissolved. The solution obtained and 50 parts of distilled water are charged into aerosol container, and a valve is fixed to the container. 40 Parts of propellant (LPG) are charged under pressure through the valve to give an aqueous aerosol.

The following test example will demonstrate that the compound of the present invention have a pesticidal activity as active ingredient of a composition for controlling pests. The compounds of the present invention are designated by their compound numbers shown above.

Test Example 1

The formulation obtained according to Formulation Example 5 using the compound of the present invention (2), (3), (4), (5), (6), (7), (8), (9), (11), (12), (13), (14), (15), (16), (18), (20), (21), (22), (26), (28), (29), (30), (31), (32), (33), (34), (35), (36), (37), (38), (39), (45) and (48) respectively, was diluted with water so that the active ingredient concentration came to 500 ppm to prepare a pesticidal solution for test.

Fifty grams of molding Bonsoru 2 (produced by Sumitomo Chemical Co., Ltd.) was put into a polyethylene cup, and 10 to 15 seeds of rice were planted in the polyethylene cup. Then rice plants were grown until the second foliage leaves developed and then cut into the same height of 5 cm. The pesticidal solution for test prepared above was sprayed at the rate of 20 ml/cup to these rice plants. After the pesticidal solution sprayed onto the rice plants were dried, they were put into a plastic cup for escape prevention of test pests, and thirty first-instar larvae of *Nilaparvata lugens* were set free on the rice plants, followed by covering the plastic cup with a lid. Then the plastic cup was left in a greenhouse (25° C.). On the sixth day after the release of larvae of *Nilaparvata lugens*, the number of parasitic *Nilaparvata lugens* on the rice plants was examined.

As a result, in the treatment with each of the compound of the present invention (2), (3), (4), (5), (6), (7), (8), (9), (11), (12), (13), (14), (15), (16), (18), (20), (21), (22), (26), (28), (29), (30), (31), (32), (33), (34), (35), (36), (37), (38), (39), (45) and (48), the number of parasitic *Nilaparvata lugens* was not greater than 3.

Test Example 2

The formulation obtained according to Formulation Example 5 using the compound of the present invention (2), (4), (6), (8), (9), (11), (12), (13), (15), (18), (21), (22), (28), (29), (30), (31), (32), (33), (34), (35), (36), (37), (38), (44), (46) and (47) respectively, was diluted with water so that the active ingredient concentration came to 500 ppm to prepare a pesticidal solution for test.

A polyethylene cup was seeded with cucumber and a plant was grown until the first true leaf was developed, on which about twenty *Aphis gossypii* are allowed to be parasitic. On the next day, the above pesticidal solution for test was sprayed at a ratio of 20 ml/cup to the cucumber plant. On the sixth day after the application, the number of *Aphis gossypii* was examined.

As a result, in the treatment with each of the compound of the present invention (2), (4), (6), (8), (9), (11), (12), (13), (15), (18), (21), (22), (28), (29), (30), (31), (32), (33), (34), (35), (36), (37), (38), (44), (46) and (47), the number of parasitic insects on the sixth day after the treatment was not greater than 3.

Test Example 3

The formulation obtained according to Formulation Example 5 using the compound of the present invention (2), (3), (4), (6), (7), (8), (11), (12), (13), (15), (16), (19), (20), (21), (22), (28), (29), (30), (31), (32), (33), (34), (36), (37), (38) and (39) respectively, was diluted with water so that the active ingredient concentration came to 500 ppm to prepare a pesticidal solution for test.

On the bottom of a polyethylene cup having a diameter of 5.5 cm, a filter paper having the same diameter was laid, and 0.7 ml of the above pesticidal solution for test was added dropwise on the filter paper, followed by putting 30 mg of sucrose on it uniformly as a bait. Ten female *Musca domestica* imagoes were set free in the polyethylene cup and covered it with a lid. After 24 hours, the number of surviving and dead *Musca domestica* was examined and the rate of dead pests was calculated.

As a result, in the treatment with each of the compound of the present invention (2), (3), (4), (6), (7), (8), (11), (12), (13), (15), (16), (19), (20), (21), (22), (28), (29), (30), (31), (32), (33), (34), (36), (37), (38) and (39) the rate of dead pests was 90% or more.

Test Example 4

The formulation obtained according to Formulation Example 5 using the compound of the present invention (2), (3), (4), (6), (7), (8), (9), (11), (12), (13), (15), (16), (18), (19), (20), (21), (22), (27), (28), (29), (30), (31), (32), (33), (34), (35), (36), (37), (38), (43) and (43) respectively, was diluted with water so that the active ingredient concentration came to 500 ppm to prepare a pesticidal solution for test.

On the bottom of a polyethylene cup having a diameter of 5.5 cm, a filter paper having the same diameter was laid, and 0.7 ml of the above pesticidal solution for test was added dropwise on the filter paper, followed by putting 30 mg of sucrose on it uniformly as a bait. Two male *Blattella germanica* imagoes were set free in the polyethylene cup and covered it with a lid. After 6 days, the number of surviving and dead *Blattella germanica* was examined and the rate of dead pests was calculated.

As a result, in the treatment with each of the compound of the present invention (2), (3), (4), (6), (7), (8), (9), (11), (12), (13), (15), (16), (18), (19), (20), (21), (22), (27), (28), (29), (30), (31), (32), (33), (34), (35), (36), (37), (38), (43) and (43), the rate of dead pests was 100%.

Test Example 5

The formulation obtained according to Formulation Example 5 using the compound of the present invention (1), (2), (3), (4), (5), (6), (7), (8), (9), (10), (11), (12), (13), (14), (15), (16), (17), (18), (19), (20), (21), (22), (23), (25), (27), (28), (29), (50), (31), (32), (33), (34), (35), (36), (37), (38), (39), (41), (44), (45), (46), (47) and (48) respectively, was diluted with water so that the active ingredient concentration came to 500 ppm to prepare a pesticidal solution for test.

0.7 ml of above pesticidal solution for test was added to 100 ml of ion exchanged water (active ingredient concentration: 3.5 ppm). Twenty last-instar larvae of *Culex pipiens pallens* were set free in the solution. After one day, the number of surviving and dead *Culex pipiens pallens* was examined and the rate of dead pests was calculated.

As a result, in the treatment with each of the compound of the present invention (1), (2), (3), (4), (5), (6), (7), (8), (9), (10), (11), (12), (13), (14), (15), (16), (17), (18), (19), (20), (21), (22), (23), (25), (27), (28), (29), (50), (31), (32), (33), (34), (35), (36), (37), (38), (39), (41), (44), (45), (46), (47) and (48), the rate of dead pests was not less than 95%.

INDUSTRIAL APPLICABILITY

The compounds of the present invention have an excellent controlling activity against pests, and useful as an active ingredient of pesticide.

The invention claimed is:
1. A malononitrile compound represented by the formula (I):

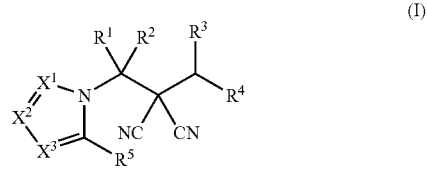

wherein, in the formula,
$R^1$ represents a C1-C5 alkyl group optionally substituted by at least one halogen atom, a C2-C5 alkenyl group optionally substituted by at least one halogen atom, a C2-C5 alkynyl group optionally substituted by at least one halogen atom or a hydrogen atom;
$R^2$ represents a C1-C5 alkyl group optionally substituted by at least one halogen atom, a C1-C5 alkoxy group optionally substituted by at least one halogen atom, a C2-C5 alkenyl group optionally substituted by at least one halogen atom, a C2-C5 alkynyl group optionally substituted by at least one halogen atom, a cyano group or a hydrogen atom;
each of $R^3$ and $R^4$ represents a C1-C5 alkyl group optionally substituted by at least one halogen atom, a C2-C5 alkenyl group optionally substituted by at least one halogen atom, a C2-C5 alkynyl group optionally substituted by at least one halogen atom, a C3-C5 cycloalkyl group optionally substituted by at least one halogen atom or at least one C1-C3 alkyl group, a C4-C5 cycloalkenyl group optionally substituted by at least one halogen atom or a hydrogen atom, or represents a C2-C6 alkanediyl group optionally substituted by at least one halogen atom or C4-C6 alkenediyl group optionally substituted by at least one halogen atom in which $R^3$ and $R^4$ are coupled one another at the end thereof;
each of $X^1$, $X^2$ and $X^3$ represents a nitrogen atom or a $CR^6$;
each of $R^5$ and $R^6$ represents a halogen atom, a cyano group, a nitro group, a hydroxyl group, a mercapto group, a formyl group, a $SF_5$ group, a carboxyl group, a C1-C5 alkyl group optionally substituted by at least one halogen atom, a C2-C5 alkenyl group optionally substituted by at least one halogen atom, a C2-C5 alkynyl group optionally substituted by at least one halogen atom, a C3-C6 cycloalkyl group optionally substituted by at least one halogen atom or at least one C1-C3 alkyl group, a C1-C5 alkoxy group optionally substituted by at least one halogen atom, a C3-C6 alkenyloxy group optionally substituted by at least one halogen atom, a C3-C6 alkynyloxy group optionally substituted by at least one halogen atom, a C1-C5 alkylthio group optionally substituted by at least one halogen atom, a C3-C5 alkenylthio group optionally substituted by at least one halogen atom, a C3-C5 alkynylthio group optionally substituted by at least one halogen atom, a C1-C5 alkylsulfinyl group optionally substituted by at least one halogen atom, a C1-C5 alkylsulfonyl group optionally substituted by at least one halogen atom, a C2-C6 alkylcarbonyl group optionally substituted by at least one halogen atom, a C2-C5 alkoxycarbonyl group optionally substituted by at least one halogen atom, a group designated by $NR^{10}R^{11}$, a group designated by $C(=X^5)NR^{12}NR^{13}$, a group designated by $(CH_2)_mQ$, a group designated by $C(=NOR^{17})R^{18}$ or a hydrogen atom;

in case of two atoms are adjoined and each of the adjoined two atoms is bonded with one of $R^5$ and $R^6$ or two $R^6$s; the $R^5$ and $R^6$, which are bonded with the adjoined two atoms or the two $R^6$s, which are bonded with the adjoined two atoms, may be coupled one another at the end thereof and represent a C2-C6 alkanediyl group optionally substituted by at least one halogen atom or C4-C6 alkenediyl group, and in this case, at least one methylene group structuring said alkanediyl group or said alkenediyl group may be replaced by an oxygen atom a sulfur atom or $NR^7$ group;

$R^7$ represents a C1-C5 alkyl group optionally substituted by at least one halogen atom, a C3-C5 alkenyl group optionally substituted by at least one halogen atom, a C3-C5 alkynyl group optionally substituted by at least one halogen atom, a C3-C6 cycloalkyl group optionally substituted by at least one halogen atom or at least one C1-C3 alkyl group, a C2-C6 alkylcarbonyl group optionally substituted by at least one halogen atom, a C2-C5 alkoxycarbonyl group optionally substituted by at least one halogen atom or a hydrogen atom; each of $R^{10}$ and $R^{11}$ represents a C1-C5 alkyl group optionally substituted by at least one halogen atom, a C3-C5 alkenyl group optionally substituted by at least one halogen atom, a C3-C5 alkynyl group optionally substituted by at least one halogen atom, a C3-C6 cycloalkyl group optionally substituted by at least one halogen atom or at least one C1-C3 alkyl group, a (C1-C5 alkoxy group optionally substituted by at least one halogen atom) C1-C3 alkyl group, a C1-C5 alkylslufinyl group optionally substituted by at least one halogen atom, a C1-C5 alkylsulfonyl group optionally substituted by at least one halogen atom, a C2-C6 alkylcarbonyl group optionally substituted by at least one halogen atom, a C2-C5 alkoxycarbonyl group optionally substituted by at least one halogen atom or a hydrogen atom;

each of $R^2$ and $R^{13}$ represents a C1-C5 alkyl group optionally substituted by at least one halogen atom, a C3-C5 alkenyl group optionally substituted by at least one halogen atom, a C3-C5 alkynyl group optionally substituted by at least one halogen atom, a C3-C6 cycloalkyl group optionally substituted by at least one halogen atom or at least one C1-C3 alkyl group, a group designated by $(CH_2)_mQ$ or a hydrogen atom;

or represents a C2-C6 alkanediyl group optionally substituted by at least one halogen atom or C4-C6 alkenediyl group optionally substituted by at least one halogen atom in which $R^{12}$ and $R^{13}$ are coupled one another at the end thereof;

each of $R^{17}$ and $R^{18}$ represents a C1-C5 alkyl group optionally substituted by at least one halogen atom, a C3-C5 alkenyl group optionally substituted by at least one halogen atom, a C3-C5 alkynyl group optionally substituted by at least one halogen atom, a C3-C6 cycloalkyl group optionally substituted by at least one halogen atom or at least one C1-C3 alkyl group, a group designated by $(CH_2)_mQ$ or a hydrogen atom;

Q represents an aryl group optionally substituted by at least one $R^{14}$; each of $R^{14}$s represents a C1-C5 alkyl group optionally substituted by at least one halogen atom, a C3-C6 cycloalkyl group optionally substituted by at least one halogen atom or at least one C1-C3 alkyl group, a C1-C5 alkoxy group optionally substituted by at least one halogen atom, C1-C5 alkylthio group optionally substituted by at least one halogen atom, a C3-C5 alkenylthio group optionally substituted by at least one halogen atom, a C3-C5 alkynylthio group optionally substituted by at least one halogen atom, a C1-C5 alkylsulfinyl group optionally substituted by at least one halogen atom, a C1-C5 alkylsulfonyl group optionally substituted by at least one halogen atom, C2-C6 alkylcarbonyl group optionally substituted by at least one halogen atom, C2-C5 alkoxycarbonyl group optionally substituted by at least one halogen atom or a halogen atom;

m represents an integer of from 0 to 5;

$X^5$ represents an oxygen atom or a sulfur atom.

2. The malononitrile compound according to claim 1, which is represented by the formula (I-1):

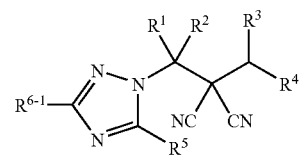

(I-1)

wherein, in the formula,
$R^1$, $R^2$, $R^3$ and $R^4$ have the same meaning as defined in claim 1;
each of $R^5$ and $R^{6-1}$ represents a halogen atom, a cyano group, a nitro group, a hydroxyl group, a mercapto group, a formyl group, a $SF_5$ group, a carboxyl group, a C1-C5 alkyl group optionally substituted by at least one halogen atom, a C2-C5 alkenyl group optionally substituted by at least one halogen atom, a C2-C5 alkynyl group optionally substituted by at least one halogen atom, a C3-C6 cycloalkyl group optionally substituted by at least one halogen atom or at least one C1-C3 alkyl group, a C1-C5 alkoxy group optionally substituted by at least one halogen atom, a C3-C6 alkenyloxy group optionally substituted by at least one halogen atom, a C3-C6 alkynyloxy group optionally substituted by at least one halogen atom, a C1-C5 alkylthio group optionally substituted by at least one halogen atom, a C3-C5 alkenylthio group optionally substituted by at least one halogen atom, a C3-C5 alkynylthio group optionally substituted by at least one halogen atom, a C1-C5 alkylsulfinyl group optionally substituted by at least one halogen atom, a C1-C5 alkylsulfonyl group optionally substituted by at least one halogen atom, a C2-C6 alkylcarbonyl group optionally substituted by at least one halogen atom, a C2-C5 alkoxycarbonyl group optionally substituted by at least one halogen atom, a phenyl group or a hydrogen atom.

3. The malononitrile compound according to claim 1, which is represented by the formula (I-2):

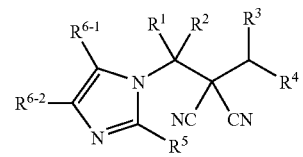

(I-2)

wherein, in the formula,
$R^1$, $R^2$, $R^3$ and $R^4$ have the same meaning as defined in claim 1;
each of $R^5$, $R^{6-1}$ and $R^{6-2}$ represents a halogen atom, a cyano group, a nitro group, a hydroxyl group, a mercapto group, a formyl group, a $SF_5$ group, a carboxyl group, a C1-C5 alkyl group optionally substituted by at least one halogen atom, a C2-C5alkenyl group optionally substituted by at least one halogen atom, a C2-C5 alkynyl group optionally substituted by at least one halogen atom, a C3-C6 cycloalkyl group optionally substituted by at least one halogen atom or at least one C1-C3 alkyl group, a C1-C5 alkoxy group optionally substituted by at least one halogen atom, a C3-C6 alkenyloxy group optionally substituted by at least one halogen atom, a C3-C6 alkynyloxy group optionally substituted by at least one halogen atom, a C1-C5 alkylthio group optionally substituted by at least one halogen atom, a C3-C5 alkenylthio group optionally substituted by at least one halogen atom, a C3-C5 alkynylthio group optionally substituted by at least one halogen atom, a C1-C5 alkylsulfinyl group optionally substituted by at least one halogen atom, a C1-C5 alkylsulfonyl group optionally substituted by at least one halogen atom, a C2-C6 alkylcarbonyl group optionally substituted by at least one halogen atom, a C2-C5 alkoxycarbonyl group optionally substituted by at least one halogen atom, a phenyl group or a hydrogen atom.

4. The malononitrile compound according to claim 1, which is represented by the formula (I-3):

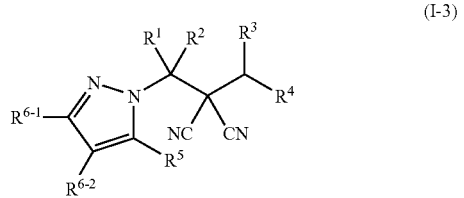

(I-3)

wherein, in the formula,

R$^1$, R$^2$, R$^3$ and R$^4$ have the same meaning as defined in claim 1;

each of R$^5$, R$^{6-1}$ and R$^{6-2}$ represents a halogen atom, a cyano group, a nitro group, a hydroxyl group, a mercapto group, a formyl group, a SF$_5$ group, a carboxyl group, a C1-C5 alkyl group optionally substituted by at least one halogen atom, a C2-C5alkenyl group optionally substituted by at least one halogen atom, a C2-C5 alkynyl group optionally substituted by at least one halogen atom, a C3-C6 cycloalkyl group optionally substituted by at least one halogen atom or at least one C1-C3 alkyl group, a C1-C5 alkoxy group optionally substituted by at least one halogen atom, a C3-C6 alkenyloxy group optionally substituted by at least one halogen atom, a C3-C6 alkynyloxy group optionally substituted by at least one halogen atom, a C1-C5 alkylthio group optionally substituted by at least one halogen atom, a C3-C5 alkenylthio group optionally substituted by at least one halogen atom, a C3-C5 alkynylthio group optionally substituted by at least one halogen atom, a C1-C5 alkylsulfinyl group optionally substituted by at least one halogen atom, a C1-C5 alkylsulfonyl group optionally substituted by at least one halogen atom, a C2-C6 alkylcarbonyl group optionally substituted by at least one halogen atom, a C2-C5 alkoxycarbonyl group optionally substituted by at least one halogen atom, a phenyl group or a hydrogen atom.

5. The malononitrile compound according to claim 1, which is represented by the formula (I-4):

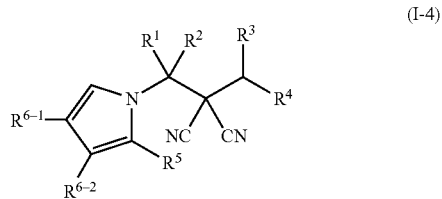

(I-4)

wherein, in the formula,

R$^1$, R$^2$, R$^3$ and R$^4$ have the same meaning as defined in claim 1;

each of R$^5$, R$^{6-1}$ and R$^{6-2}$ represents a halogen atom, a cyano group, a nitro group, a hydroxyl group, a mercapto group, a formyl group, a SF$_5$ group, a carboxyl group, a C1-C5 alkyl group optionally substituted by at least one halogen atom, a C2-C5alkenyl group optionally substituted by at least one halogen atom, a C2-C5 alkynyl group optionally substituted by at least one halogen atom, a C3-C6 cycloalkyl group optionally substituted by at least one halogen atom or at least one C1-C3 alkyl group, a C1-C5 alkoxy group optionally substituted by at least one halogen atom, a C3-C6 alkenyloxy group optionally substituted by at least one halogen atom, a C3-C6 alkynyloxy group optionally substituted by at least one halogen atom, a C1-C5 alkylthio group optionally substituted by at least one halogen atom, a C3-C5 alkenylthio group optionally substituted by at least one halogen atom, a C3-C5 alkynylthio group optionally substituted by at least one halogen atom, a C1-C5 alkylsulfinyl group optionally substituted by at least one halogen atom, a C1-C5 alkylsulfonyl group optionally substituted by at least one halogen atom, a C2-C6 alkylcarbonyl group optionally substituted by at least one halogen atom, a C2-C5 alkoxycarbonyl group optionally substituted by at least one halogen atom, a phenyl group or a hydrogen atom.

6. The malononitrile compound according to any one of claim 2 to claim 5, wherein R$^5$ is a hydrogen atom;

each of R$^6$, R$^{6-1}$ and R$^{6-2}$ is a halogen atom, a C1-C5 alkyl group optionally substituted by at least one halogen atom, a C1-C5 alkoxy group optionally substituted by at least one halogen atom, a C1-C5 alkylthio group optionally substituted by at least one halogen atom or a hydrogen atom.

7. The malononitrile compound according to any one of claim 2 to claim 5, wherein R$^1$, R$^2$, R$^3$ and R$^5$ are hydrogen atoms;

R$^4$ is a C1-C5 alkyl group optionally substituted by at least one halogen atom or a C2-C5 alkenyl group optionally substituted by at least one halogen atom;

each of R$^{6-1}$ and R$^{6-2}$ is a halogen atom, a C1-C5 alkyl group optionally substituted by at least one halogen atom, a C1-C5 alkoxy group optionally substituted by at least one halogen atom, a C1-C5 alkylthio group optionally substituted by at least one halogen atom or a hydrogen atom.

8. The malononitrile compound according to any one of claim 2 to claim 5, wherein
$R^1$, $R^2$, $R^3$ and $R^5$ are hydrogen atoms;
$R^4$ is a 2,2,2-trifluoroethyl group or a vinyl group;
each of $R^{6-1}$ and $R^{6-2}$ is a halogen atom, a C1-C5 alkyl group optionally substituted by at least one halogen atom, a C1-C5 alkoxy group optionally substituted by at least one halogen atom, a C1-C5 alkylthio group optionally substituted by at least one halogen atom or a hydrogen atom.

9. A pesticide composition comprising an effective amount of the malononitrile compound according to claim 1 and a carrier.

10. A method for controlling pests comprising applying an effective amount of the malononitrile compound according to claim 1 to pests or at a habitat of pests.

* * * * *